(12) United States Patent
Twomey et al.

(10) Patent No.: US 12,274,844 B2
(45) Date of Patent: Apr. 15, 2025

(54) THROMBUS REMOVAL DEVICE

(71) Applicant: Covidien LP, Mansfield, MA (US)

(72) Inventors: Alan M. Twomey, Minneapolis, MN (US); Shawn Phillips, Belle Plaine, MN (US); Wanda F. Dent, Chanhassen, MN (US); Nathan K. Weidenhamer, Minneapolis, MN (US); Brandon Phan, Minneapolis, MN (US); Noah Johnson, Lancaster, CA (US); Ryan R. Davis, Plymouth, MN (US); Daniel M. Gelfman, Golden Valley, MN (US)

(73) Assignee: Covidien LP, Mansfield, MA (US)

( * ) Notice: Subject to any disclaimer, the term of this patent is extended or adjusted under 35 U.S.C. 154(b) by 428 days.

(21) Appl. No.: 17/132,823

(22) Filed: Dec. 23, 2020

(65) Prior Publication Data

US 2021/0128893 A1    May 6, 2021

Related U.S. Application Data

(63) Continuation-in-part of application No. 16/908,544, filed on Jun. 22, 2020, now abandoned.

(Continued)

(51) Int. Cl.
*A61B 17/221*    (2006.01)
*A61F 2/01*    (2006.01)
*A61M 25/10*    (2013.01)

(52) U.S. Cl.
CPC ..... *A61M 25/10181* (2013.11); *A61B 17/221* (2013.01); *A61F 2/013* (2013.01); *A61M 25/1025* (2013.01); *A61M 2025/109* (2013.01)

(58) Field of Classification Search
CPC .............. A61B 17/221; A61B 17/2212; A61B 2017/00477; A61B 17/3207–320783;
(Continued)

(56) References Cited

U.S. PATENT DOCUMENTS 4,728,319 A    3/1988    Masch
4,886,067 A *  12/1989   Palermo .......... A61M 25/09033
                                                           604/528

(Continued)

FOREIGN PATENT DOCUMENTS

CA        2603544     10/2006
CN       105377157     3/2016
(Continued)

OTHER PUBLICATIONS

U.S. Appl. No. 17/197,856, filed Mar. 10, 2021, naming inventors Phillips et al.

(Continued)

*Primary Examiner* — Kathleen S Holwerda
*Assistant Examiner* — Serenity A Miller
(74) *Attorney, Agent, or Firm* — Shumaker & Sieffert, P.A.

(57) ABSTRACT

In some examples, a catheter assembly includes a delivery catheter defining a delivery catheter lumen, a delivery catheter handle connected to the delivery catheter, a retrieval catheter defining a retrieval catheter lumen configured to receive the delivery catheter, and a retrieval catheter handle connected to the retrieval catheter. A proximal end of the retrieval catheter handle is configured to removably couple to a distal end of the delivery catheter handle.

28 Claims, 21 Drawing Sheets

Related U.S. Application Data

(60) Provisional application No. 62/936,705, filed on Nov. 18, 2019, provisional application No. 62/865,714, filed on Jun. 24, 2019.

(58) Field of Classification Search
CPC .............. A61B 17/22012; A61B 17/22; A61F 2/01–02; A61F 2/95; A61F 2/966; A61M 25/01–0194
USPC ........................................................ 623/1.11
See application file for complete search history.

(56) References Cited

U.S. PATENT DOCUMENTS

| | | | |
|---|---|---|---|
| 5,092,839 A | 3/1992 | Kipperman | |
| 5,391,172 A * | 2/1995 | Williams | A61F 2/958 |
| | | | 606/198 |
| 5,549,626 A | 8/1996 | Miller et al. | |
| 5,766,191 A | 6/1998 | Trerotola | |
| 5,814,064 A | 9/1998 | Daniel et al. | |
| 5,817,104 A | 10/1998 | Bilitz et al. | |
| 6,001,118 A | 12/1999 | Daniel et al. | |
| 6,027,520 A | 2/2000 | Tsugita et al. | |
| 6,053,932 A | 4/2000 | Daniel et al. | |
| 6,059,796 A | 5/2000 | Bilitz et al. | |
| 6,090,118 A | 7/2000 | McGuckin, Jr. | |
| 6,093,196 A | 7/2000 | Okada | |
| 6,152,946 A | 11/2000 | Broome et al. | |
| 6,179,859 B1 | 1/2001 | Bates et al. | |
| 6,221,006 B1 | 4/2001 | Dubrul et al. | |
| 6,238,412 B1 | 5/2001 | Dubrul et al. | |
| 6,245,089 B1 | 6/2001 | Daniel et al. | |
| 6,258,115 B1 | 7/2001 | Dubrul | |
| 6,361,545 B1 | 3/2002 | Macoviak et al. | |
| 6,413,235 B1 | 7/2002 | Parodi | |
| 6,454,775 B1 | 9/2002 | Demarais et al. | |
| 6,468,291 B2 | 10/2002 | Bates et al. | |
| 6,572,593 B1 * | 6/2003 | Daum | A61B 17/3417 |
| | | | 604/164.13 |
| 6,602,264 B1 | 8/2003 | McGuckin, Jr. | |
| 6,652,548 B2 | 11/2003 | Evans et al. | |
| 6,660,014 B2 | 12/2003 | Demarais et al. | |
| 6,663,652 B2 | 12/2003 | Daniel et al. | |
| 6,695,858 B1 | 2/2004 | Dubrul et al. | |
| 6,699,260 B2 | 3/2004 | Dubrul et al. | |
| 6,702,830 B1 | 3/2004 | Demarais et al. | |
| 6,743,247 B1 | 6/2004 | Levinson et al. | |
| 6,824,551 B2 | 11/2004 | Trerotola | |
| 6,945,977 B2 | 9/2005 | Demarais et al. | |
| 7,037,316 B2 | 5/2006 | McGuckin, Jr. et al. | |
| 7,056,328 B2 | 6/2006 | Arnott | |
| 7,108,704 B2 | 9/2006 | Trerotola | |
| 7,137,991 B2 | 11/2006 | Fedie | |
| 7,217,255 B2 | 5/2007 | Boyle | |
| 7,220,269 B1 | 5/2007 | Ansel et al. | |
| 7,354,445 B2 | 4/2008 | Nicholson | |
| 7,507,246 B2 | 3/2009 | McGuckin et al. | |
| 7,645,261 B2 | 1/2010 | Hinchliffe | |
| 7,655,016 B2 | 2/2010 | Demarais et al. | |
| 7,691,123 B2 | 4/2010 | Tsugita et al. | |
| 7,819,887 B2 | 10/2010 | McGuckin, Jr. et al. | |
| 7,909,801 B2 | 3/2011 | Hinchliffe | |
| 7,955,345 B2 | 6/2011 | Kucharczyk et al. | |
| 8,062,258 B2 | 11/2011 | Demarais et al. | |
| 8,062,317 B2 | 11/2011 | McGuckin, Jr. et al. | |
| 8,092,395 B2 | 1/2012 | Lupton et al. | |
| 8,277,470 B2 | 10/2012 | Demarais et al. | |
| 8,366,735 B2 | 2/2013 | Bose | |
| 8,409,242 B2 | 4/2013 | Clubb et al. | |
| 8,414,543 B2 | 4/2013 | McGuckin, Jr. et al. | |
| 8,435,218 B2 | 5/2013 | Hinchliffe | |
| 8,449,566 B2 | 5/2013 | Finitsis | |
| 8,465,511 B2 | 6/2013 | McGuckin, Jr. et al. | |
| 8,480,697 B2 | 7/2013 | Kucharczyk et al. | |
| 8,545,447 B2 | 10/2013 | Demarais et al. | |
| 8,603,122 B2 | 12/2013 | Pokorney et al. | |
| 8,647,359 B2 | 2/2014 | Broome et al. | |
| 8,784,434 B2 | 7/2014 | Rosenbluth et al. | |
| 8,801,748 B2 | 8/2014 | Martin | |
| 8,828,022 B2 | 9/2014 | White et al. | |
| 8,968,330 B2 | 3/2015 | Rosenbluth et al. | |
| 9,017,294 B2 | 4/2015 | McGuckin, Jr. et al. | |
| 9,126,016 B2 | 9/2015 | Fulton | |
| 9,149,609 B2 | 10/2015 | Ansel et al. | |
| 9,186,487 B2 | 11/2015 | Dubrul et al. | |
| 9,259,237 B2 | 2/2016 | Quick et al. | |
| 9,387,098 B2 | 7/2016 | Ferrera et al. | |
| 9,408,620 B2 | 8/2016 | Rosenbluth et al. | |
| 9,427,252 B2 | 8/2016 | Sos | |
| 9,439,664 B2 | 9/2016 | Sos | |
| 9,456,834 B2 | 10/2016 | Folk | |
| 9,474,543 B2 | 10/2016 | McGuckin, Jr. et al. | |
| 9,498,604 B2 | 11/2016 | Dubrul et al. | |
| 9,561,094 B2 | 2/2017 | Fulton | |
| 9,700,332 B2 | 7/2017 | Marchand et al. | |
| 9,827,084 B2 | 11/2017 | Bonnette et al. | |
| 9,844,387 B2 | 12/2017 | Marchand et al. | |
| 9,913,741 B2 | 3/2018 | Melsheimer et al. | |
| 9,924,957 B2 | 3/2018 | McGuckin, Jr. et al. | |
| 9,924,958 B2 | 3/2018 | Martin et al. | |
| 9,943,397 B2 | 4/2018 | Bonnette et al. | |
| 9,987,028 B2 * | 6/2018 | Lowinger | A61B 17/221 |
| 10,045,790 B2 | 8/2018 | Cox et al. | |
| 10,070,878 B2 | 9/2018 | Ma | |
| 10,085,760 B2 | 10/2018 | Imai et al. | |
| 10,092,324 B2 | 10/2018 | Gillespie et al. | |
| 10,098,651 B2 | 10/2018 | Marchand et al. | |
| 10,117,671 B2 | 11/2018 | McGuckin, Jr. et al. | |
| 10,123,803 B2 | 11/2018 | Ferrera et al. | |
| 10,231,751 B2 | 3/2019 | Sos | |
| 10,307,177 B2 | 6/2019 | Bonneau | |
| 10,342,571 B2 | 7/2019 | Marchand et al. | |
| 10,448,969 B2 | 10/2019 | Sutton et al. | |
| 10,524,811 B2 | 1/2020 | Marchand et al. | |
| 10,588,655 B2 | 3/2020 | Rosenbluth et al. | |
| 10,743,907 B2 | 8/2020 | Bruzzi et al. | |
| 10,779,852 B2 | 9/2020 | Bruzzi et al. | |
| 2002/0004667 A1 | 1/2002 | Adams et al. | |
| 2002/0082639 A1 | 6/2002 | Broome et al. | |
| 2002/0165576 A1 | 11/2002 | Boyle et al. | |
| 2003/0150821 A1 | 8/2003 | Bates | |
| 2003/0153943 A1 | 8/2003 | Michael et al. | |
| 2004/0138694 A1 | 7/2004 | Tran et al. | |
| 2005/0119688 A1 | 6/2005 | Bergheim | |
| 2005/0159770 A1 | 7/2005 | Divani et al. | |
| 2006/0015068 A1 * | 1/2006 | Amisar | A61M 25/0637 |
| | | | 604/164.01 |
| 2006/0173407 A1 * | 8/2006 | Shaughnessy | A61M 25/0105 |
| | | | 604/95.01 |
| 2006/0224179 A1 | 10/2006 | Kucharczyk | |
| 2006/0229645 A1 * | 10/2006 | Bonnette | A61B 17/320758 |
| | | | 606/159 |
| 2007/0135832 A1 | 6/2007 | Wholey et al. | |
| 2008/0091223 A1 | 4/2008 | Pokorney | |
| 2009/0198269 A1 | 8/2009 | Hannes et al. | |
| 2009/0209831 A1 | 8/2009 | Kucharczyk | |
| 2009/0292307 A1 | 11/2009 | Razack | |
| 2010/0268264 A1 | 10/2010 | Bonnette et al. | |
| 2010/0318097 A1 | 12/2010 | Ferrera et al. | |
| 2011/0160741 A1 | 6/2011 | Asano et al. | |
| 2011/0196414 A1 | 8/2011 | Porter et al. | |
| 2011/0230908 A1 | 9/2011 | Finitsis | |
| 2011/0230909 A1 | 9/2011 | Kucharczyk | |
| 2012/0101510 A1 * | 4/2012 | Lenker | A61B 17/22 |
| | | | 606/159 |
| 2012/0172920 A1 * | 7/2012 | Fifer | A61F 2/012 |
| | | | 606/200 |
| 2012/0197276 A1 | 8/2012 | Lupton et al. | |
| 2013/0204351 A1 | 8/2013 | Cox et al. | |
| 2014/0005714 A1 | 1/2014 | Quick et al. | |
| 2014/0094841 A1 | 4/2014 | Sutton et al. | |
| 2014/0236219 A1 | 8/2014 | Dubrul et al. | |
| 2014/0303667 A1 | 10/2014 | Cox et al. | |
| 2014/0303719 A1 | 10/2014 | Cox et al. | |

(56) References Cited

U.S. PATENT DOCUMENTS

| | | |
|---|---|---|
| 2015/0025555 A1 | 1/2015 | Sos |
| 2015/0238207 A1 | 8/2015 | Cox et al. |
| 2015/0265299 A1 | 9/2015 | Cooper et al. |
| 2015/0297251 A1 | 10/2015 | Sos |
| 2015/0351770 A1 | 12/2015 | Fulton, III |
| 2015/0351775 A1 | 12/2015 | Fulton, III |
| 2016/0022293 A1 | 1/2016 | Dubrul et al. |
| 2016/0030155 A1 | 2/2016 | Cox et al. |
| 2016/0038174 A1 | 2/2016 | Bruzzi et al. |
| 2016/0067444 A1 | 3/2016 | Allen et al. |
| 2016/0106446 A1 | 4/2016 | Welch et al. |
| 2016/0206344 A1 | 7/2016 | Bruzzi et al. |
| 2016/0220346 A1 | 8/2016 | Bonnette et al. |
| 2016/0256180 A1 | 9/2016 | Vale et al. |
| 2016/0262790 A1 | 9/2016 | Rosenbluth et al. |
| 2017/0105745 A1 | 4/2017 | Rosenbluth et al. |
| 2017/0112514 A1 | 4/2017 | Marchand et al. |
| 2017/0143359 A1 | 5/2017 | Nguyen |
| 2017/0245873 A1 | 8/2017 | Diamant et al. |
| 2017/0333076 A1 | 11/2017 | Bruzzi |
| 2018/0206865 A1 | 3/2018 | Martin et al. |
| 2018/0193043 A1* | 7/2018 | Marchand ............... A61F 2/013 |
| 2018/0200040 A1 | 7/2018 | Wasdyke et al. |
| 2018/0256177 A1 | 9/2018 | Cooper et al. |
| 2018/0256178 A1 | 9/2018 | Cox et al. |
| 2018/0271547 A1 | 9/2018 | Ulm, III |
| 2018/0361116 A1 | 12/2018 | Quick et al. |
| 2019/0046219 A1 | 2/2019 | Marchand et al. |
| 2019/0231373 A1 | 8/2019 | Quick |
| 2019/0321071 A1 | 10/2019 | Marchand et al. |
| 2020/0039745 A1 | 2/2020 | Khodl et al. |
| 2020/0046368 A1 | 2/2020 | Merritt et al. |
| 2020/0155293 A1 | 5/2020 | Morrison et al. |
| 2020/0397452 A1 | 12/2020 | Twomey et al. |

FOREIGN PATENT DOCUMENTS

| | | |
|---|---|---|
| CN | 105662647 A | 6/2016 |
| CN | 105852933 A | 8/2016 |
| CN | 106420004 A | 2/2017 |
| CN | 107212914 A | 9/2017 |
| CN | 110338878 A | 10/2019 |
| CN | 110495926 A | 11/2019 |
| DE | 602005025982 | 3/2011 |
| DE | 202013009532 | 11/2013 |
| EP | 1350473 | 10/2003 |
| EP | 1727584 | 12/2006 |
| EP | 2319575 A1 | 5/2011 |
| EP | 1871455 | 12/2014 |
| EP | 2967614 | 11/2016 |
| EP | 3364891 | 8/2018 |
| EP | 3539486 | 9/2019 |
| EP | 3003175 | 8/2020 |
| JP | 2011101674 | 5/2011 |
| JP | 4731471 B2 | 7/2011 |
| JP | 5805736 B2 | 11/2015 |
| WO | 1996/23446 | 8/1996 |
| WO | 99/23952 A1 | 5/1999 |
| WO | 2000/53120 | 9/2000 |
| WO | 2004/093966 A1 | 11/2004 |
| WO | 2006107641 | 10/2006 |
| WO | 2009/055782 A1 | 4/2009 |
| WO | 2009/077203 | 6/2009 |
| WO | 2011/82319 A1 | 7/2011 |
| WO | 2012/09675 A2 | 1/2012 |
| WO | 2014141226 | 9/2014 |
| WO | 2015/187196 A1 | 12/2015 |
| WO | 2015183338 | 12/2015 |
| WO | 2017/070702 A2 | 4/2017 |
| WO | 2017/074530 | 5/2017 |
| WO | WO-2017100412 A1 * | 6/2017 ........... A61B 17/295 |
| WO | 2018112221 A1 | 6/2018 |

OTHER PUBLICATIONS

Office Action from U.S. Appl. No. 16/908,544 dated Jan. 19, 2023, 20 pp.
Advisory Action from U.S. Appl. No. 16/908,544 dated Dec. 14, 2022, 3 pp.
Response to Extended Search Report dated May 3, 2022, from counterpart European Application No. 21214405.9 filed Dec. 20, 2022, 27 pp.
Office Action from U.S. Appl. No. 16/908,544, dated Jun. 22, 2022, 17 pp.
Extended Search Report from counterpart European Application No. 21214405.9 dated May 3, 2022, 11 pp.
Final Office Action from U.S. Appl. No. 16/908,544 dated Oct. 4, 2022, 17 pp.
Response to Office Action dated Jun. 22, 2022 from U.S. Appl. No. 16/908,544, filed Sep. 22, 2022, 14 pp.
International Preliminary Report on Patentability from International Application No. PCT/US0020/039067 dated Dec. 28, 2021, 7 pp.
International Search Report of International Application No. PCT/US2020/039067 dated Sep. 17, 2020, 3 pp.
Response to Communication Pursuant to Rules 161(1) and 162 EPC dated Feb. 1, 2022, from counterpart European Application No. 20743396.2, filed Jul. 26, 2022, 23 pp.
Response to Final Office Action dated Oct. 4, 2022 from U.S. Appl. No. 16/908,544, filed Nov. 28, 2022, 11 pp.
Final Office Action from U.S. Appl. No. 16/908,544 dated Jul. 19, 2023, 23 pp.
Response to Office Action dated Jan. 19, 2023 from U.S. Appl. No. 16/908,544, filed Apr. 18, 2023, 11 pp.
Advisory Action from U.S. Appl. No. 16/908,544 dated Sep. 22, 2023, 3 pp.
Office Action from U.S. Appl. No. 16/908,544 dated Oct. 24, 2023, 26 pp.
Response to Communication pursuant to Article 94(3) EPC dated Jun. 14, 2023, from counterpart European Application No. 21214405.9 filed Sep. 6, 2023, 15 pp.
Communication pursuant to Article 94(3) EPC from counterpart European Application No. 21214405.9 dated Jun. 14, 2023, 5 pp.
Response to Final Office Action dated Jul. 19, 2023 from U.S. Appl. No. 16/908,544, filed Sep. 6, 2023, 14 pp.
Response to Office Action dated Oct. 24, 2023 from U.S. Appl. No. 16/908,544, filed Dec. 21, 2023, 11 pp.

* cited by examiner

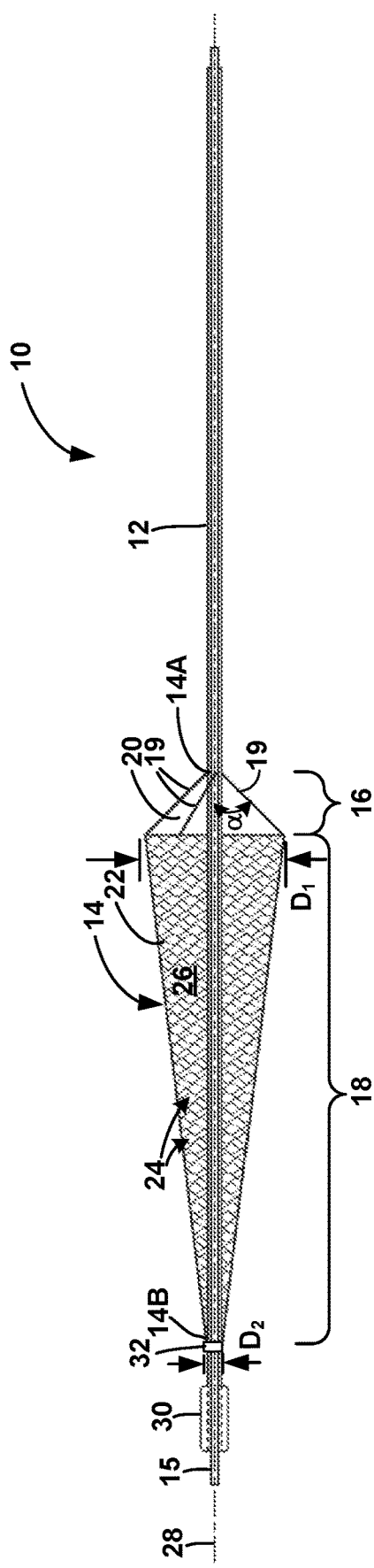
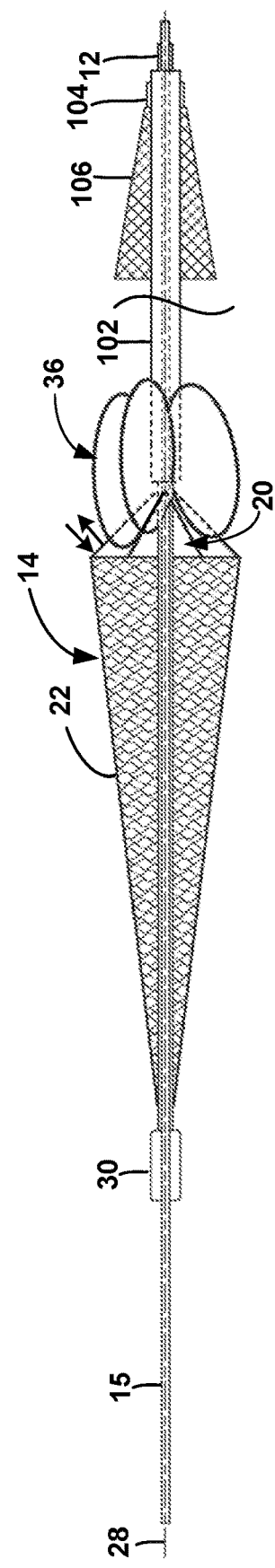
FIG. 1
FIG. 2A

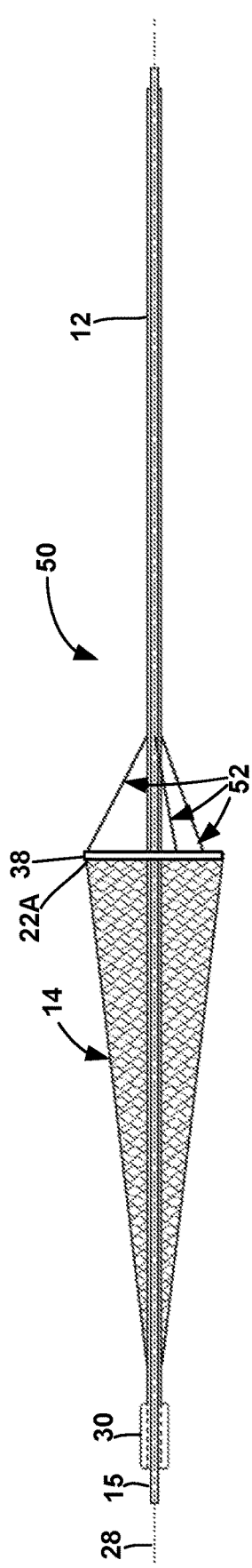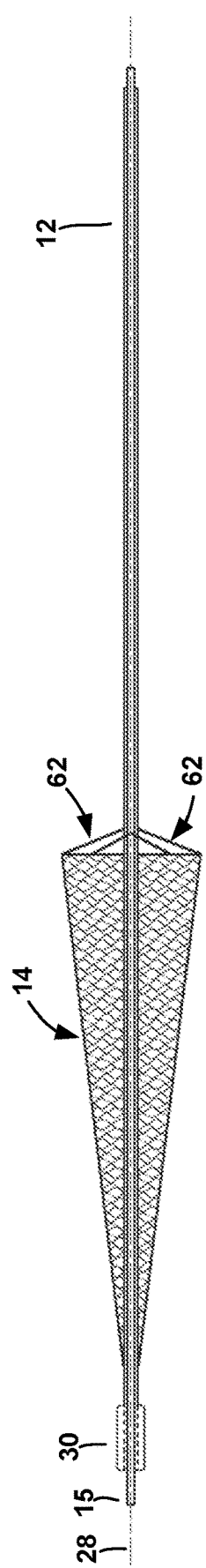
FIG. 4
FIG. 5

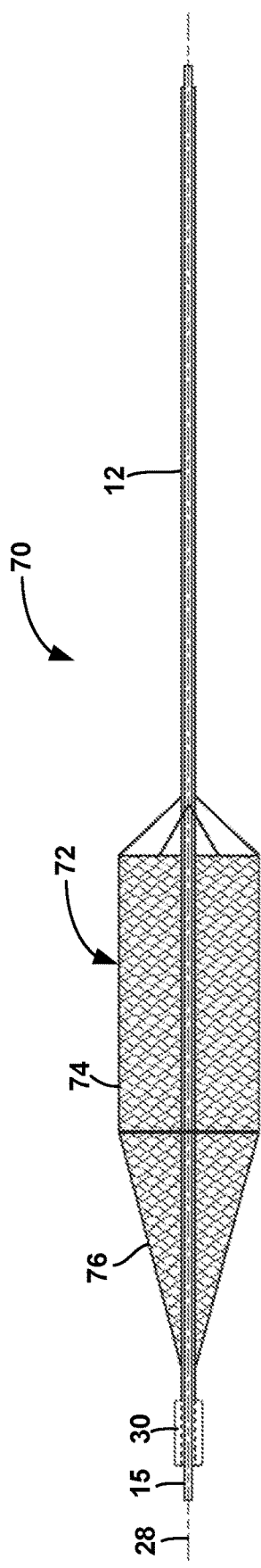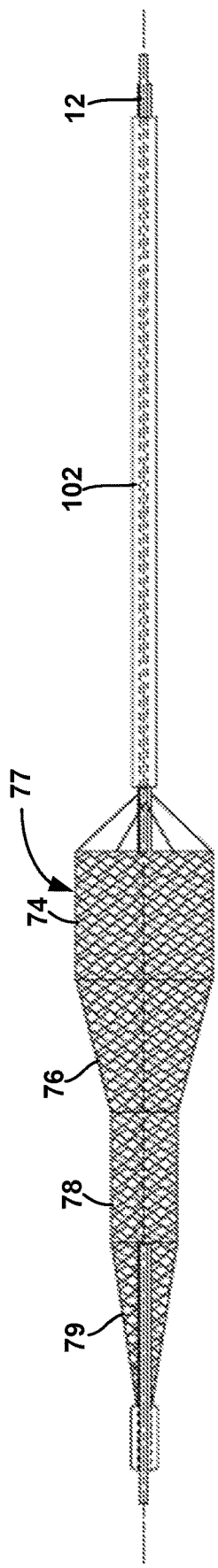
FIG. 6A
FIG. 6B

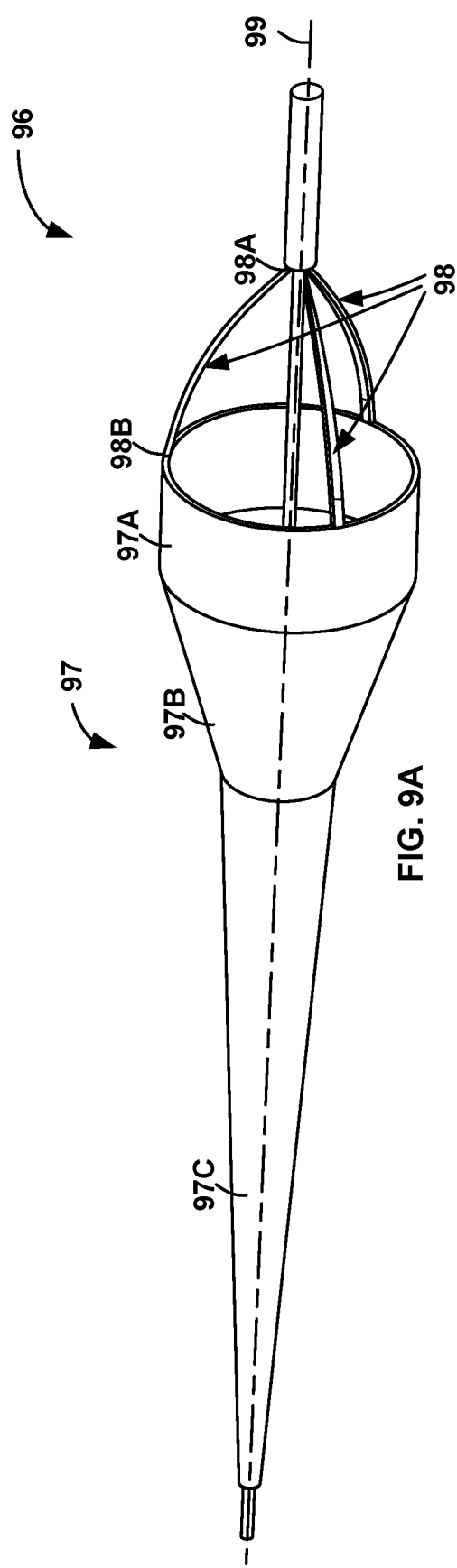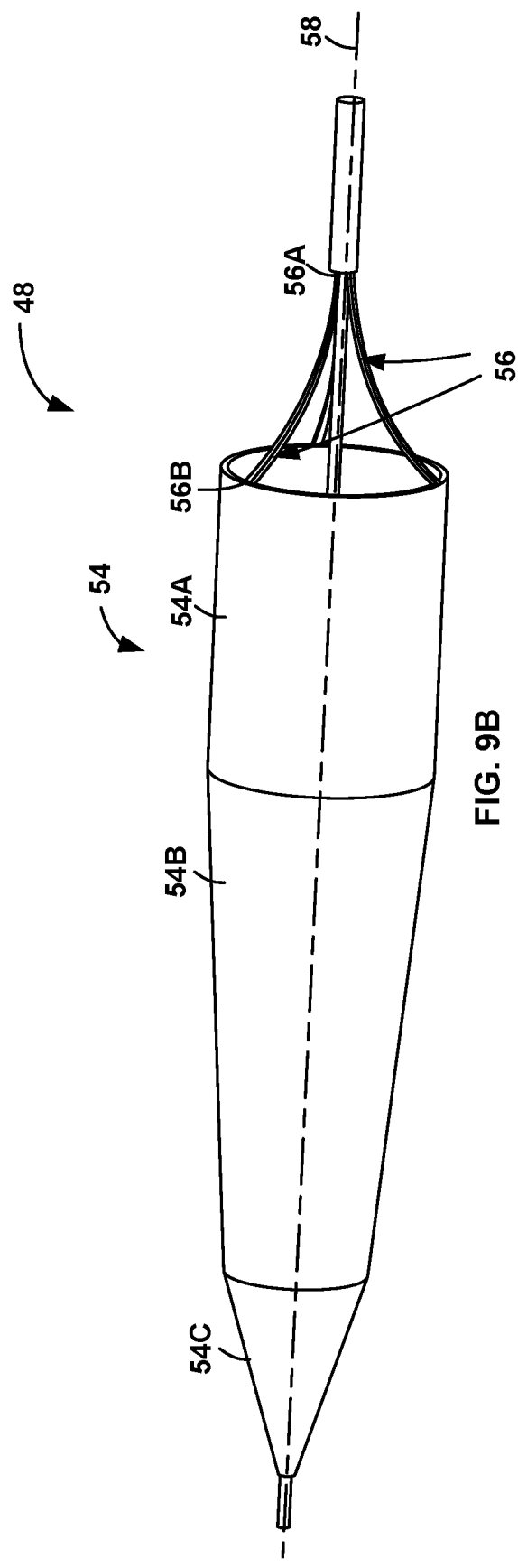
FIG. 9A
FIG. 9B

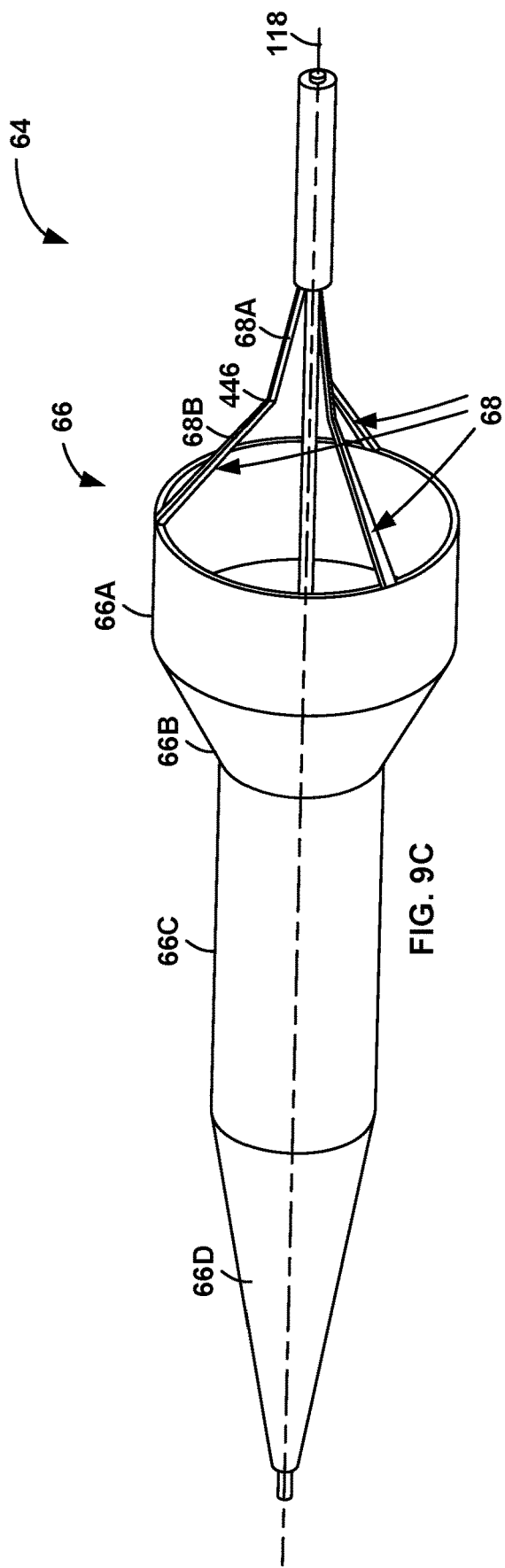
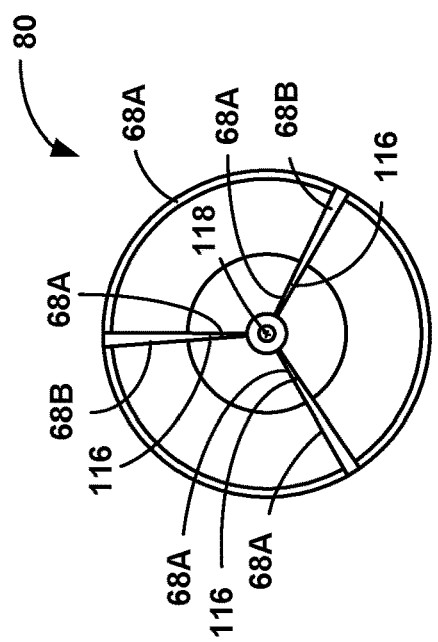
FIG. 9C
FIG. 9D

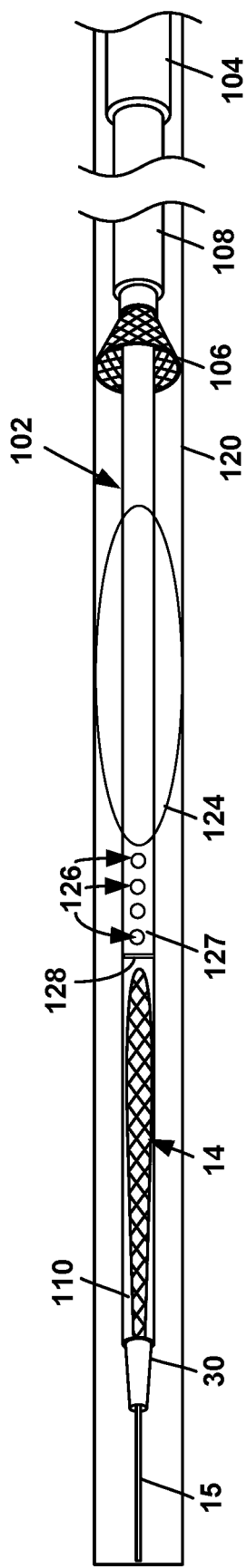
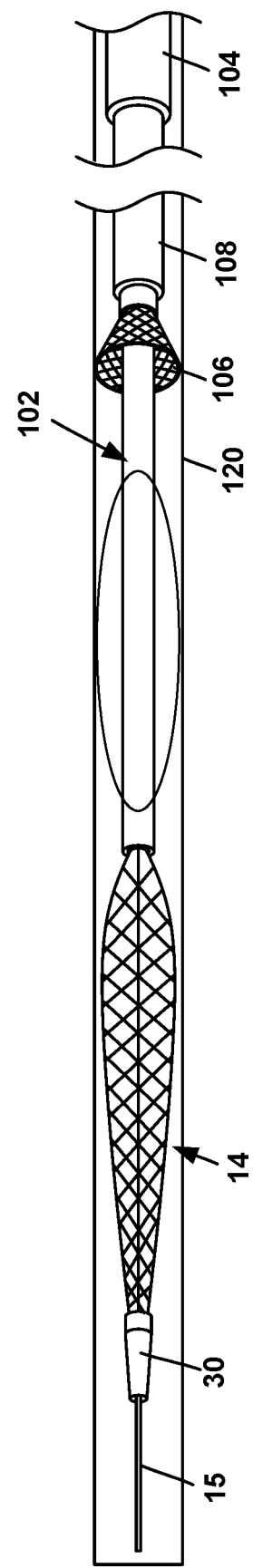
FIG. 12A
FIG. 12B

THROMBUS REMOVAL DEVICE

This application is a continuation-in-part of U.S. patent application Ser. No. 16/908,544, filed Jun. 22, 2020, and entitled, "THROMBUS REMOVAL DEVICE," which claims the benefit of U.S. Provisional Application No. 62/865,714, filed Jun. 24, 2019, and entitled, "THROMBUS REMOVAL DEVICE," and the benefit of U.S. Provisional Application No. 62/936,705, filed Nov. 18, 2019, and entitled, "THROMBUS REMOVAL DEVICE, the entire content of each of which is incorporated by reference.

TECHNICAL FIELD

The disclosure relates to removal of occlusive material from vasculature of a patient.

BACKGROUND

In some medical procedures, a thrombus or other occlusive material is removed from a body lumen (e.g., a blood vessel) to maintain the patency of the body lumen. When the thrombus is in the vasculature of a patient, removal of at least part of the thrombus from the vasculature can alleviate symptoms associated with the occlusion or help prevent the thrombus from dislodging, moving through the bloodstream, and creating an embolism, e.g., a pulmonary embolism.

SUMMARY

The disclosure describes example thrombus-removal devices that include an elongated support member and an expandable element configured to segment the thrombus into smaller pieces as the thrombus moves into a basket defined by the expandable element. The expandable element is configured to expand radially outward from a delivery configuration to a deployed configuration. In the deployed configuration, the expandable element defines a proximal mouth configured to receive a thrombus and a distal basket configured to receive at least part of the thrombus after it has moved through the proximal mouth. A proximal portion of the expandable element defines a plurality of arms configured to segment the thrombus into smaller pieces.

In some examples, the thrombus-removal device is configured to be moved proximally through a thrombus while the expandable element is in its deployed configuration in order to collect at least part of the thrombus in the basket. As the expandable element moves proximally through the thrombus, the plurality of arms segment the thrombus into smaller pieces as the thrombus moves through the proximal mouth of the expandable element and into the basket.

In some examples, in the deployed configuration, the expandable element tapers in a distal direction along a majority of a length of a distal portion of the expandable element. For example, the basket defined by the expandable element may taper from the proximal mouth to a distal end of the expandable element. Due to the distal taper of the expandable element, the expandable element is configured to compress thrombus positioned in the basket as the expandable element is proximally withdrawn into a retrieval catheter. Compression of the thrombus may expel water from the thrombus and dehydrate the thrombus, such that the thrombus decreases in volume in the basket. The tapered shape may also help distribute the thrombus longitudinally within the basket, which may help mitigate the risk of having too much relatively rigid material (e.g., the dehydrated thrombus) at the distal-most end of the basket. A relatively large bulk of relatively rigid material at the distal-most end of the basket may interfere with the proximal withdrawal of the thrombus-removal device into a retrieval catheter.

In some examples a catheter assembly includes a delivery catheter, a retrieval catheter, and a thrombus-removal device. The delivery catheter includes a delivery catheter handle configured to control expansion and contraction of an expandable element of the thrombus-removal device, and the retrieval catheter includes a retrieval catheter handle configured to control expansion and contraction of a retrieval funnel. For example, the delivery catheter handle may include a delivery catheter actuator configured to retract the delivery catheter relative to the expandable element to enable expansion of the expandable element. As another example, a retrieval catheter handle may include a retrieval catheter actuator configured to retract a cover sheath relative to the retrieval funnel to enable expansion of the retrieval funnel.

In some examples, the delivery catheter handle and the retrieval catheter handle are configured to increase the ease with which a medical procedure is performed using the catheter assembly. For example, in some examples, the delivery catheter and retrieval catheter handles are configured to removably couple (e.g., lock) together, which may enable one-handed manipulation of the catheter assembly by a clinician while minimizing the loads that are applied to the inner lumens of the delivery catheter and the retrieval catheter by the clinician. In addition, one-handed manipulation may leave the other hand of the clinician free to perform other tasks. In some examples, the delivery catheter actuator may partially define or be otherwise fluidically integrated with a fluid pathway (e.g., an inner lumen) of the delivery catheter. In some examples, the retrieval catheter handle defines an aspiration port and includes a removable adaptor configured to modify a bore size of the aspiration port for different applications during a thrombus-removal procedure.

In a first example, a catheter assembly includes a delivery catheter; a delivery catheter handle connected to the delivery catheter; a retrieval catheter defining a retrieval catheter lumen configured to receive the delivery catheter; and a retrieval catheter handle connected to the retrieval catheter. A proximal end of the retrieval catheter handle is configured to removably couple to a distal end of the delivery catheter handle.

In a second example, a catheter assembly includes a delivery catheter defining a delivery catheter lumen; an expandable element configured to be received within the delivery catheter lumen, wherein the expandable element is configured to receive a thrombus; a delivery catheter handle connected to the delivery catheter, the delivery catheter handle comprising an actuator configured to cause expansion and contraction of the expandable element, wherein the actuator defines an actuator lumen that is fluidically coupled to the delivery catheter lumen; a retrieval catheter defining a retrieval catheter lumen configured to receive the delivery catheter; and a retrieval catheter handle connected to the retrieval catheter.

In a third example, a catheter assembly includes a delivery catheter defining a delivery catheter lumen extending along a longitudinal axis; a delivery catheter handle connected to the delivery catheter, wherein the delivery catheter handle comprises an actuator configured to cause movement of the delivery catheter along the longitudinal axis, wherein the actuator defines an actuator lumen that is fluidically coupled to the delivery catheter lumen; a retrieval catheter defining a retrieval catheter lumen configured to receive the delivery catheter; and a retrieval catheter handle connected to the retrieval catheter, wherein a proximal end of the retrieval catheter handle is configured to removably couple to a distal end of the delivery catheter handle.

In some examples, a method includes: connecting a distal end of a delivery catheter handle of a delivery catheter of a catheter assembly to a proximal end of a retrieval catheter handle of a retrieval catheter of the catheter assembly; navigating the catheter assembly through vasculature of a patient to a target site; actuating a delivery catheter actuator of the delivery catheter handle to proximally withdraw the delivery catheter; actuating a retrieval catheter actuator of the retrieval catheter handle to proximally withdraw a cover sheath connected to the retrieval catheter handle; disconnecting the delivery catheter handle and the retrieval catheter handle; and proximally withdrawing the delivery catheter through a retrieval catheter lumen of the retrieval catheter.

The details of one or more examples are set forth in the accompanying drawings and the description below. Other features, objects, and advantages will be apparent from the description and drawings, and from the claims.

BRIEF DESCRIPTION OF DRAWINGS

FIG. 1 is a conceptual side elevation view of an example thrombus-removal device.

FIGS. 2A and 2B are conceptual illustrations of a thrombus being separated into smaller pieces by arms of an expandable element of the thrombus-removal device of FIG. 1.

FIG. 4 is a conceptual side elevation view of another example thrombus-removal device.

FIG. 5 is a conceptual side elevation view of another example thrombus-removal device.

FIG. 6A is a conceptual side elevation view of another example thrombus-removal device.

FIG. 6B is a conceptual side elevation view of an example thrombus-removal device that includes an expandable element defining a stepped taper.

FIGS. 9A-9C are conceptual perspective views of example thrombus-removal devices including nonlinear arms.

FIG. 9D is an end view of the example thrombus-removal device of FIG. 9C.

FIGS. 12A and 12B illustrate example delivery catheters that define one or more openings through which a therapeutic agent may delivered to a target site within a patient.

DETAILED DESCRIPTION

Figure 2B:
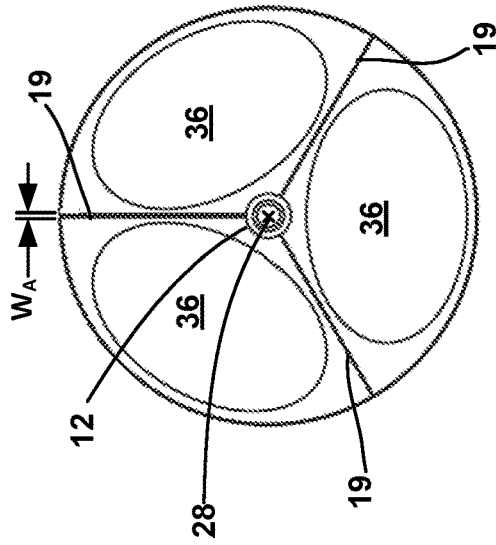

Thrombus-removal devices described herein (also referred to herein as thrombus-collection devices) are configured to remove occlusive material (e.g., a thrombus, an embolus, fatty deposits, and the like) from vasculature of a patient during an endovascular procedure or to remove occlusive material from other hollow anatomical structures of a patient. Example thrombus-removal devices described herein include an expandable element configured to capture occlusive material from the vasculature of a patient and segment the occlusive material into smaller pieces as the occlusive material moves into a basket defined by the expandable element. Segmenting the occlusive material into smaller pieces may help prevent larger pieces of the occlusive material from dislodging and moving downstream in the blood flow, which may create an embolism. While a thrombus and blood vessels/vasculature are primarily referred to throughout the remainder of the disclosure, it should be understood that the thrombus-removal devices and technique described herein can be used to collect and remove other types of occlusive material from a hollow anatomical structure of a patient.

Example thrombus-removal devices described herein include an elongated support member and an expandable element configured to expand radially outward from a delivery configuration to a deployed configuration. For example, the expandable element may be formed from a laser cut nitinol frame or another self-expandable frame. In the deployed configuration, the expandable element defines a proximal mouth configured to receive a thrombus and a distal basket configured to receive at least part of the thrombus after it has moved through the proximal mouth.

The distal basket has a closed end to retain the collected thrombus pieces. A proximal portion of the expandable element defines a plurality of arms configured to segment the thrombus into smaller pieces as the thrombus moves through the proximal mouth and into the basket. For example, the plurality of arms may be relatively rigid and configured to cut through the thrombus as the expandable element is moved proximally through the thrombus and as the thrombus is pushed past the arms and into the distal basket. The basket is configured to retain and hold these smaller pieces of the thrombus, thereby preventing at least part of the thrombus from moving downstream in the blood flow.

The expandable element may define any suitable number of arms, such as, but not limited to two arms to six arms, or about three arms. In addition, the expandable element may have any suitable length, such as, but not limited to, a length of about 50 millimeters (mm) to about 150 mm, measured from a proximal-most end of the expandable element (e.g., at a proximal end of the arms) to a distal-most end of the expandable element (e.g., at a distal end of the basket). In some examples, such as when used to describe numerical values, "about" or "approximately" refers to a range within the numerical value resulting from manufacturing tolerances and/or within 1%, 5%, or 10% of the numerical value. For example, a length of about 10 mm refers to a length of 10 mm to the extent permitted by manufacturing tolerances, or a length of 10 mm+/−0.1 mm, +/−0.5 mm, or +/−1 mm in various examples.

In some examples, in its deployed configuration, a proximal portion of the expandable element is configured to substantially conform (e.g., conform or nearly conform) to a shape of an inner wall of a blood vessel. When the expandable element is selected to be oversized relative to an intended blood vessel, the proximal portion of the expandable element is configured to be in apposition with a vessel wall. This configuration may help the proximal mouth of the expandable element stay open and, in some cases, centered in the vessel, as the expandable element is moved proximally through a thrombus, and may help enable a relatively large percentage of the thrombus to be collected in the distal basket of the expandable element. In some examples, the expandable member is also configured to self-center due at least in part to one or more of a radially symmetric design or being self-expandable. In some examples, the proximal mouth of the expandable element is configured to have an outward radial force greater than the radial force of the distal basket of the expandable element.

In addition, in some examples, when the expandable element is in its deployed configuration, the proximal mouth of the expandable element is configured to have an outward radial force greater than the radial force of the distal basket of the expandable element.

In some examples, in the deployed configuration, the expandable element tapers in a distal direction along a majority of a length of at least the distal portion of the expandable element, such as a long a majority of a length of the distal basket or along a major of length of the entire expandable element. The taper can be, for example, a constant taper, a stepped taper, or a gradual taper, and can define a conical-shaped distal basket. In some examples, the expandable element tapers from a diameter of about 20 mm at the proximal mouth to a diameter of 2 mm at the distal end. As a result of the tapering configuration, only a relatively small length of the expandable element is configured to contact the inner wall of the blood vessel when the expandable element is deployed within the blood vessel, which may help reduce adverse impact the expandable element has on the wall of the blood vessel as a clinician pulls the expandable element proximally through the blood vessel and through the clot.

In addition, due to the distal taper of the expandable element and the corresponding decrease in volume in the basket of the expandable element in the distal direction, the expandable element as configured compresses the thrombus positioned in the basket as the expandable element is proximally withdrawn into a retrieval catheter. Compressing the thrombus may expel water from the thrombus and dehydrate the thrombus, such that it decreases in volume in the basket, which may help aid retrieval of the thrombus-removal device with a relatively small profile catheter. The tapered shape of the expandable element may also help distribute the thrombus longitudinally within the basket as the expandable element is proximally withdrawn into a retrieval catheter, which may help mitigate the possibility of having too much relatively rigid material (e.g., the dehydrated thrombus) at the distal-most end of the basket. A relatively large bulk of relatively rigid material at the distal-most end of the basket may interfere with the proximal withdrawal of the thrombus-removal device into a retrieval catheter.

The distal basket of the expandable element defines a plurality of openings, e.g., a mesh, configured to enable fluid to flow through the distal basket while still retaining collected pieces of thrombus in the distal basket. In some examples, the size of the openings may be constant throughout the distal basket, while in other examples, the average size of the openings may decrease from a proximal end to a distal end of the basket to help prevent escape of collected thrombus during retrieval of the thrombus-removal device from a patient.

In some existing techniques, occlusive material lodged within a blood vessel of a patient may be removed by delivering a chemical substance (e.g., a lytic agent) or by aspirating the occlusive material from the blood vessel. While these techniques may be useful, they may also result in relatively large particulate debris breaking off from the thrombus, flowing downstream of the treatment site, and potentially restricting downstream blood flow. While a filter or other device may be used to try to capture the particulate debris, there may be design challenges to placing the filter for successful removal of the occlusive material while capturing any particulate debris from flowing downstream of the treatment site. In contrast to a more passive filter that may catch particulate in a blood stream, the thrombus-removal devices described herein are configured to more actively capture a thrombus, e.g., by segmenting the thrombus into smaller pieces and capturing the smaller pieces in a basket as a clinician moves an expandable element of the respective thrombus-removal device proximally through the thrombus.

Further, in contrast to systems that primarily rely on delivery of a chemical substance or the application of aspiration to a thrombus, the thrombus-removal devices described herein may require less capital equipment and may be less cumbersome to operate. For example, the thrombus-removal devices may be delivered to a treatment site within vasculature with the aid of a relatively straightforward catheter assembly (e.g., including a guidewire and a catheter) and may not require a separate vacuum device or therapeutic agent delivery device. In some examples, however, the thrombus-removal devices described herein may be used in combination with delivery of a chemical substance (e.g., a lytic agent) to a thrombus and/or aspiration of the thrombus.

The elongated support member of the thrombus-removal device may be used to deliver and control the position of the expandable element in the vasculature of the patient from a location outside of the patient. For example, the elongated support member may have the configuration of a guidewire or another elongated body. In some examples, the elongated support member extends through the expandable element from a proximal end of the expandable element to a distal end of the expandable element. In other examples, the elongated support member may not extend through the expandable element from a proximal end of the expandable element to a distal end of the expandable element, and may terminate at the proximal portion (e.g., at the proximal end) of the expandable element. In these examples, the distal portion of the expandable element may not be connected to any elongated element. That is, the distal portion of the expandable element is either mechanically connected to the elongated support member or is not mechanically connected to any elongated support member extending through the expandable element from a proximal end of the expandable element to a distal end of the expandable element. In any of these examples, however, a guidewire may be used with the thrombus-removal device and may extend through the expandable element during use of the thrombus-removal device.

In some examples, the distal portion of the expandable element is configured to move longitudinally relative to the elongated support member and move towards or away from the proximal portion of the expandable element. This may be useful for maintaining apposition of the proximal portion of the expandable element with a vessel wall, as well as accommodating the change in expandable element dimensions as a thrombus is collected in the basket defined by the distal portion of the expandable element and/or as the expandable element is proximally withdrawn into a catheter lumen. In other examples, the distal portion of the expandable element is fixed relative to the proximal end of the expandable element.

FIG. 1 is a side view of an example thrombus-removal device 10, which is configured to remove occlusive material within vasculature of a patient. Although FIG. 1, as well as many of the other figures are referred to herein as side views, in some cases, portions of the devices are removed to show, for example, an inner lumen or the like. Thus, the side views may also be referred to as conceptual cross-sectional views in some cases. The thrombus-removal device 10 can be used with any suitable treatment procedure. For example, the thrombus-removal device 10 can be used to remove a thrombus from within iliofemoral veins, central veins, upper extremity veins, peripheral large arteries, arteriovenous fistulae, or any other suitable target site within a patient.

The thrombus-removal device 10 includes an elongated support member 12 and an expandable element 14 disposed on the elongated support member 12. The elongated support member 12 is fixedly connected to expandable element 14 using any suitable technique. In some examples, the expandable element 14 may be connected to the elongated support member 12 by an adhesive, solder, welding, crimped elements, such as bands or beads, and other suitable fixation mechanisms and/or elements or combinations thereof. In other examples, the expandable element 14 may be formed directly onto the elongated support member 12, such as by incorporating one or more sections of the elongated support member 12 into a material forming the expandable element 14.

Elongated support member 12 provides a structure by which a clinician may control the expandable element 14. For example, a clinician may grasp and manipulate a proximal portion of the elongated support member 12 to deploy the expandable element 14 from a delivery catheter and directly into a blood vessel of a patient, to move the expandable element through a thrombus in the blood vessel, and to remove the expandable element 14 from the blood vessel. The elongated support member 12 may have any suitable length, such as, but not limited to, about 50 cm to about 100 cm, such as about 60 cm, about 75 cm, or about 90 cm (e.g., exactly these lengths or approximately these lengths to the extent permitted by manufacturing tolerances), and may be formed from any suitable material. For example, the elongated support member 12 may be formed from a metal, a polymer, or combinations thereof. Example materials for elongated support member 12 include, but are not limited to, nitinol (nickel titanium), stainless steel, cobalt-chromium-nickel molybdenum-iron alloy (e.g., commercially available under the trade designation Elgiloy™ available from Elgiloy Specialty Metals of Elgin, Illinois), carbon fiber and its composites, and engineered polymers such as liquid crystal polymers, polyether ether ketone (PEEK), polyamide, polyimide, polyester, and the like.

Elongated support member 12 is sufficiently flexible to enable thrombus-removal device 10 to be navigated through the vasculature, which may be relatively tortuous in some cases, without kinking or becoming arrested by the vasculature en route to the treatment site. Elongated support member 12 may be solid in some examples, or may be hollow over some or all of its length. For example, in the example shown in FIG. 1, the elongated support member 12 defines an inner lumen configured to receive a guidewire 15. During use of the thrombus-removal device 10 in a patient, the guidewire 15 may be extend along a full length of the elongated support member 12 or may extend only along a portion of the elongated support member 12, e.g., in a rapid exchange-type configuration, and may be used to aid delivery of the thrombus-removal device 10 to a treatment site within the vasculature of a patient.

Figure 3:
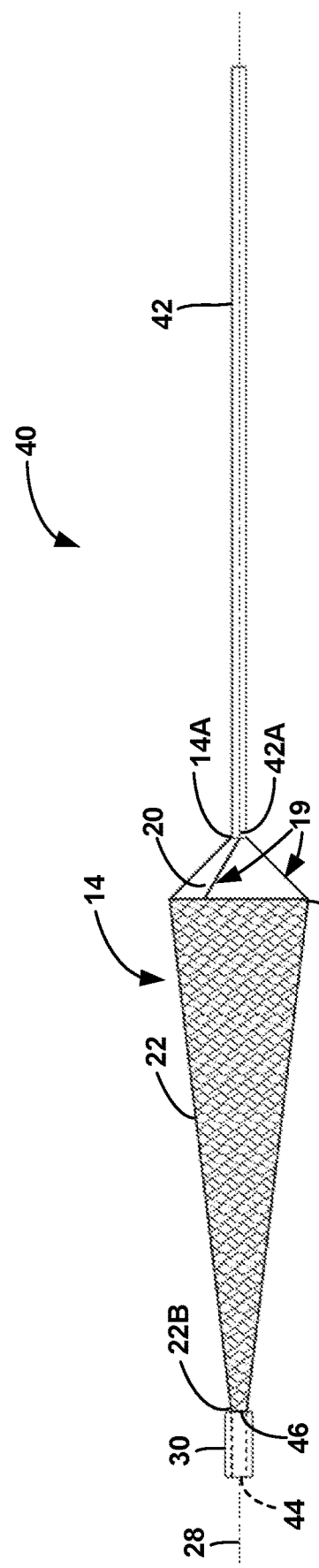
FIG. 3 is a conceptual side elevation view of another example thrombus-removal device.

The expandable element 14 includes an expandable element proximal portion 16 and an expandable element distal portion 18. The expandable element proximal portion 16 comprises a plurality of arms 19 extending from the expandable element 14 to the elongated support member 12. In some examples, as shown in FIG. 1, the elongated support member 12 extends entirely through the expandable element 14 from a proximal end 14A of the expandable element to a distal end 14B of the expandable element 14. In other examples, as shown in FIG. 3, the elongated support member 12 may not extend entirely through the expandable element 14 and may instead terminate at the proximal portion 16 (e.g., at a proximal end 14A) of the expandable element 14. That is, the elongated support member 12 may end at, or end substantially near, a point where the elongated support member 12 is mechanically connected to the expandable element proximal portion 16. In these examples, the distal portion 18 of the expandable element 14 may not be connected to any elongated support member. That is, the distal portion 18 of the expandable element 14 is either mechanically connected to the elongated support member 12 or is not mechanically connected to any elongated support member extending through the expandable element 14 from the proximal end 14A to the distal end 14B.

In some examples, the expandable element distal portion 18 is configured to move longitudinally relative to the expandable element proximal portion 16 and, in some examples, relative to the elongated support member 12. That is, the expandable element 14 can be connected to the elongated support member 12 such that the expandable element distal portion 18 is configured to move towards or away from the expandable element proximal portion 16. For example, the expandable element distal portion 18 may not be connected to the elongated support member 12 and may move relative to the proximal end 14A of the expandable element 14 in at least a longitudinal direction. This may enable the expandable element proximal portion 16 to maintain apposition with a vessel wall, as well as enable the expandable element 14 to change shape as a thrombus is collected in a basket defined by expandable element distal portion 18 or as the expandable element 14 is withdrawn into a catheter. For example, when the expandable element distal portion 18 moves relative to the proximal end of the elongated support member 12, the expandable element 14 may elongate or constrict in the longitudinal direction and/or expand in a radially outward direction.

In some examples in which the elongated support member 12 extends through the expandable element 14 and in which the expandable element distal portion 18 is movably connected to the elongated support member 12, the expandable element distal portion 18 is configured to move towards or away from the expandable element proximal portion 16. For example, the expandable element distal portion 18 can be fixedly connected to a distal slider 32. The distal slider 32 is configured to move relative to the expandable element proximal portion 16, such as by sliding along an outer surface of the elongated support member 12. In some examples, the distal slider 32 has a tubular body or a partial-ring shape that fits around the outer surface of the elongated support member 12.

In some examples in which the expandable element distal portion 18 is movable relative to the proximal end 14A of the expandable element 14, the elongated support member 12 may include at least one mechanical stop that limits the relative proximal and distal sliding of the distal end 14B of the expandable element 14 relative to the proximal end 14A. The ability of expandable element distal end 14B to move relative to the expandable element proximal end 14A and relative to the elongated support member 12 may enable the expandable element 14 to conform to the inner wall of the peripheral vasculature while the elongated support member 12 is moving through the thrombus, during deployment, or retrieval of the elongated support member 12. For example, a clinician slides the expandable element distal portion 18 proximally relative to the proximal end 14A of the expandable element 14 so that the expandable element 14 more closely adheres to the inner wall of a blood vessel.

In other examples, the expandable element distal portion 18 is fixed relative to the proximal end 14A of the expandable element 14. For example, the expandable element distal portion 18 may be fixed to the elongated support member 12, such as by welding, adhesive, a mechanical connection, e.g., crimping a part of the expandable element distal portion 18 to the elongated support member 12.

The expandable element 14 is configured to expand radially outward from a relatively low profile (e.g., relatively small radial profile) delivery configuration to an expanded deployed configuration. In some examples, the expandable element 14 is configured to self-expand from the delivery configuration to the deployed configuration, e.g., in response to being released from an inner lumen of a delivery catheter. The compressive force applied to the expandable element 14 by the delivery catheter when the expandable element 14 is in the inner lumen may help hold the expandable element 14 in the delivery configuration. When the expandable element 14 is deployed from the inner lumen of the delivery catheter, the expandable element 14 may self-expand radially outward into its deployed configuration. In self-expanding examples, the expandable element 14 may be formed from any suitable material, such as, but not limited to, nitinol. For example, the expandable element 14 may be formed from a cut (e.g., a laser-cut) nitinol tube, e.g., similar to a stent, or from a nitinol mesh. A nitinol structure can be heat-set to assume a desired shape upon deployment within a patient.

In other examples, however, the expandable element 14 is not configured to self-expand and instead may be expanded with the aid of an expansion mechanism, such as, but not limited to, a balloon positioned inside an interior space of the expandable element 14. In these examples, the expandable element 14 may be formed from any suitable material, such as, but not limited to, stainless steel or a polymeric material.

The expandable element 14 may be configured to assume a delivery configuration that enables the expandable element 14 to be delivered to a target site within vasculature of a patient using a relatively small profile delivery catheter, such as, but not limited to, an 8 French (Fr) catheter to a 12 Fr catheter, or another catheter having an outer diameter of less than or equal to about 4 mm. A relatively small profile delivery catheter may permit the catheter to pass distally through a thrombus to deploy the expandable element 14 on a distal side of the thrombus without creating large thrombus debris during the movement distally through the thrombus. As discussed below, a clinician may deploy the expandable element 14 from the delivery catheter on the distal side of the thrombus and withdraw the expandable element 14 proximally through the thrombus to capture at least part of the thrombus in the expandable element 14. In addition, relatively small profile delivery catheter may reduce interaction between the delivery catheter and one or more other medical devices implanted in the vasculature of the patient, such as an inferior vena cava (IVC) filter.

In the deployed configuration, the expandable element proximal portion 16 defines a proximal mouth 20 configured to receive a thrombus and the expandable element distal portion 18 defines a distal basket 22 configured to receive at least part of the thrombus after it has moved through the proximal mouth 20. The mouth 20 may also be referred to as a proximal facing mouth in some examples because it provides an opening to the expandable element 14 in the proximal direction. In some examples, the proximal mouth 20 may comprise a section of the expandable element proximal portion 16 beginning at the point of the maximum radial circumference and ending at roughly a point where the plurality of arms 19 mechanically connect to the elongated support member 12. The distal basket 22 has a closed end configured to retain at least part of the collected thrombus pieces.

Regardless of whether the expandable element 14 is configured to self-expand, the expandable element 14 may be formed from any material that is suitably flexible and resilient to enable expandable element proximal portion 16 to substantially conform to (e.g., conform or nearly conform to) a wall of a blood vessel when the expandable element 14 is deployed within the blood vessel. As discussed in further detail below, substantially conforming expandable element proximal portion 16 to the wall of a blood vessel may better enable expandable element 14 to capture thrombi (e.g., pieces of a larger thrombus within the blood vessel) by increasing a size of the proximal mouth 20 through which the thrombi may enter the basket 22. In some examples, a maximum cross-sectional dimension (e.g., a maximum diameter) of the proximal mouth 20 may be roughly the same point as the maximum cross-sectional dimension $D_1$ of the expandable element 14.

The maximum cross-sectional dimension $D_1$ of the expandable element 14 in its deployed state, when unconstrained by a catheter lumen, a body lumen, or the like, may be selected based on the body lumen in which the thrombus-removal device 10 is intended to be used. For example, the maximum outer cross-sectional dimension $D_1$ of the expandable element 14 may be selected to be oversized relative to the body lumen, e.g., by 5% to 25%, such as about 10%, in order to enable the expandable element proximal portion 16 to be in apposition to the wall of the body lumen when the device 10 is deployed in the body lumen. The apposition between the proximal portion 16 (including the proximal mouth 20) and a blood vessel wall may help the thrombus-removal device 10 collect a larger percentage of the thrombus. In some examples, the maximum cross-sectional dimension $D_1$ is 20 mm, while the maximum cross-sectional dimension $D_2$ at the distal end 14B of the expandable element 14 is 2 mm. The example dimensions described herein for the thrombus-removal device 10 are not exhaustive. The expandable element 14 having any suitable diameter may be employed and may be sized for deployment into the vasculature of any suitable subject.

The expandable element 14 may have any suitable length, which can be measured from the proximal end 14A to the distal end 14B along a central longitudinal axis 28 of the elongated support member 12. In some examples, the expandable element 14 has a length of about 50 mm to about 150 mm. In some examples, the length is selected to facilitate a particular anatomical location. For example, the expandable element 14 can have a length that enables the proximal end 14A of the expandable element 14 to be positioned at the base of the interior vena cava while keeping the distal end 14B out of the right atrium. For example, the expandable element 14 can have a length of less than or equal to about 150 mm.

The elongated support member 12 is positioned generally along the longitudinal axis 28, which extends from the proximal end 14a of the expandable element 14 to the distal end 14B of the expandable element 14.

The expandable element 14 defines a plurality of openings 24 of uniform or various nonuniform dimensions. For example, the expandable element 14 may be formed from a mesh or braided structure, or a cut (e.g., a laser cut) tube. The plurality of openings 24 may be formed by mechanical means such as laser cut, drilling, and punching, by chemical means such as the selective dissolution of one or more components, or by virtue of a braided structure. Other examples of suitable materials for expandable element 14 may also include braided, knitted, woven, or non-woven fabrics that are capable of retaining particulate debris while permitting fluid to flow through the expandable element 14.

Other suitable configurations for the expandable element 14 includes a laser cut frame, such as a laser cut nitinol frame. In some cases, the expandable element 14 may be used multiple times for the same patient (e.g., for multiple passes of the same thrombus or different passes of different thrombus), and cleaned between passes. A laser cut frame may include fewer crossing points than a braided expandable element, which may make cleaning the expandable element 14 to remove any captured thrombus easier. Crossing points between filaments of a braid or other structure may trap parts of the thrombus and, thus, make cleaning of the expandable element 14 more difficult and time consuming. A laser cut frame may have fewer crossing points than a braid. Further, a braid may be more likely to elongate and decrease in diameter during cleaning compared to a laser cut tube (e.g., as the expandable element 14 is cleaned in saline or wiped to remove thrombus fragments). The decrease in the diameter of a braided expandable element may also make removing the thrombus fragments from the expandable element 14 during cleaning more difficult compared to a laser cut tube.

In some examples, the expandable element 14 may be comprise a uniform material from the distal end to the proximal end. For example, the expandable element distal portion 18 may comprise the same suitable material (e.g., Nitinol) as the expandable element proximal portion 16. In some examples, the expandable element distal portion 18 may be formed from a different material composition than the expandable element proximal portion 16.

In some examples, the expandable element 14 has a configuration that facilitates the withdrawal of the expandable element 14 into a sheath, e.g., to remove the expandable element 14 from the vasculature or to reposition the expandable element 14 within the vasculature. For example, the expandable element 14 may be formed to be seamless (e.g., laser cut tube) and have closed cells. Seams or parts of an expandable element defining an open cell may catch on the distal end of a sheath during the resheathing process. Thus, eliminating seams and/or open cells may help facilitate easier resheathing of the expandable element.

In some examples, the plurality of openings 24 having an average maximum cross-sectional dimension of 1 mm to about 10 mm. The size of the openings can depend on the vessel diameter to which the device 10 is apposed. In some examples, when the device 10 is configured to be expanded and in apposition to a vessel having a 16 mm diameter, openings 24 have an average maximum cross-sectional dimension of about 4 mm to about 8 mm when the expandable element 14 is in the expanded, deployed configuration, the maximum cross-sectional dimension being measured across the respective opening around the circumference (or other outer perimeter in the case of non-circular expandable elements 14) of the expandable element 14 at a given cross section of the overall device 10.

In some examples, the shape of the openings 24 may dynamically change depending on a combination of any pressure applied from any foreign substance, such as a thrombus or other occlusive matter, and a material composition of the expandable element distal portion 18. For example, as the expandable element 14 is in the delivery configuration moving distally through a thrombus, the cross-sectional openings may be at a minimum dimension and, as the expandable element 14 is in the deployed configuration moving proximally through the thrombus, the openings 24 may increase in size.

The basket 22 of the expandable element 14 defines an interior cavity 26 configured to receive and retain pieces of a thrombus via the proximal mouth 20. The plurality of openings 24 are present in the portion of the expandable element 14 defining the basket 22. Thus, when the expandable element 14 is in its deployed configuration within a blood vessel lumen, fluid (e.g., fluid) can flow through the expandable element 14 past thrombus captured inside the interior cavity 26 of the basket 22. In some examples, the size of the openings 24 are constant throughout distal basket 22, while in other examples, the average size of the openings vary throughout the basket 22. For example, the average size of the openings may decrease from a proximal end to a distal end of the basket 22 to help prevent escape of collected thrombus from the basket 22 during retrieval of the thrombus-removal device 10 from a patient.

In the deployed configuration of the thrombus-removal device 10, an outer surface of at least the expandable element distal portion 18 tapers in a distal direction along a majority of the length of the expandable element distal portion 18. For example, the expandable element 14 can taper in a distal direction along a majority of the length of the expandable element 14. This taper may define a conical shaped basket 22, as shown in FIG. 1.

In some examples, the expandable element tapers from a diameter of about 20 mm at the proximal mouth to a diameter of 2 mm at the distal end. In some examples, the expandable element 14 may define a constant taper in the distal direction, as shown in FIG. 1. In other examples, the expandable element 14 defines a stepped taper or a gradual taper in the distal direction, as described with respect to FIGS. 6 and 7. The stepped taper may be achieved using any combination of geometries, such as, but not limited to, a proximal cylindrical segment followed by a proximal frustoconical segment, which can, in some cases, followed by a distal cylindrical segment and a distal frustoconical segment. The gradual taper may be achieved using any combination of geometries, such as, but not limited to, a proximal frustoconical segment, followed by one or more additional frustoconical segments, at least two of the frustoconical segments having different degrees of taper. The taper segments (e.g., the frustoconical segments) may be any angle (e.g., 10 degrees to 80 degrees) relative to a longitudinal axis of the elongated support member 12.

As a result of the tapering configuration, only a relatively small length $L_C$ (shown in FIG. 11B) of the expandable element proximal portion 16 is configured to contact an inner wall of the blood vessel when the expandable element 14 is deployed within the blood vessel. This may enable the expandable element 14 to both achieve some apposition with the blood vessel wall to capture more thrombus, while reducing the adverse interaction between the expandable element 14 and the wall of the blood vessel as a clinician pulls the expandable element 14 proximally through the blood vessel and through the thrombus. Overly contacting the vessel wall may lead to vessel spasms and adverse impacts to the inner layer of the vessel, which may lead to further thrombosis. In some examples, the length $L_C$ of the contact between the expandable element 14 and the vessel wall when the thrombus-removal device 10 is deployed in the vessel is about 5 mm to about 50 mm, such as about 5 mm, 10 mm, or 50 mm. The length $L_C$ of the contact between the expandable element 14 and the vessel wall may increase with smaller diameter vessels as the largest diameter (or other cross-sectional dimension) expandable element proximal portion 16 will be compressed.

In some examples, the proximal length $L_C$ (shown in FIG. 11B) of the expandable element proximal portion 16 is configured to have an outward radial force greater than the radial force of the distal basket 22 of the expandable element 14 to help ensure apposition to the vessel wall. The distal basket 22 may be configured to exert less radial force, even if it contacts the vessel wall. As an example, the expandable element proximal portion 16 may have an outward radial force greater than the radial force of the expandable element distal portion 18. In addition, the greater radial force may not only help ensure greater apposition with a vessel wall, but may also facilitate disruption of a thrombus. The greater radial force may be achieved using any suitable technique, such as, but not limited to, including a proximal ring 38 (as shown with in FIG. 4) that is configured to expand radially outward, e.g., in response to being released from an inner lumen of a delivery catheter.

A thrombus may not be uniformly distributed within a blood vessel. Rather than relying on a clinician to guide the expandable element 14 to the side of the vessel wall that has the largest volume of the thrombus, the apposition of the portion of the expandable element proximal portion 16 defining the proximal mouth 20 and the blood vessel wall may help center the expandable element 14 in the vessel to capture a larger volume of thrombus. In some examples, the expandable element 14 is configured to self-center in the vessel due at least in part to the proximal portion of the expandable element 14 being configured to stay in apposition with the vessel wall and/or being radially symmetric about longitudinal axis 28. This may enable the expandable element 14 to stay open and conform to vessel curvature when used with many clot types (e.g., which may have different densities) improving wall to wall contact.

Further, having only a relatively small length of the expandable element proximal portion 16 configured to contact an inner wall of the blood vessel may enable the expandable element 14 to product less drag force (i.e., less force needed to be exerted by the clinician) to move the device 10 through the vessel.

In some examples, a proximal part of the expandable element 14, e.g., the expandable element proximal portion 16 and/or the proximal mouth 20, which may correspond to about the first 5 mm to about 20 mm of the expandable element 14, is configured to have more radial force to help ensure apposition to the vessel wall when the expandable element 14 is in the deployed configuration in the blood vessel. In some of these examples, the remaining distal length of the device 10 is configured to exert less radial force than the proximal part to enable the remaining distal length pass more passively through the vessel.

At least in part due to the tapered configuration of the expandable element 14 and the corresponding decrease in volume of the basket 22, the expandable element 14 is configured to compress at least a part of the thrombus received within the basket 22 as the expandable element 14 is proximally withdrawn into a catheter. A thrombus may have a relatively large liquid content. Thus, by compressing the thrombus, fluid may be expelled from the thrombus and dehydrate the thrombus, such that the volume of the thrombus retained in the basket 22 is decreased. Decreasing the volume of the thrombus in the basket 22 may help increase the ease with which the expandable element 14 may be withdrawn proximally into the inner lumen of a catheter to withdraw the thrombus from the patient.

The tapered shape of the expandable element 14 may help distribute the thrombus longitudinally within the basket 22 as the expandable element 14 is proximally withdrawn into a catheter, which may help mitigate the possibility of having too much relatively rigid material (e.g., the dehydrated thrombus) at the distal-most end of the basket 22. A relatively large bulk of relatively rigid material at the distal-most end of the basket 22 may interfere with the proximal withdrawal of the expandable element 14 into a retrieval catheter. For example, while moving the expandable element 14 proximally through the thrombus, the thrombus may be segmented by the plurality of arms 19, captured within the basket 22, and then compressed within the expandable element 14 as the thrombus is forced towards the distal end 14B of the expandable element 14. As noted above, this compression may expel liquid within the thrombus as the expandable element 14 elongates while the elongated support member 12 moves proximally through a blood vessel.

The distribution of the thrombus longitudinally within the basket 22, as well as the compression of the thrombus within the basket 22 may help expandable element 14 retain and remove a relatively large thrombus from a blood vessel of a patient for a given expandable element 14 size.

As discussed above, the expandable element 14 includes a plurality of arms 19 extending from the expandable element proximal portion 16 to the elongated support member 12. The plurality of arms 19 are configured to separate a thrombus into a plurality of pieces (e.g., two or more smaller pieces) as the expandable element 14 is moved proximally through the thrombus and as the thrombus enters proximal mouth 20 and is captured within the basket 22. For example, the arms 19 may collectively be wide enough (arm width $W_A$ is shown in FIG. 2B) to separate a thrombus into smaller pieces without blocking entry into the basket 22 via the proximal mouth 20. The arms 19 may be configured to the area of occlusion of the proximal mouth 20 to well under 10% of the cross-sectional area of the proximal mouth 20 (the cross-section being taken in a direction orthogonal to the longitudinal axis 28) and enables the arms 19 to separate the thrombus with minimal force and does not impede the thrombus pieces from entering the mouth 20. In some examples, the plurality of arms 19 include three arms with a width $W_A$ (measured in the circumferential direction, as shown in FIG. 2B) of about 0.25 mm an angle of about 45 degrees with respect to the longitudinal axis 28 of the elongated member 12.

Minimizing the area of contact between the thrombus and the arms 19 may facilitate the shearing process of the arms 19 as they pass through and separate the thrombus. FIGS. 2A and 2B are conceptual illustrations of the plurality of arms 19 separating a thrombus into a plurality of smaller thrombus pieces 36. FIG. 2A is a conceptual side elevation view of the thrombus 36 entering the proximal mouth 20 of the expandable element 14, and FIG. 2B is an end view of the expandable element 14, looking along the longitudinal axis 28 of the elongated support member 12, and illustrates the thrombus pieces 36 after they have been separated from a larger thrombus 34 and as they are entering the distal basket 22. Also shown in FIG. 2A is a delivery catheter 102, a retrieval catheter 104 defining or otherwise including a funnel 106, and a cover sheath 108, which are described in further detail below with reference to FIG. 10. The entire length of the catheters 102, 104, and the cover sheath 108 may not be shown in the figures. For example, the retrieval catheter 104 shown in FIG. 2A is shown to be relatively short, but may in use have a length long enough to extend from a target site within a patient to a location outside of the patient.

As the arms 19 shear through the thrombus 34, the arms 19 push outward onto the thrombus 34 and an equal and opposite reaction force from the thrombus 34 pushes back onto the arms, as conceptually illustrated via the arrows in FIG. 2A. Wider arms 19 require greater force to push through the thrombus 34, which in turn necessitates more radial force in the mouth 20 in order to resist the compressive reaction force from the thrombus 34 and stay open. Thus, it may be desirable in some examples to select the size of the arms 19 to provide a radially outward force of the expandable element 14 on a vessel wall, while still enabling the radially outward force to be small enough to enable a clinician to proximally pull the expandable element through the vessel wall, as well as to decrease the force required to pull the expandable element 14 proximally through the thrombus 34 may be desired in some examples.

Separating the thrombus 34 into a plurality of pieces 36 may enable more effective capture of the thrombus within the basket 22, particularly when the thrombus may be a sub-acute thrombus that is more organized and/or wall-adherent compared to a more newly formed acute thrombus, which may be softer. In addition, separating the thrombus 34 into a plurality of pieces 36 may enable a smaller delivery and/or retrieval catheter to be used to deliver or withdraw, respectively, the thrombus-removal device 10 from the patient.

The plurality of arms 19 may include any suitable number of arms. For example, the plurality of arms 19 may include as few as two arms or as many as six arms, such as about three arms, four arms, or five arms. In addition, the arms 19 may have any suitable radial spacing, e.g., be evenly distributed around central longitudinal axis 28 (e.g., for three arms 19, the arms may be 120 degrees apart from each other) or may be unevenly distributed around central longitudinal axis 28. The number of arms 19 and the radial spacing between the arms 19 may be selected to enable the proximal mouth 20 to remain relatively open, centered around the elongated support member 12, and to enable pieces of thrombus to move distally into basket 22 rather than being captured and retained within the spaces between arms 19. In addition, the number of arms 19 may be selected to enable the thrombus 34 moving through the proximal mouth 20 to be segmented into sufficiently small pieces 36 for collection in the basket 22.

In some examples, some or all of the plurality of arms 19 may be integrally formed with the expandable element proximal portion 16. For example, the plurality of arms 19 may be struts of a tapered stent-like structure defining expandable proximal portion 16. In other examples, some or all of the arms 19 may be formed separate from the expandable element 14 and may be connected to the expandable element proximal portion 16 using any suitable technique, such as, but not limited to, the plurality of arms 19 may be connected to expandable element 14 by adhesives, solder, welding, crimped elements, such as bands or beads, and other suitable fixation mechanisms and/or elements. In these examples, the plurality of arms 19 may be formed from the same material or substantially the same material as the expandable element 14.

In addition, the arms 19 may be formed separate from or may be integrally formed with the elongated support member 12. In examples in which the plurality of arms 19 are formed separate from the elongated support member 12, the proximal ends of each arm 19 may be connected to the elongated support member 12 using any suitable technique, such as by an adhesive, solder, welding, crimped elements, such as bands or beads, and other suitable fixation mechanisms and/or elements.

The plurality of arms 19 define an angle α (FIG. 1) with respect to the longitudinal axis 28 of the elongated support member 12. The angle may be that of a point where the plurality of arms 19 is connected to the elongated support member 12. The arms 19 may have any suitable angle α relative to the longitudinal axis 28, such as, but not limited to, about 30 degrees to about 60 degrees relative to the longitudinal axis 28, or about 30 degrees, 45 degrees, or 60 degrees relative to the longitudinal axis 28. Some considerations for the angle include, for example, the total length of each arm (measured from proximal end to distal end of the respective arm), the maximum cross-sectional dimension of the proximal mouth 20, the column strength to enable deployment of the expandable element 14 into its expanded configuration, a flexibility and robustness of the arms 19 when passing through tortuosity, minimizing a force required to pass through the thrombus 34, and the area of the thinner arms that may contact the vessel wall or vein valves when passing through tortuosity.

Once the expandable element 14 is in a position distal to a thrombus, and deployed from delivery catheter, a clinician may move the elongated support member 12, and as a result, the fixedly connected expandable element 14 (in its deployed configuration) proximally through the thrombus. While moving the expandable element 14 proximally through the thrombus, the proximal mouth 20 will come in contact with the distal portion of a thrombus and segment the thrombus into smaller pieces, at least some of which are received in the proximal mouth 20, e.g., through spaces between adjacent arms 19. For example, the plurality of arms 19 may cut into the thrombus as the expandable element 14 is moving proximally through the thrombus. As the proximal mouth 20 receives the thrombus, the thrombus will move distally within the expandable element 14 towards the basket 22, where the thrombus may be retained.

In some examples, one or more disassociated segments of the thrombus may become entangled within the one or more openings 24 defined by the expandable element 14. For example, as the part of the thrombus within the basket 22 becomes compressed, some of the thrombus may be squeezed out one or more openings 24. However, even these parts of the thrombus extending through the one or more openings may still be considered captured within the basket 22. For example, the more rigid dehydrated thrombus extending through the opening 24 may be less likely to separate from the expandable element 14 and flow downstream.

In some examples, the thrombus-removal device 10 can include an atraumatic distal tip that is configured to soften an interface between the distal tip and adjacent tissue of a patient. For example, as shown in FIG. 1, the thrombus-removal device 10 can include a distal tip member 30 at or near a distal end of the elongated support member 12. The distal tip member 30 can be formed from any suitable material, such as, but not limited to, a relatively soft polymer that is softer than the material forming the elongated support member 12. In some examples, the distal tip member 30 may also act as the distal slider 32, which is configured to movably connect the distal end 14B of the expandable element 14 to the elongated support member 12 and is configured to slide relative to the elongated support member 12.

The configuration (e.g., shape, dimensions, and the like) and the composition (e.g., material) of the thrombus-removal device 10, including the expandable element 14 and the proximal mouth 20, of the examples described herein are merely one example. In other examples, for example, the expandable element 14 may have another shape or configuration and/or the elongated support member 12 may have another configuration.

For example, as discussed above, in some examples, the elongated support member 12 does not extend through the expandable element 14, and instead can terminate at or near the proximal end 14A of the expandable element 14. FIG. 3 is a side elevation view of such an example thrombus-removal device 40. The thrombus-removal device 40 is similar to the thrombus-removal device 10 and like-elements will not be described again with respect to FIG. 3. In contrast to the thrombus-removal device 10, the thrombus-removal device 40 includes an elongated support member 42 that terminates at a proximal end 14A of the expandable element 14. Thus, the proximal mouth 20 is positioned distal to the distal end 42A of the elongated support member 42 and the arms 19 extend from the distal end 42A of the elongated support member 42 to a proximal end 22A of the distal basket 22.

In examples in which the thrombus-removal device 40 include an atraumatic distal tip member 30, the distal tip member 30 can be positioned at a distal end 22B of the basket 22. The distal tip member 30, if present, can define a lumen 44 through which the guidewire 15 (FIG. 1) may extend from an inner lumen of the elongated support member 42 and through the expandable element 14. Similarly, the distal end 14B of the expandable element can define an opening 46 configured to receive the guidewire 15. The opening 46, can be sized to permit the guidewire 15 to slide within the opening 46, but small enough to minimize or even prevent pieces of thrombus within the basket 22 from leaving the basket 22 through the opening 46, e.g., around the guidewire 15 or in the absence of the guidewire 15.

The expandable element of a thrombus-removal device may have any suitable configuration of arms 19. For example, as shown in FIG. 4, an example thrombus-removal device 50 includes a plurality of arms 52 that are longer in length than the arms 19 of the thrombus-removal device 10 shown in FIG. 1. FIG. 4 also illustrates an example device 50 that includes a proximal ring 38 at a proximal end 22A of the basket 22. In some examples, the proximal ring 38 defines the greatest cross-sectional dimension of the expandable element 14 when the expandable element is in its deployed configuration (and unconstrained by any outward element, such as a catheter or vessel wall). The proximal ring 38 can have any suitable length (measured along the longitudinal axis 28), such as the lengths $L_C$ discussed below with reference to FIG. 11B. Although the proximal ring 38 is shown in FIG. 4, it can be used in combination with any of the other examples described herein. Indeed, any configuration of thrombus-removal devices described herein can be used alone or in combination with each other.

FIG. 5 illustrates an example thrombus-removal device 60 that includes a plurality of arms 62 that are shorter than the arms 19 of the thrombus-removal device 10 shown in FIG. 1. The length of the arms 52, 62 may be measured from a proximal end of the arm to a distal end of the respective arm along a longitudinal axis of the arm.

The thrombus-removal device 50 shown in FIG. 4 includes three arms and the thrombus-removal device 60 shown in FIG. 5 includes four arms 62. In other examples, however, the thrombus-removal devices 50, 60, as well as the other thrombus-removal devices herein, may have any suitable number of arms. The other structures of the thrombus-removal devices 50, 60 are similar to the thrombus-removal device 10 and are not specifically discussed herein for brevity.

As discussed above, the expandable element of a thrombus-removal device may have any suitable shape that tapers along a majority of a length of at least a distal portion of the expandable element.

FIG. 6A is a side elevation view of an example thrombus-removal device 70 that includes the elongated support member 12 and an expandable element 72 defining a taper. The expandable element 72 is an example of the expandable element 14 of FIG. 1. The other structures of the thrombus-removal device 70 are similar to the thrombus-removal device 10 and are not specifically discussed herein for brevity.

Figure 6C:
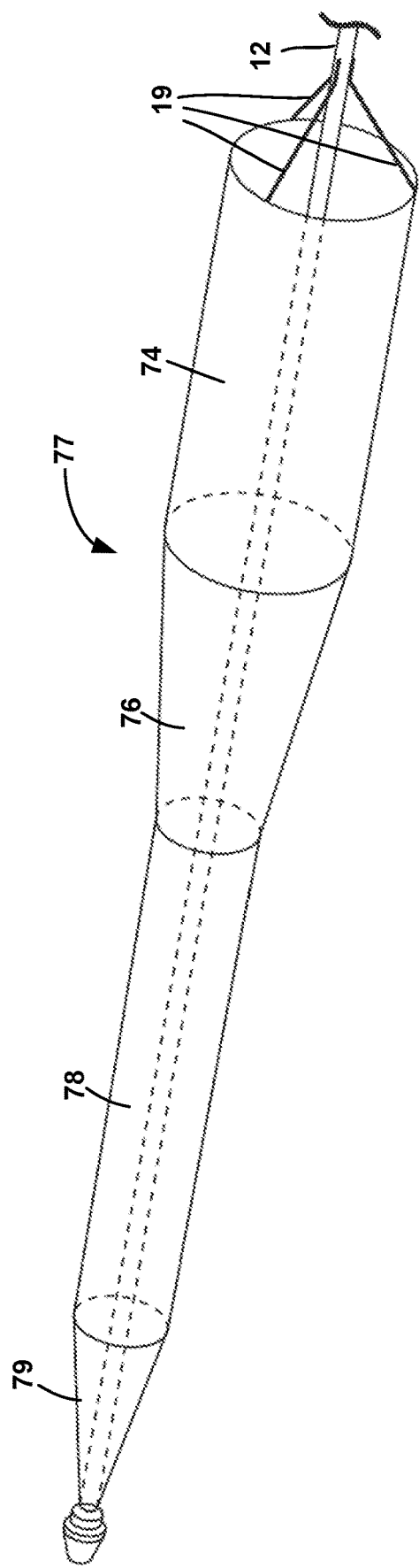
FIG. 6C is a conceptual perspective view of the expandable element of FIG. 6B.

The expandable element 72 comprises a proximal cylindrical segment 74 proximal to a distal frustoconical segment 76. The expandable element 72 can comprise any number of alternating cylindrical segments and frustoconical segments that define a distally tapering expandable element 72. The additional cylindrical segments and frustoconical segments can define an expandable element having a stepped taper. For example, FIG. 6B is a conceptual side elevation view of an example expandable element 77 defining a stepped taper, and FIG. 6C is a perspective view of the example expandable element 77. The expandable element 77 includes a second cylindrical segment 78 positioned distal to the frustoconical segment 76 and another frustoconical segment 79 positioned distal to the second cylindrical segment 78.

Figure 7:
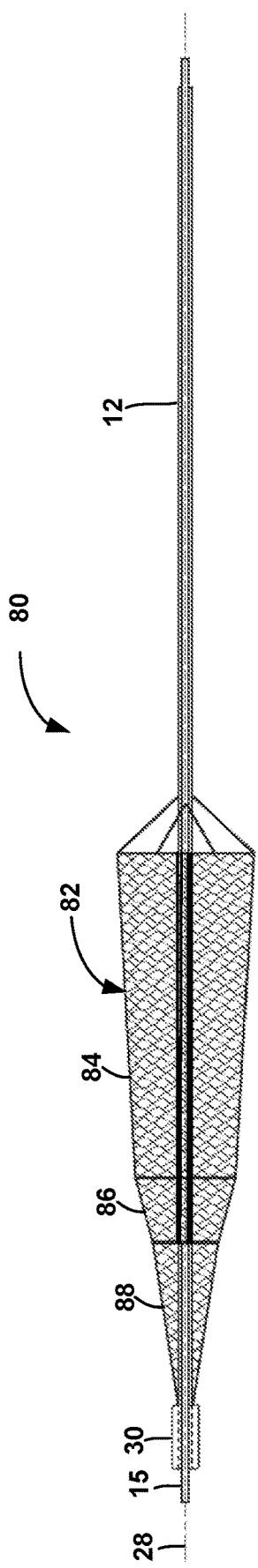
FIG. 7 is a conceptual side elevation view of another example thrombus-removal device.

FIG. 7 is a side elevation view of an example thrombus-removal device 80 that includes the elongated support member 12 and an expandable element 82 defining an example varying gradual taper. The expandable element 82 is an example of the expandable element 14 of FIG. 1. The expandable element 82 comprises a proximal frustoconical segment 84 proximal to an intermediate frustoconical segment 86, which is proximal to a distal frustoconical segment 88. At least two of the frustoconical segments 84, 86, 88 define different degrees of taper, e.g., as defined by the angle between the outermost surface of the respective segment and longitudinal axis 28. The expandable element 82 can comprise any number of frustoconical segments.

Figure 8:
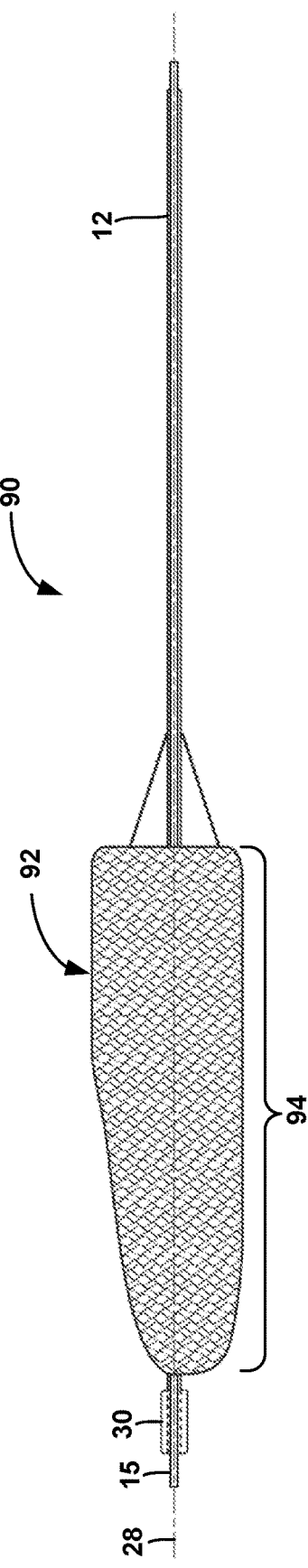
FIG. 8 is a conceptual side elevation view of another example thrombus-removal device.

FIG. 8 is a side elevation view of an example thrombus-removal device 90 that includes the elongated support member 12 and an expandable element 92 that tapers in a distal direction. The expandable element 92 is an example of the expandable element 14 of FIG. 1. The expandable element 92 does not specifically define a gradual taper, a stepped taper, or a continuous taper, but is nevertheless tapered along a majority of a length of a distal portion 94 of the expandable element 92 and, in some examples, along a majority of a length of the expandable element 92.

The shape of the expandable elements 72, 82, 92 shown in FIGS. 6-8 may be used with any of the configurations of thrombus-removal devices described above. For example, although FIGS. 6-8 illustrate the elongated support member 12 extending through the respective expandable elements 72, 82, 92, in other examples, the elongated support member 12 does not extend through the expandable element 72, 82, 92 and may instead terminate, e.g., at the proximal end of the expandable element 72, 82, 92.

Although example expandable elements including linear (straight) arms 19, 52, 62 are shown in FIGS. 1-8, in some examples, some or all of the arms of an expandable element may be nonlinear, such as bent or curved, between the respective proximal and distal ends. FIGS. 9A-9D are conceptual perspective views of example thrombus-removal devices including nonlinear arms.

FIG. 9A illustrates an example thrombus-removal device 96 that includes an expandable element 97, which is an example of the expandable element 14 of FIG. 1. A distal portion of the expandable element 97 defines a basket having a closed distal end and configured to receive at least part of the thrombus after it has moved through a proximal mouth of the basket. In particular, the distal portion of the expandable element 97 includes a proximal cylindrical segment 97A proximal to an intermediate frustoconical segment 97B, which is proximal to a tapered distal segment 97C. The details of the openings in the basket are not shown in FIG. 9A.

In addition, a proximal portion of the expandable element 97 includes a plurality of curved arms 98, which are similar to arms 19, 52, 62 discussed above, but are curved radially outward away from a central longitudinal axis 99 of the thrombus-removal device 96. Each of the arms 98 is curved between the respective proximal end 98A and the respective distal end 98B. Arms 98 that are curved radially outward away from the central longitudinal axis 99 may help hold the expandable element 97 in an expanded state when the thrombus-removal device 96 is pulled proximally through a thrombus, such as by applying a radially outward biasing force to the proximal portion of the expandable element 97.

FIG. 9B is a perspective view of another example thrombus-removal device 48 that includes an expandable element 54, which is an example of the expandable element 14 of FIG. 1. A distal portion of the expandable element 54 defines a basket having a closed distal end and configured to receive at least part of the thrombus after it has moved through a proximal mouth of the basket. In particular, the distal portion of the expandable element includes a proximal cylindrical segment 54A proximal to an intermediate frustoconical segment 54B, which is proximal to a tapered distal segment 54C. The details of the openings in the basket are not shown in FIG. 9B.

In addition, a proximal portion of the expandable element 54 includes a plurality of curved arms 56, which are similar to arms 19, 52, 62 discussed above, but are curved radially inward towards from a central longitudinal axis 58 of the thrombus-removal device 48.

FIG. 9C is a perspective view of another example thrombus-removal device 64 that includes an expandable element 66, which is an example of the expandable element 14 of FIG. 1. A distal portion of the expandable element 66 defines a basket includes a having a closed distal end and configured to receive at least part of the thrombus after it has moved through a proximal mouth of the basket. In particular, the distal portion of the expandable element 66 includes a proximal cylindrical segment 66A proximal to an intermediate frustoconical segment 66B, which is proximal to an intermediate cylindrical segment 66C, which is proximal to a tapered distal segment 66D. The details of the openings in the basket are not shown in FIG. 9C.

In addition, a proximal portion of the expandable element 66 includes a plurality of curved arms 68, which are similar to arms 19, 52, 62 discussed above, but are bent. Each of the bent arms 68 can be formed from multiple adjacent linear and/or curved sections that are positioned at a non-parallel angle relative to each other. In the example shown in FIG. 9C, each bent arm 68 includes a first section 68A and a second section 68B that are angled relative to each other (i.e., not parallel) and meet each other at a joint 116. One or both of the first and second sections 68A, 68B can be linear. In addition, or instead of being linear, one or both of the first and second sections 68A, 68B can be curved.

In some examples, the joint 116 is a rigid joint and the arm sections 68A, 68B are not configured to move relative to each other (e.g., pivot) at joint 116. In other examples, the arm sections 68A, 68B are configured to move relative to each other at joint 116, e.g., the respective arm 68 may flex at joint 116. This may help facilitate compression of the thrombus-removal device 64 into a delivery sheath and/or a retrieval sheath and/or expansion of the expandable element 66 due to a biasing of the arms 68 radially outward.

Although the arms 68 are shown as bending towards a central longitudinal axis 118 of the thrombus-removal device 64, in other examples, one or more of the arms 68 can be bent away from the central longitudinal axis 118.

FIG. 9D is an end view of the thrombus-removal device 64 of FIG. 9C and illustrates an example of a radially symmetric thrombus-removal device (symmetric about the central longitudinal axis 118). Any of thrombus-removal devices described herein may be radially symmetric.

The shape of the arms 98, 56, 68 shown in FIGS. 9A-9D may be used in combination with each other and/or with any of the configurations of thrombus-removal devices described herein above.

Figure 10:
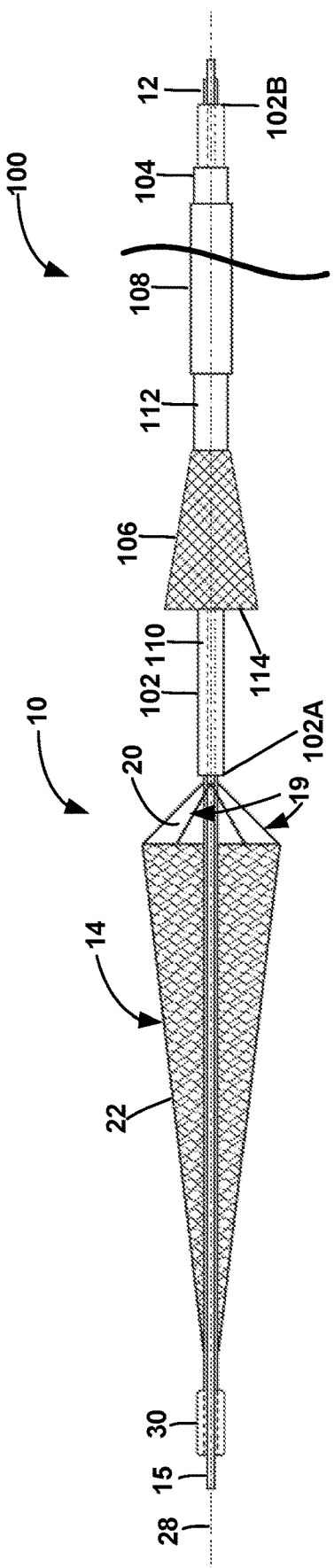
FIG. 10 is a conceptual side elevation view of the thrombus-removal device of FIG. 1 and an example catheter assembly.

Any suitable catheter assembly can be used to deliver the thrombus-removal devices described herein to a target site within vasculature of a patient and/or to retrieve the thrombus-removal devices from the vasculature. FIG. 10 is a side elevation view of the thrombus-removal device 10 of FIG. 1 and a catheter assembly 100. Although FIG. 10, as well as FIGS. 11A-13 are described with reference to the thrombus-removal device 10 of FIG. 1, in other examples, the catheter assemblies and methods described herein can be used with the other example the thrombus-removal devices described herein.

Figure 11A:
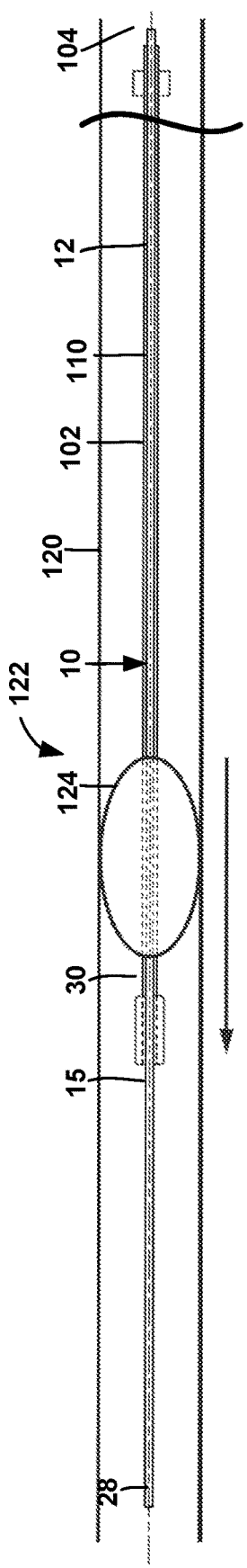
FIGS. 11A-11D illustrate an example thrombus-removal device being used to remove a thrombus from vasculature of a patient.

The catheter assembly 100 includes a delivery catheter 102, a retrieval catheter 104 defining or otherwise including a funnel 106, and a cover sheath 108 configured to cover the funnel 106 and hold the funnel 106 in a low profile configuration for delivery of the catheter assembly 100 to a target site. The entire length of the structures shown in FIG. 11A are not shown. For example, the retrieval catheter 104 is shown to be truncated in length. Although the delivery catheter 102, the catheter 104, and the cover sheath 108 are shown as being nested relative to each other in FIG. 10, in use, a clinician may deliver the thrombus-removal device 10 to a target site within a patient over the guidewire 15 and while the device 10 is within a lumen 110 of the delivery catheter 102, and then, at a later time, introduce the retrieval catheter 104 and cover sheath 108 into the patient over the guidewire 15 or the delivery catheter 102 at a later time, e.g., after thrombus is collected in the basket 22 of the thrombus-removal device 10.

The delivery catheter 102 and the retrieval catheter 104 have any suitable configuration. For example, each of the catheters 102, 104 may have a tubular catheter body that defines a respective lumen 110, 112. In some examples, one or both catheters 102, 104 may be a multi-lumen catheter that defines a plurality of lumens. In any of these examples, the catheters 102, 104 may be formed from any suitable material, such as, but not limited to, such as poly(tetrafluoroethylene) (PTFE), polyethylene (PE), high density polyethylene (HDPE), low density polyethylene (LDPE), other flexible plastic blends or thin-walled metal alloys or combinations thereof.

The delivery catheter lumen 110 is configured to contemporaneously receive the guidewire 15 and the expandable element 14 as well as part of the elongated support member 12. When the expandable element 14 is positioned within the delivery catheter lumen 110, the walls of the delivery catheter 102 apply a compressive force to the expandable element 14 to hold the expandable element in a relatively low profile delivery configuration. In FIG. 10, the expandable element 14 is shown in its deployed configuration, after it has been deployed from a distal end 102A of the delivery catheter. To deploy the expandable element 14, a clinician may push the expandable element 14 from the delivery catheter lumen 110 by applying a pushing force to a proximal portion of the elongated support member 12 proximally extending from a proximal end 102B of the delivery catheter 102. The elongated support member 12 is rigid enough to move distally out the delivery catheter distal end 102A in response to the pushing force. In addition to or instead of applying the pushing force to the elongated support member 12, the clinician may deploy the expandable element 14 from the delivery catheter 102 by at least proximally withdrawing the delivery catheter 102 relative to the expandable element 14, e.g., while holding the expandable element 14 in place or nearly in place via elongated support member 12.

The retrieval catheter 104 is configured to receive the thrombus-removal device 10 after thrombus is collected in the basket 22. The retrieval catheter lumen 112 is configured to contemporaneously receive the guidewire 15 and the expandable element 14 as well as part of the elongated support member 12 and, in some examples, the delivery catheter 102. However, the delivery catheter 102 and/or the guidewire 15 may be removed from the patient prior to introducing the retrieval catheter 104 over the elongated support member 12 of the thrombus-removal device 10.

The funnel 106 is positioned at a distal portion (e.g., a distal end) of the retrieval catheter 104 and is configured to facilitate the proximal withdrawal of the expanded expandable element 14 into the retrieval catheter lumen 112. For example, the funnel 106 defines a relatively large distal funnel mouth 114 and the funnel 106 tapers in a proximal direction from the distal funnel mouth 114. The tapered shape of the funnel 106 guides the expandable element 14 from the distal funnel mouth 114 into the retrieval catheter lumen 112, while compressing the expandable element 14 from the deployed configuration to a smaller profile configuration, e.g., the delivery configuration or a retrieval configuration that is smaller in profile than the deployed configuration but may be larger in profile than the delivery configuration due to the presence of collected occlusive material within the basket 22.

To help hold the funnel 106 in a lower profile configuration during the navigation of the retrieval catheter 104 through vasculature to the deployed expandable element 14 within the body of the patient, the catheter assembly 100 may include a cover sheath 108 that is configured to apply a compressive force to the funnel 106. Once the cover sheath 108 is proximally withdrawn so that it no longer covers the funnel 106, the funnel 106 may expand radially outward into the funnel shape shown in FIG. 10. For example, the funnel 106 may have a self-expandable frame, e.g., formed from nitinol struts, a nitinol mesh, or a nitinol braid or another suitable material, that is shape set to the funnel shape. As another example, the funnel 106 may be expanded radially outward with the aid of an expansion mechanism, such as a balloon.

In some examples, the funnel 106 is configured to be re-introduced into the cover sheath 108 after it is deployed from the cover sheath 108, such as by withdrawing the funnel 106 proximally into the cover sheath 108, by moving the cover sheath 108 distally over the funnel 106, or any combination thereof. Resheathing the funnel 106 in this manner may facilitate removal of the funnel 106 from the vasculature of the patient or an adjustment of the position of the funnel 106 within the vasculature. The funnel 106 can have a configuration that facilitates resheathing. For example, the funnel 106 can have a closed cell braid pattern (e.g., no open strands at the proximal end) that is less likely to catch on the distal end of the cover sheath 108 than open cells as the funnel 106 is re-introduced into the cover sheath 108.

In some examples, the retrieval catheter 104 includes a plurality of pores configured to enable liquid to exit the retrieval catheter inner lumen 112 and into, e.g., the blood stream. For example, the pores may be positioned along the funnel 106 and/or along a sidewall of the catheter 104 proximal to the funnel 106. The liquid may be expelled from thrombus within the basket 22 as the expandable element 14 is proximally withdrawn into the funnel 106. The plurality of pores of the retrieval catheter 104 may have a size sufficient to permit fluid to flow out of the retrieval catheter inner lumen 112 and may have any suitable shape (e.g., oval, circular, square, rectangular, triangular, or an irregular shape). For example, the plurality of pores can be defined by a sidewall of the retrieval catheter 104 and having a greatest cross-sectional dimension (e.g., a diameter in the case of circular pores) of about 1 mm to about 10 mm, such as about 5 mm. Cross-sectional dimension as used herein may refer to a diameter, a width, or an average diameter $D_A$, with $D_A=4A/P$ where A is the area of the cross-section and P is the perimeter of the cross-section.

As shown in FIG. 10, the delivery catheter 102 may have a smaller profile (e.g., outer diameter or other maximum outer cross-sectional dimension) than the retrieval catheter 104. This may be due at least in part to needing to accommodate the expandable element 14 after pieces of a thrombus are positioned within the basket 22, thereby increasing an overall profile of the expandable element 14.

FIGS. 11A-11D are conceptual figures of different stages of a method of removing a thrombus 124 from a blood vessel 120 of a patient using the thrombus-removal device 10. The varying diameter of blood vessel 120 shown in FIGS. 11A-11D may be due to, for example, the thrombus-removal device 10 causing the vessel 120 to widen. In some examples, a clinician introduces the guidewire 15 into a blood vessel 120 of a patient and navigates the guidewire 15 to a target site 122 within the blood vessel 120 at which there is a thrombus 124. As shown in FIG. 11A, while the thrombus-removal device 10 is positioned within the delivery catheter lumen 110 in its relatively low profile delivery configuration, the clinician may position the delivery catheter 102 over the guidewire 15 and guide the delivery catheter 102 and the thrombus-removal device 10 to the target site 122 over the guidewire 15. In the delivery configuration, the expandable element 14 may be in a radially compressed configuration due to a biasing force applied by the walls of the delivery catheter 102.

The clinician may push the distal end 102A of the delivery catheter 102 distally past the thrombus 124 in the direction indicated by the arrow shown in FIG. 11A. FIG. 11A illustrates the delivery catheter 102 within the thrombus 124 and positioned such that the thrombus-removal device 10 within the delivery catheter lumen 110 extends through the thrombus 124. The clinician may continue distally pushing the delivery catheter 102 through the thrombus 124 until the expandable element 14 of the thrombus-removal device 10 is distal to the thrombus 124. Because the delivery catheter 102 has a relatively low profile, pushing the delivery catheter 102 through the thrombus 124 may not cause parts of the thrombus 124 to break off or may only cause relatively small sizes of the thrombus 124 to break off.

Figure 11B:
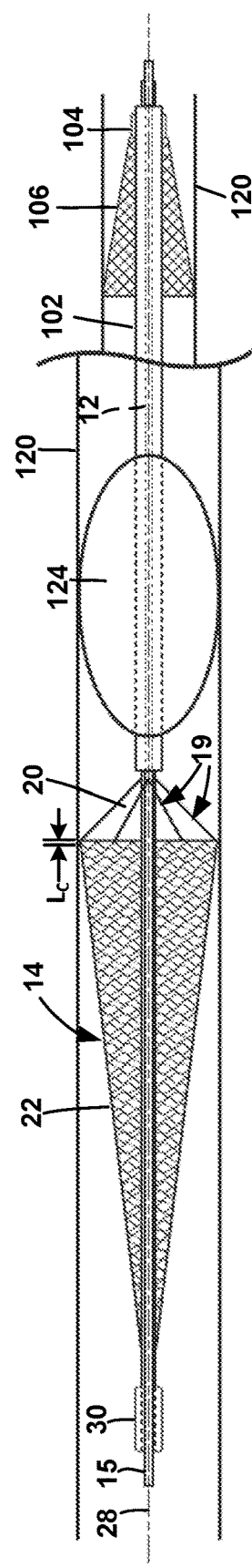
Figure 11C:
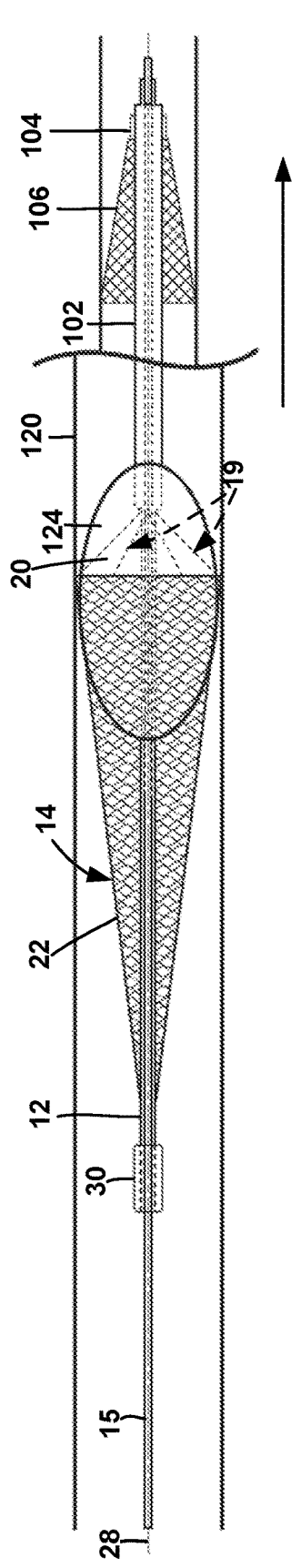

As shown in FIG. 11B, after the thrombus-removal device 10 is distal to the thrombus 124, the clinician may release the thrombus-removal device 10 from the delivery catheter lumen 110 to deploy the expandable element 14 in the blood vessel 120. For example, the clinician may distally push the thrombus-removal device 10 from the delivery catheter lumen 110 by applying a pushing force to the elongated support member 12 which is translated to the expandable element 14, by proximally withdrawing the delivery catheter 102 relative to the expandable element 14, or any combination of the two techniques. In examples in which the expandable element 14 is self-expanding, the expandable element 14 expands from its delivery configuration to its deployed configuration in response to being deployed from the delivery catheter lumen 110. In examples in which the expandable element 14 is not self-expanding, a clinician may use an expansion mechanism, such as a balloon or a pull wire connected to the arms 19, to expand the expandable element 14 into its deployed configuration.

In FIG. 11B, the expandable element 14 is in its deployed configuration and in apposition with the walls of the blood vessel 120. For example, the portion of the expandable element 14 defining the proximal mouth 20 may be engaged with the walls of the blood vessel 120. With the thrombus-removal device 10 in its deployed configuration, the clinician may pull the expandable element 14 proximally towards and through the thrombus 124, as indicated by the arrow shown in FIG. 11C. As the clinician moves the expandable element 14 proximally through the thrombus 124, at least part of the thrombus 124 moves through the proximal mouth 20 and into the interior space 26 defined by the basket 22. The basket 22 is configured to retain and hold pieces of the thrombus, thereby preventing at least part of the thrombus from moving downstream in the blood flow.

The plurality of arms 19 at the expandable element proximal portion 16 are configured to segment the thrombus 124 into smaller pieces as the thrombus 124 moves through the proximal mouth 20 and into the basket 22. For example, the plurality of arms 19 may be relatively rigid and configured to cut through the thrombus 124 as the expandable element 14 is moved proximally through the thrombus 124 and as the thrombus 124 is pushed past the arms 19 and into the distal basket 22. In this way, the arms 19 may facilitate the removal of the thrombus 124 from the patient by at least enabling the thrombus 124 to be segmented into pieces that fit into the basket 22 and that may eventually be withdrawn into the lumen 112 of the retrieval catheter 104.

In some examples, the clinician may leave the delivery catheter 102 in the blood vessel 120 during retrieval of the thrombus 124 and may deliver a therapeutic agent, e.g., a lytic agent, through the delivery catheter lumen 110 to the target site 122. For example, the therapeutic agent may be introduced into the delivery catheter lumen 110 at a proximal portion of the catheter 102 and delivered to the target site 122 via an opening at a distal-most end of the delivery catheter 102, through one or more side openings defined by a sidewall of the delivery catheter 102 (e.g., distributed along a wall of the delivery catheter 102 extending along a length of the elongated support member 12 or a part of the delivery catheter 102), or any combination thereof. In some examples, the therapeutic agent is delivered via the delivery catheter lumen 110 prior to deploying the expandable element 14, for example, while the expandable element 14 is still in the delivery catheter lumen 110. In other examples, the therapeutic agent is delivered via the delivery catheter lumen 110 after deploying the expandable element 14, i.e., while the expandable element 14 is no longer in the delivery catheter lumen 110.

The therapeutic agent may help further break down the thrombus 124 to enable capture of a larger part of the thrombus 124 in the basket 22. In addition, in some examples, the clinician may leave the guidewire 15 extending through the expandable element 14 during retrieval of the thrombus 124. The guidewire 15 may act as a rail along which the expandable element 14 may ride along, which may help maintain alignment between the expandable element 14 and the retrieval catheter lumen 112.

Figure 11D:
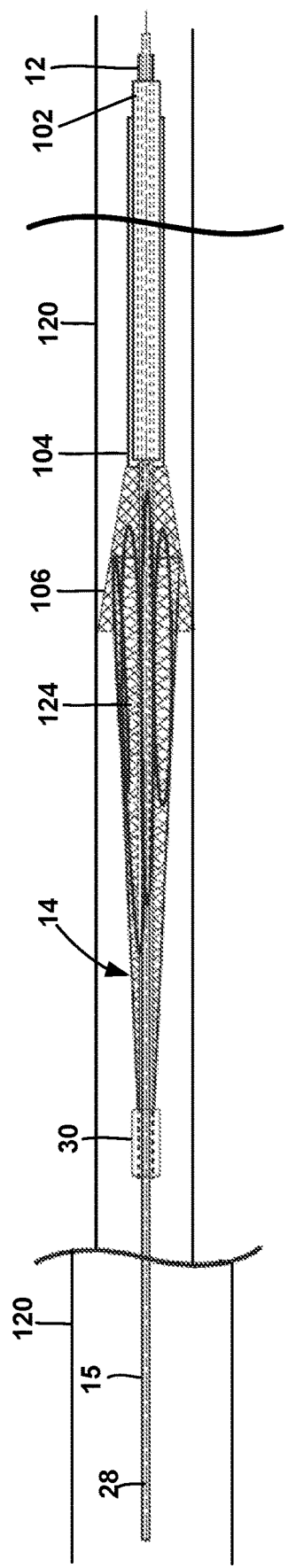

After the clinician has pulled the expandable element 14 through the thrombus 124 and collected at least some of the thrombus 124 in the basket 22, the clinician may proximally withdraw the expandable element 14 into the retrieval catheter 104. FIG. 11D illustrates the expandable element 14 being compressed into a smaller radial profile by the funnel 106 of the retrieval catheter 104 as the expandable element 14 is proximally withdrawn into the retrieval catheter lumen 112 via the funnel 106.

Due to the distal taper of the expandable element 14 and the corresponding decrease in volume in the basket of the expandable element 14 in the distal direction, the expandable element 14 is configured compresses the thrombus 124 positioned in the basket 22 as the expandable element 14 is proximally withdrawn into the retrieval catheter 104. Compressing the thrombus 124 may expel water from the thrombus 124 and dehydrate the thrombus 124, such that it decreases in volume in the basket 22 and compresses the expandable element 14 into a smaller profile for introduction into the retrieval catheter lumen 112.

As shown in FIG. 11D, the tapered shape of the expandable element 14, e.g., the tapered shape of the basket 22 in particular, may also help distribute the thrombus 124 longitudinally within the basket 22 as the expandable element 14 is proximally withdrawn into the retrieval catheter lumen 112. For example, the thrombus 124 within the basket 22 may spread out over a length of the basket 22, as shown in FIG. 11D as the retrieval catheter applies a compressive force to the basket 22. Distributing the thrombus 124 longitudinally within the basket 22 may help compress the expandable element 14 into a smaller profile for easier withdrawal from the patient, and may also mitigate the possibility of having too much relatively rigid material (e.g., the dehydrated thrombus) at the distal-most end of the basket 22. A relatively large bulk of relatively rigid material at the distal-most end of the basket may interfere with the proximal withdrawal of the thrombus-removal device 10 into the retrieval catheter 104.

As discussed above, in some examples, a clinician may deliver a therapeutic agent, e.g., a lytic agent, through the delivery catheter lumen 110 to the target site 122. For example, as shown in FIG. 12A, the therapeutic agent may be delivered to the target site 122 via an opening at a distal-most end of the delivery catheter 102, through one or more side openings 126 defined by a sidewall 127 of the delivery catheter 102, or via any combination thereof. As shown in FIG. 12A, in some examples, the sidewall 127 of the delivery catheter 102 defines a plurality of side openings 126 that are distributed (evenly or unevenly) along only a portion of the delivery catheter sidewall 127 that is proximal to the expandable element 14 when the expandable element 14 is disposed in the delivery catheter lumen 110. In other examples, however, the side openings 126 can also be defined in the portion of the sidewall 127 that longitudinally aligns with the expandable element 14 when the expandable element 14 is disposed in the delivery catheter lumen 110 and/or the portion of the sidewall that is distal to the expandable element 14.

Although side openings 126 on one longitudinal side of the sidewall 127 are shown in FIG. 12A, in some examples, the side openings 126 may be disposed on the other longitudinal side of the sidewall 127, too (e.g., distributed around an outer circumference of the delivery catheter 102 in examples in which the delivery catheter 102 is circular in cross-section).

In some examples, the therapeutic agent is delivered via the delivery catheter lumen 110 after deploying the expandable element 14, i.e., while the expandable element 14 is no longer in the delivery catheter lumen 110. In addition to, or instead of, delivering the therapeutic agent after deploying the expandable element 14, the therapeutic agent is delivered via the delivery catheter lumen 110 prior to deploying the expandable element 14 while the expandable element 14 is still in the delivery catheter lumen 110. In some of these examples, the delivery catheter 102 can include a seal 128 positioned distal to the side openings 126 and proximal to the expandable element 14 to help prevent the therapeutic agent from being delivered out a distal-most opening of the delivery catheter 102. The seal 128 may create a fluid-tight barrier that helps prevent the therapeutic agent from passing distally past the seal 128 towards the expandable element 14. In other examples, however, the delivery catheter 102 may not include a seal 128 and instead the therapeutic agent may be free to be delivered out the distal-most opening of the delivery catheter 102 in addition to out of the side openings 126.

FIG. 12B illustrates the expandable element 14 after it is deployed from the delivery catheter lumen 110. The expandable element 14 is shown schematically in FIGS. 12A and 12B and further details of the expandable element 14 can be seen in the previous figures.

Figure 13:
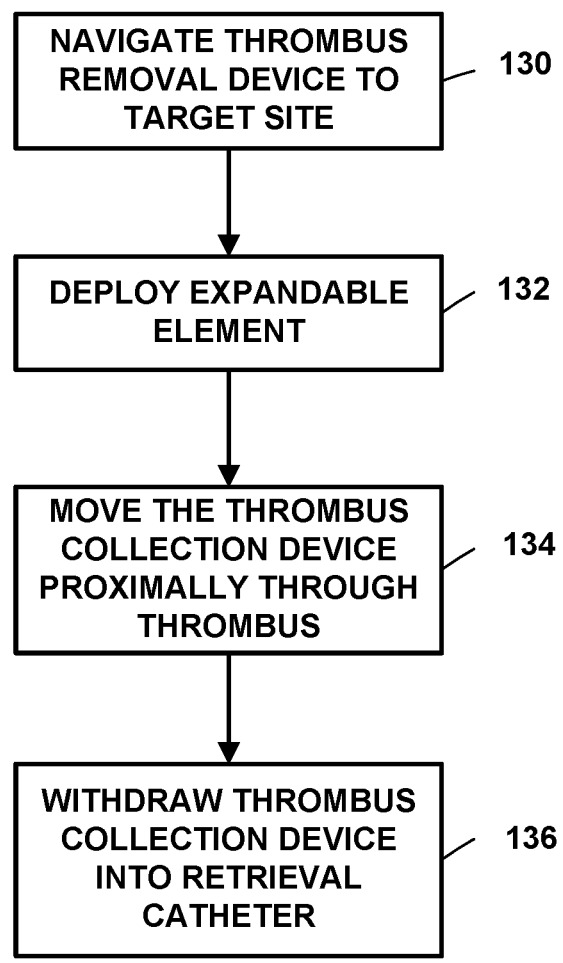
FIG. 13 is a flow diagram of an example method of removing a thrombus from vasculature of a patient using an example thrombus-removal device described herein.

FIG. 13 is a flow diagram of an example method of removing a thrombus from vasculature of a patient using the thrombus-removal device 10. A clinician may navigate the thrombus-removal device 10 to a target site 122 (FIGS. 11A-11D) within a patient (130), which can be, for example, in a blood vessel 120 (FIGS. 11A-11D). For example, the clinician may deliver the thrombus-removal device 10 to a target site 122 with the aid of a delivery catheter 102, as described with reference to FIG. 11A. The clinician may position the expandable element 14 on a distal side of a thrombus 124, as described with reference to FIG. 11B, and deploy the expandable element 14 (132). The clinician may then proximally withdraw the thrombus-removal device 10, e.g., the expandable element 14 in particular, through the thrombus 124 (134) to collect at least part of the thrombus 124 in the distal basket 22 of the expandable element 14, as described with reference to FIG. 11C. After collecting at least part of the thrombus 124 in the distal basket 22, the clinician may remove the collected parts of the thrombus 124 and the thrombus-removal device 10 from the patient (136), e.g., with the aid of a retrieval catheter 104 as described with reference to FIG. 11D.

Figure 14:
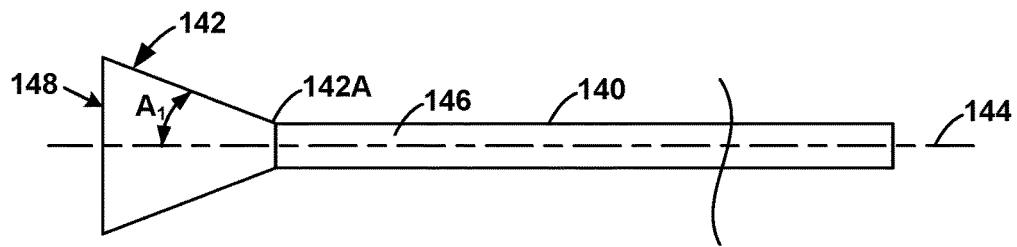
FIG. 14 is a conceptual side elevation view of an example retrieval catheter and funnel that has a continuous taper.

FIG. 14 is a conceptual side elevation view of an example retrieval catheter 140, which includes a funnel 142 and defines a central longitudinal axis 144. The retrieval catheter 140 and the funnel 142 are examples of the retrieval catheter 104 and the funnel 106 described above, e.g., with reference to FIG. 2A. The retrieval catheter 140 includes an elongated body defining at least one retrieval catheter lumen 146, e.g., a lumen configured to receive the guidewire 15 and the thrombus-removal device 10.

The funnel 142 is positioned at a distal end of the retrieval catheter 140 and is configured to facilitate the proximal withdrawal of the expanded expandable element 14 of the thrombus-removal device 10 into the retrieval catheter lumen 146. The funnel 142 defines a funnel mouth 148, through which the thrombus-removal device 10 can be introduced into the retrieval catheter lumen 146.

In its expanded state, shown in FIG. 14, the funnel 142 defines a proximal taper towards the longitudinal axis 144, such that the funnel 142 defines a larger cross-sectional dimension (e.g., a diameter in the case of a round cross-section) at distal funnel mouth 148 than at a proximal end 142A of the funnel 142, the cross-section being taken in a direction orthogonal to the longitudinal axis 144. The angle $A_1$ at which the funnel 142 proximally tapers towards the longitudinal axis 144 is constant along a length of the funnel 142, the length being measured along the longitudinal axis 144. In some examples, the constant taper angle $A_1$ is measured between an innermost surface of the funnel 142 and the central longitudinal axis 144. In other examples, the constant taper angle can be defined between the outermost surface of the funnel 142 and the central longitudinal axis 144. In some examples, the taper angle $A_1$ is about 15 degrees to about 75 degrees, such as about 30 degrees to about 60 degrees or about 45 degrees.

Due to the constant taper angle $A_1$, the funnel 142 may apply a relatively even compression force to the expandable element 14 (and the thrombus 124) (FIG. 11D) as the expandable element 14 is proximally withdrawn into the retrieval catheter 140.

Figure 15:
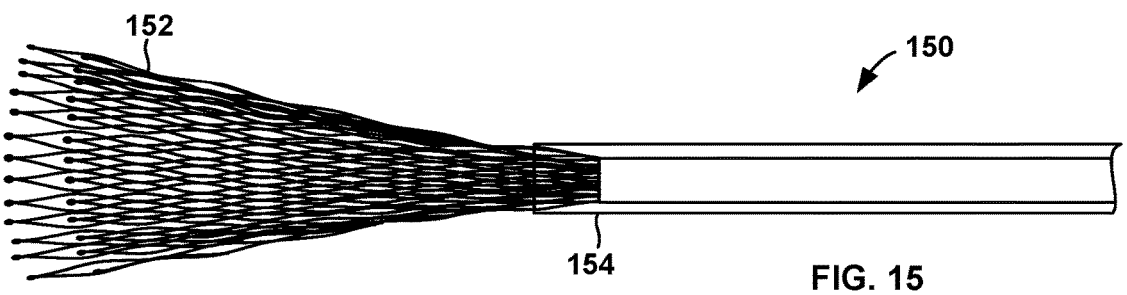
FIG. 15 is an illustration of an example retrieval catheter and funnel.

FIG. 15 is an illustration of an example retrieval catheter 150, which includes an example funnel 152 having a constant taper angle. FIG. 15 also illustrates an example cover sheath 154, which is configured to apply a compressive force to the funnel 152 to hold the funnel 152 in a relatively low-profile configuration. In FIG. 15, the cover sheath 154 is partially proximally withdrawn away from the funnel 152, and the funnel 152 is partially expanded radially outward. As shown in FIG. 15, in some examples, the funnel 152 can be at least partially formed from a plurality of struts (e.g., shape memory struts, such as nitinol struts) that are configured to self-expand into an expanded configuration, as shown with the part of the funnel 152 that is outside the cover sheath 154.

Although funnels 142, 152 having constant tapers defined by constant taper angles are shown in FIGS. 14 and 15, the funnel 106 of the retrieval catheter 104 can define any suitable taper angle. For example, as shown in FIGS. 16-21, a funnel of a retrieval catheter can define a variable taper, which can be a taper angle that changes over a length of the funnel, the length being measured along a longitudinal axis of the respective retrieval catheter.

Figure 16:
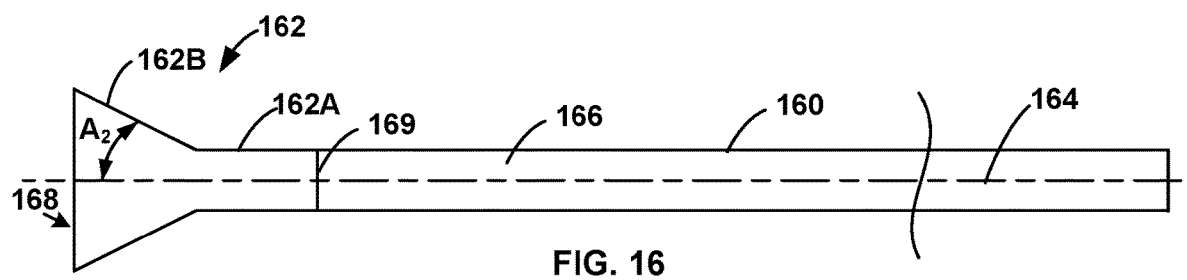
FIG. 16 is a conceptual side elevation view of an example retrieval catheter and funnel that has a variable taper.

FIG. 16 is a conceptual side elevation view of an example retrieval catheter 160, which includes an example funnel 162. The retrieval catheter 160 defines a central longitudinal axis 164 passing through a retrieval catheter lumen 166. The retrieval catheter 160 and the funnel 162 are examples of the retrieval catheter 104 and the funnel 106 described above. The retrieval catheter 140 can include an elongated body defining at least one retrieval catheter lumen 146, e.g., a lumen configured to receive the guidewire 15 and the thrombus-removal device 10.

In its expanded state, shown in FIG. 16, in which no external compressive forces are applied to the funnel 162 to collapse it into a lower profile configuration, an outer surface of a proximal funnel portion 162A of the funnel 162 has a generally straight profile relative to the central longitudinal axis 164 and a distal funnel portion 162B of the funnel 162 tapers in a proximal direction from the funnel mouth 168 towards the central longitudinal axis 164. Thus, the proximal funnel portion 162A does not define a taper angle because the innermost surface of the funnel 162 in the proximal funnel portion 162A is generally parallel to (e.g., parallel or nearly parallel to the extent permitted by manufacturing tolerances) the central longitudinal axis 164. In some examples, the proximal funnel portion 162A has the same outer cross-sectional dimension (e.g., a diameter) as an elongated body of the retrieval catheter 160, such that no ledge is formed at region 169 between the funnel 162 and the elongated body.

The distal funnel portion 162B defines a taper angle $A_2$, which is the angle defined between an innermost surface of the distal funnel portion 162B and the central longitudinal axis 164. In other examples, the taper angle $A_2$ can be defined between the outermost surface of the distal funnel portion 162B and the central longitudinal axis 164.

In some examples, the taper angle $A_2$ is about 15 degrees to about 75 degrees, such as about 30 degrees to about 60 degrees or about 45 degrees.

Because the inner surfaces of the proximal funnel portion 162A and the distal funnel portion 162B are oriented at different angles relative to the central longitudinal axis 164 when the funnel 162 is in its expanded state, the funnel 162 may be considered to have a variable taper. Due to the variable taper of the funnel 162, the funnel 162 may apply different compression forces to the expandable element 14 (and the thrombus 124) (FIG. 11D) as the expandable element 14 is proximally withdrawn into the retrieval catheter 140. That is, the compression force applied by the funnel 162 to the expandable element 14 may be a function of where the expandable element 14 is located within the funnel 162. The proximal funnel portion 162A may apply a greater compressive force to the expandable element 14 than the distal funnel portion 162B because the proximal funnel portion 162A tapers less than the distal funnel portion 162B. That is, a taper angle of the proximal funnel portion 162A is less than a taper angle $A_2$ of the distal funnel portion 162B.

Figure 17:
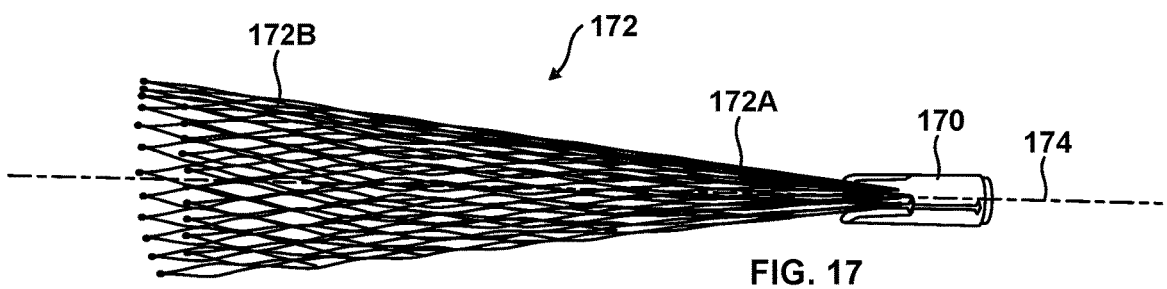
FIGS. 17 and 18 are illustrations of example retrieval catheters and funnels that have variable tapers.

FIG. 17 is an illustration of another example retrieval catheter 170, which includes an example funnel 172 connected to a distal end of the retrieval catheter 170. The funnel 172 has a variable taper angle. In particular, the funnel 172 includes a proximal funnel portion 172A having a first taper angle relative to a central longitudinal axis 174 of the retrieval catheter 170 and a distal funnel portion 172B having a second taper angle relative to the central longitudinal axis 174, where the second taper angle is greater than the first taper angle.

Figure 18:
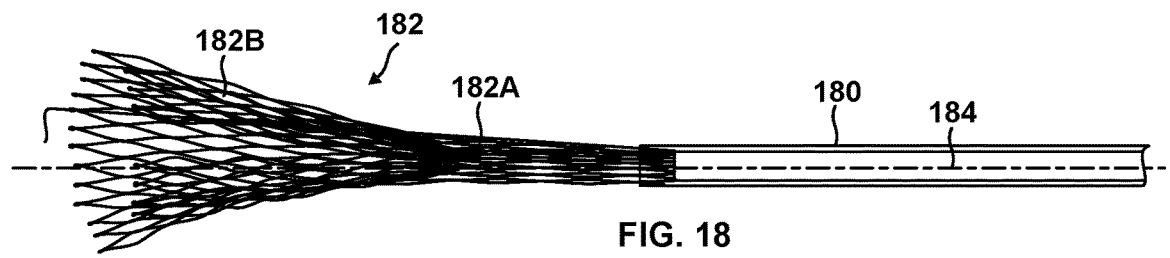

FIG. 18 is an illustration of another example retrieval catheter 180, which includes an example funnel 182 connected to a distal end of the retrieval catheter 180. The funnel 182 has a variable taper angle. In particular, the funnel 182 includes a proximal funnel portion 182A having a first taper angle relative to a central longitudinal axis 184 of the retrieval catheter 180 and a distal funnel portion 182B having a second taper angle relative to the central longitudinal axis 184, where the second taper angle is greater than the first taper angle.

Figure 19:
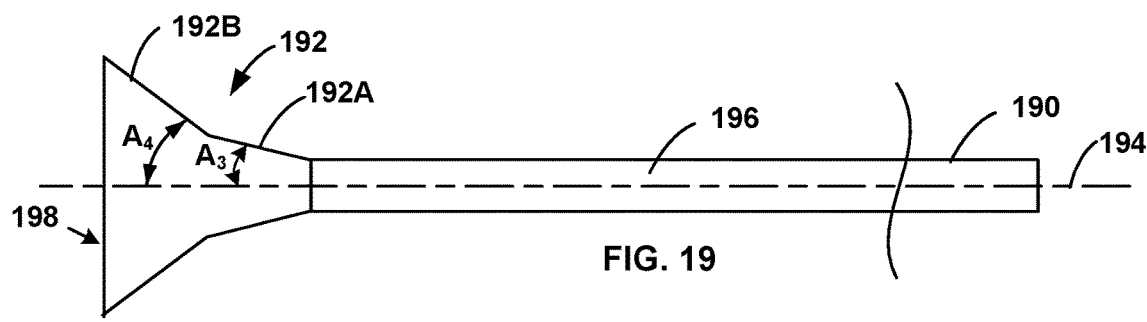
FIG. 19 is a conceptual side elevation view of an example retrieval catheter and another example funnel that has a variable taper.

FIG. 19 is a conceptual side elevation view of an example retrieval catheter 190, which includes an example funnel 192 connected to a distal end of the retrieval catheter 190. The retrieval catheter 190 defines a central longitudinal axis 194. The retrieval catheter 190 and the funnel 192 are examples of the retrieval catheter 104 and the funnel 106 described above. The retrieval catheter 190 can include an elongated body defining at least one retrieval catheter lumen 196, e.g., a lumen configured to receive the guidewire 15 and the thrombus-removal device 10.

In its expanded state, shown in FIG. 19, in which no external compressive forces are applied to the funnel 192 to collapse it into a lower profile configuration, a proximal funnel portion 192A of the funnel 192 tapers towards the central longitudinal axis 194 in a proximal direction from a distal funnel portion 192B of the funnel 192 towards a proximal end of the retrieval catheter 190 and the distal funnel portion 192B tapers towards the central longitudinal axis 194 in a proximal direction from the funnel mouth 198 towards the proximal funnel portion 192A.

The proximal funnel portion 192A defines a taper angle $A_3$, which is the angle defined between an innermost surface of the proximal funnel portion 192A and the central longitudinal axis 194. In other examples, the taper angle $A_3$ can be defined between the outermost surface of the distal funnel portion 162B and the central longitudinal axis 164. In some examples, the taper angle $A_3$ is about 15 degrees to about 75 degrees, such as about 20 degrees to about 50 degrees or about 30 degrees.

The distal funnel portion 192B defines a taper angle $A_4$, which is the angle defined by an innermost surface of the distal funnel portion 192B and the central longitudinal axis 194. In other examples, the taper angle $A_4$ can be defined between the outermost surface of the distal funnel portion 192B and the central longitudinal axis 194. The taper angle $A_4$ of the distal funnel portion 192B is greater than the taper angle $A_3$ of the proximal funnel portion 192A. In some examples, the taper angle $A_4$ is about 15 degrees to about 75 degrees, such as about 30 degrees to about 60 degrees or about 45 degrees.

As with the funnel 162 (FIG. 14) having a variable taper angle, the funnel 192 shown in FIG. 19 having a variable taper angle may apply different compression forces to the expandable element 14 (and the thrombus 124) (FIG. 11D) as the expandable element 14 is proximally withdrawn into the retrieval catheter 190. The proximal funnel portion 192A may apply a greater compressive force to the expandable element 14 than the distal funnel portion 192B because the proximal funnel portion 192A tapers less than the distal funnel portion 192B, and, therefore, defines a smaller "neck" for the expandable element 14 to pass through in order to enter the retrieval catheter lumen 196.

The flared end of the funnel 192, e.g., defined by the relatively large taper angle $A_4$ of the distal funnel portion 192B, may help the funnel 192 engage with a vessel wall in order to help anchor funnel 192 in the vessel during retrieval of the thrombus-removal device 10 and to help prevent particulate matter, e.g., separated from the thrombus 124, from passing between the funnel 192 and the vessel wall. Thus, the distal funnel portion 192B defining a larger flare may help the funnel 192 achieve successful apposition with vessel wall while still compressing the expandable element 14 and any thrombus 124 collected within the expandable element 14. The less flared proximal funnel portion 192A may help the funnel 192 apply additional compressive force to the expandable element 14 and the thrombus 124 to further compact the thrombus for retrieval into the retrieval catheter lumen 196.

The relatively large taper angle $A_4$ of the distal funnel portion 192B may also help prevent prolapse of the funnel 192 when the thrombus-removal device 10 is withdrawn proximally into the funnel 192.

Although a funnel 192 having a variable taper defined by two different taper angles $A_3$, $A_4$ is shown in FIG. 19, in other examples of a variable taper, a funnel can define three or more taper angles.

Figure 20:
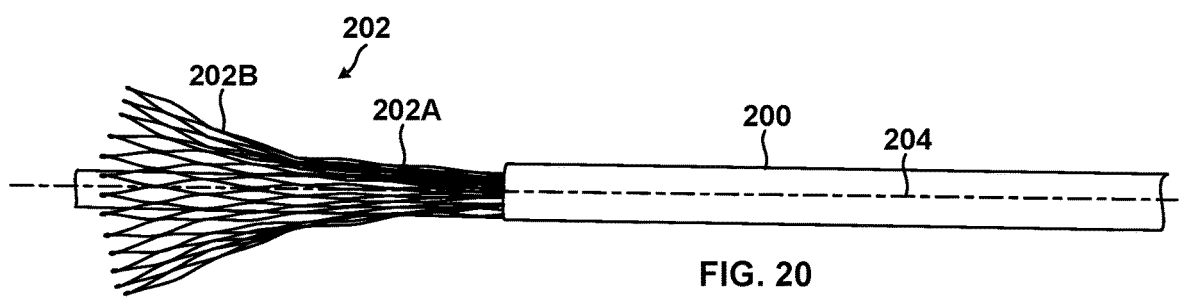
FIG. 20 is an illustration of an example retrieval catheter and funnel that has a variable taper.

FIG. 20 is an illustration of another example retrieval catheter 200, which includes an example funnel 202 having a variable taper angle. The retrieval catheter 200 defines a central longitudinal axis 204. The funnel 202 includes a proximal funnel portion 202A having a first taper angle relative to a central longitudinal axis 204 of the retrieval catheter 200 and a distal funnel portion 202B having a second taper angle relative to the central longitudinal axis 204, where the second taper angle is greater than the first taper angle.

Figure 21:
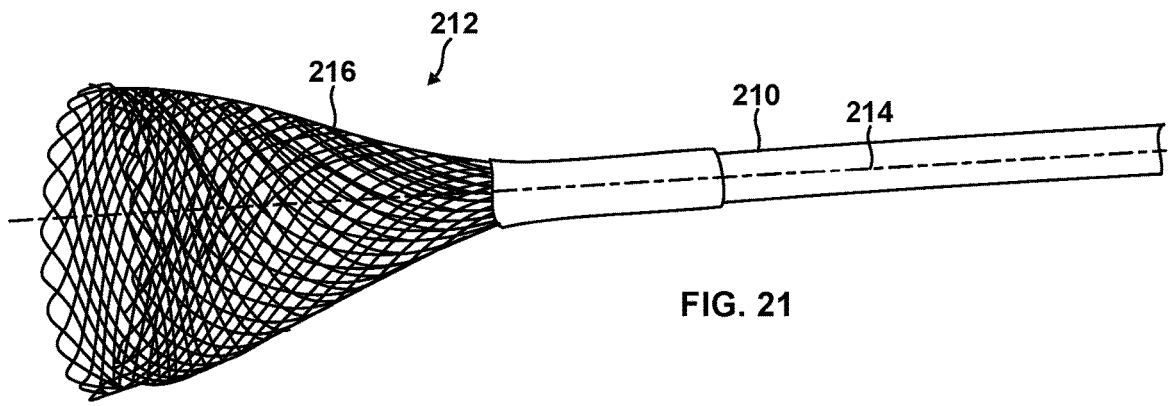
FIG. 21 is an illustration of an example retrieval catheter and funnel that has a bell shape.

In some examples, the funnel 106 (FIG. 2A) can have a conical or frustoconical profile, as shown above with respect to FIGS. 2A and 14-21. In other examples, the funnel 106 can have a different shape, such, but not limited to, as a bell-shape that has curvilinear outer surface, as shown in FIG. 21. The non-conical or non-frustoconical shape defined by the outer surfaces of the funnel can be a result of a variable taper angle.

FIG. 21 is an illustration of another example retrieval catheter 210, which includes an example funnel 212 connected to a distal end of the retrieval catheter 210. The funnel 212 has a variable taper angle and defines a bell shape. An outer surface 216 of the funnel 212 defines a bell shape, e.g., curves away from longitudinal axis 214 to define a continuously changing taper angle in some or all portions of the funnel 212.

The taper of a funnel, whether the taper is constant as shown in FIG. 14 with respect to funnel 142 or is variable as shown in FIGS. 16-21 with respect to funnels 162, 172, 182, 192, 202, and 212 can influence how water is expelled from the thrombus 124 as the expandable element 14 and thrombus 124 are proximally withdrawn into the respective retrieval catheter. Accordingly, the taper of the funnel is a variable that may be modified to facilitate compaction of the thrombus 124 into a retrieval catheter lumen. In examples in which a funnel has a variable taper, as shown in FIGS. 16-21, where the taper angle increases in a distal direction, the thrombus 124 may be progressively compressed, such that there is a time dependency to how the thrombus is compressed. For example, if the proximal most taper angle is less than the distal taper angle, e.g., as with the example funnels shown in FIGS. 16-21, then the compressive force applied by the proximal funnel portion (e.g., the proximal funnel portion 162A) may apply more compressive force to the thrombus 124 than the distal funnel portion (e.g., the distal funnel portion 162B) as the expandable element 14 and thrombus 124 are proximally withdrawn into the respective retrieval catheter 160, 170, 180, 190, 200, and 210. That is, the proximal funnel portions may apply more compressive force to the thrombus 124 than the distal funnel portions when the proximal funnel portion is parallel to the central longitudinal axis of the catheter or defines less of a taper angle than the distal funnel portion.

As with the funnel 106, any of the funnels 162, 172, 182, 192, 202, and 212 are configured to be held in a lower profile configuration, e.g., during the navigation of the respective retrieval catheter through vasculature to the deployed expandable element 14 within the body of the patient, by the cover sheath 108, which is configured to apply a compressive force to the funnel 106. Once the cover sheath 108 is proximally withdrawn so that it no longer covers the funnel, the funnel may expand radially outward into the expanded funnel shapes shown in FIGS. 14-21. For example, the funnels 162, 172, 182, 192, 202, and 212 may each be configured to self-expand into the expanded funnel configuration, e.g., the funnels may be formed from nitinol struts, a nitinol mesh, or a nitinol braid or another suitable material, that is shape set to the funnel shape. As another example, the funnels may be expanded radially outward with the aid of an expansion mechanism, such as a balloon.

Funnel described herein, including funnels 106, 162, 172, 182, 192, 202, and 212, can have any suitable length, which is measured along the longitudinal axis of the respective retrieval catheter 104, 140, 150, 160, 170, 180, 190, 200, and 210. In some examples, a funnel can have a length of about 1 cm to about 6 cm, such as about 2 cm to about 4 cm, or about 3 cm. In addition, the funnels described herein can have any suitable maximum outer cross-sectional dimension (e.g., an outer diameter), which may be measured at the respective distal mouth and in a direction orthogonal to the longitudinal axis of the respective retrieval catheter. In some examples, a funnel has an outer diameter of about 10 mm to about 20 mm, such as about 16 mm. Funnels may have other dimensions in other examples.

In some examples, any of the funnels 106, 162, 172, 182, 192, 202, and 212, described herein may be formed from a laser-cut tube, e.g., using any suitable technique such as techniques used to formed stents. For example, a nitinol tube may be cut to define a plurality of struts, and the resulting funnel structure can be configured to self-expand from a compressed state to an expanded state. A laser-cut tube may exhibit improved functionality, robustness, and manufacturability over a braided funnel. For example, a shape of the funnel may be easier to control and configure (e.g., using a heat treatment technique, such as annealing) when the funnel is formed to have a unitary body construction (i.e., is one piece, such as in the case of a laser-cut tube or another cut tube) versus a braid that is formed by a plurality of interwoven filaments.

In addition, in some examples, a laser cut structure may exhibit less or even no foreshortening compared to a braided structure. Foreshortening may refer to the shortening of the funnel length (measured along a longitudinal axis of the retrieval catheter) upon expansion of the funnel from the compressed configuration to an expanded configuration. The reduction in foreshortening may enable the space inside a delivery sheath, e.g., the cover sheath 108, to be efficiently used because the length of the funnel in the compressed state may better correspond to the length of the funnel in the expanded state with a reduction in foreshortening.

Figure 22:
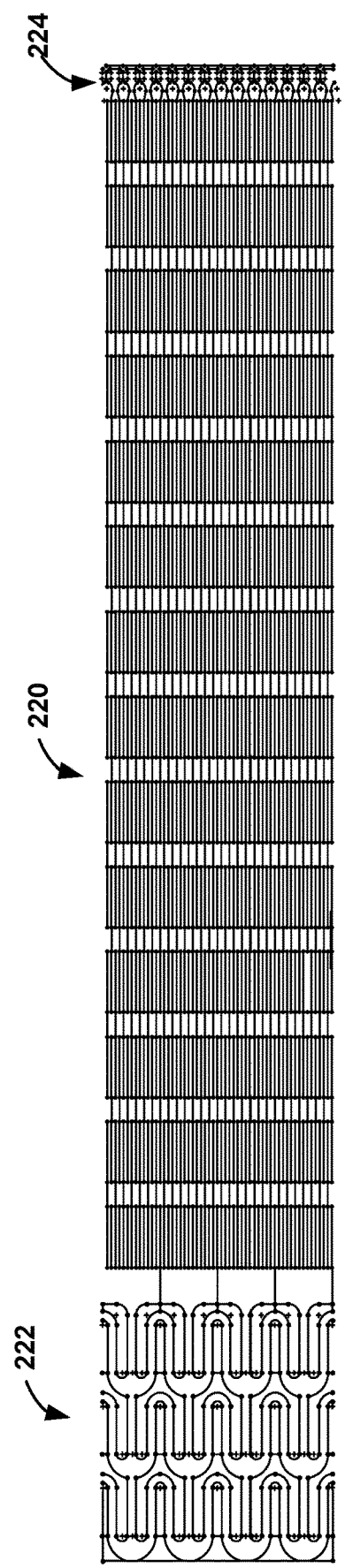
FIG. 22 is an example configuration of struts that can be used to define a funnel.

FIG. 22 is an example configuration of struts that can be used to define any of the funnels 106, 162, 172, 182, 192, 202, and 212, described herein. FIG. 22 illustrates an example strut configuration 220, which is an example pattern (e.g., a laser-cut pattern) that can be used to cut a tube that is heat-shaped into a funnel. The end portions 222, 224 of the structure shown in FIG. 22 may be used for bonding purposes and may not form part of a funnel. The strut configuration 220 may correspond to the arrangement of struts of a section of a funnel that is laid flat and in an unexpanded configuration.

The example delivery catheters and retrieval catheters of the catheter assemblies described herein can each include any suitable handle at the proximal portions of the respective catheter, in order to facilitate gripping and manipulation of the catheter by a clinician or other user. In examples described herein, these delivery catheter handles and retrieval catheter handles may include one or more features configured to improve or facilitate a thrombus-removal procedure. For example, the delivery catheter handle and the retrieval catheter handle may be configured to removably couple together (e.g., mechanically connect and subsequent disconnect from each other without any adverse impacts to the structural integrity or structures of the handles) during certain portions of the thrombus-removal procedure, enabling the clinician to manipulate the catheter assembly with just one hand, without placing excessive stress on the lumens of the catheters. The excessive stress on the lumens of the catheters, e.g., from a clinician directly gripping elongated bodies of the catheters (e.g., the sheaths) rather than the handles, may cause kinking or other adverse structural impacts to the catheter bodies that may adversely affect the function of the catheters. The interlocking-handles may free-up one hand of the clinician during navigation of the catheter assembly to a target site within vasculature of a patient, e.g., to enable the clinician to use one hand to stabilize other components, such as an introducer sheath, during the medical procedure. In contrast, for example, a catheter assembly that includes catheters handles that cannot be coupled together (e.g., without the use of an external component separate from the catheter assemblies) may require two clinician hands to navigate the catheter assembly to a target site within vasculature of a patient.

Example delivery catheter handles described herein may include an actuator mechanism, such as a slider, coupled to the delivery catheter to control expansion and contraction of a thrombus-removal device. In some examples herein, the slider may define a proximal portion of a fluid pathway between a fluid-infusion port and a delivery catheter lumen of the delivery catheter, enabling the clinician to inject a desired therapeutic fluid, such as a lytic agent, through the delivery catheter during the thrombus-removal procedure. In some examples, the fluid-infusion port may be oriented at an oblique angle relative to a central longitudinal axis of the delivery catheter handle, improving access by the clinician and reducing a form factor of the delivery catheter, which may reduce costs associated with product packaging, storage, and transportation.

In some examples, the retrieval catheter handle defines a customizable aspiration port, enabling variable types of suction sources or other fluid sources to couple to the retrieval catheter. For example, the retrieval catheter handle may include a removable adaptor configured to modify a lumen size (e.g., a bore width, such as a diameter) of the aspiration port from a larger bore to a smaller bore, such as a smaller bore size corresponding to a standard-size syringe. The delivery catheter handle and the retrieval catheter handle may include one or more of these features among other features providing a number of practical applications for removing a thrombus from the vasculature of a patient, as detailed further below.

Figure 23A:
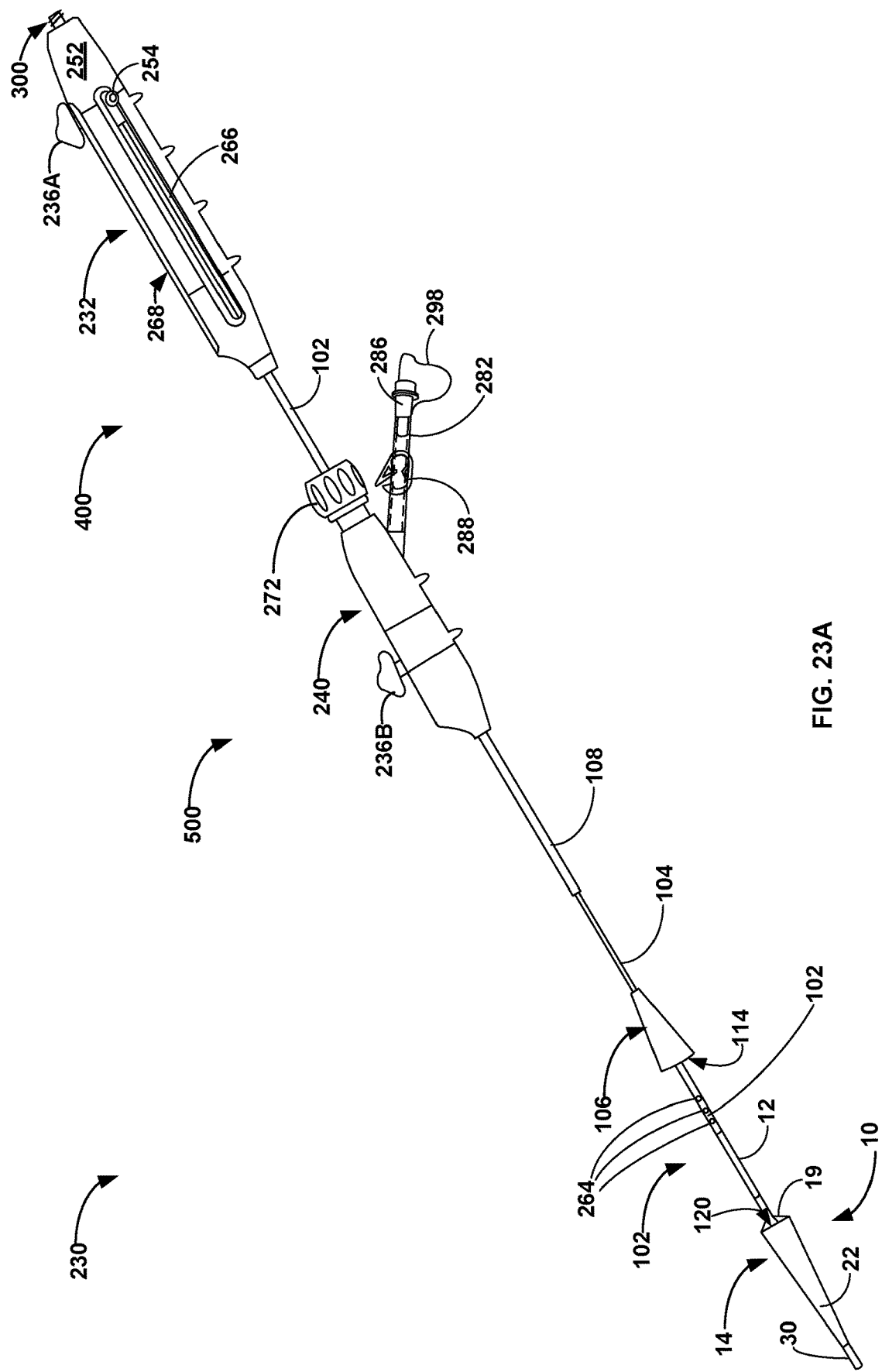
FIG. 23A is a conceptual side view of an example catheter assembly including a delivery catheter assembly, a retrieval catheter assembly, an outer sheath, and a thrombus-removal device.
Figure 23B:
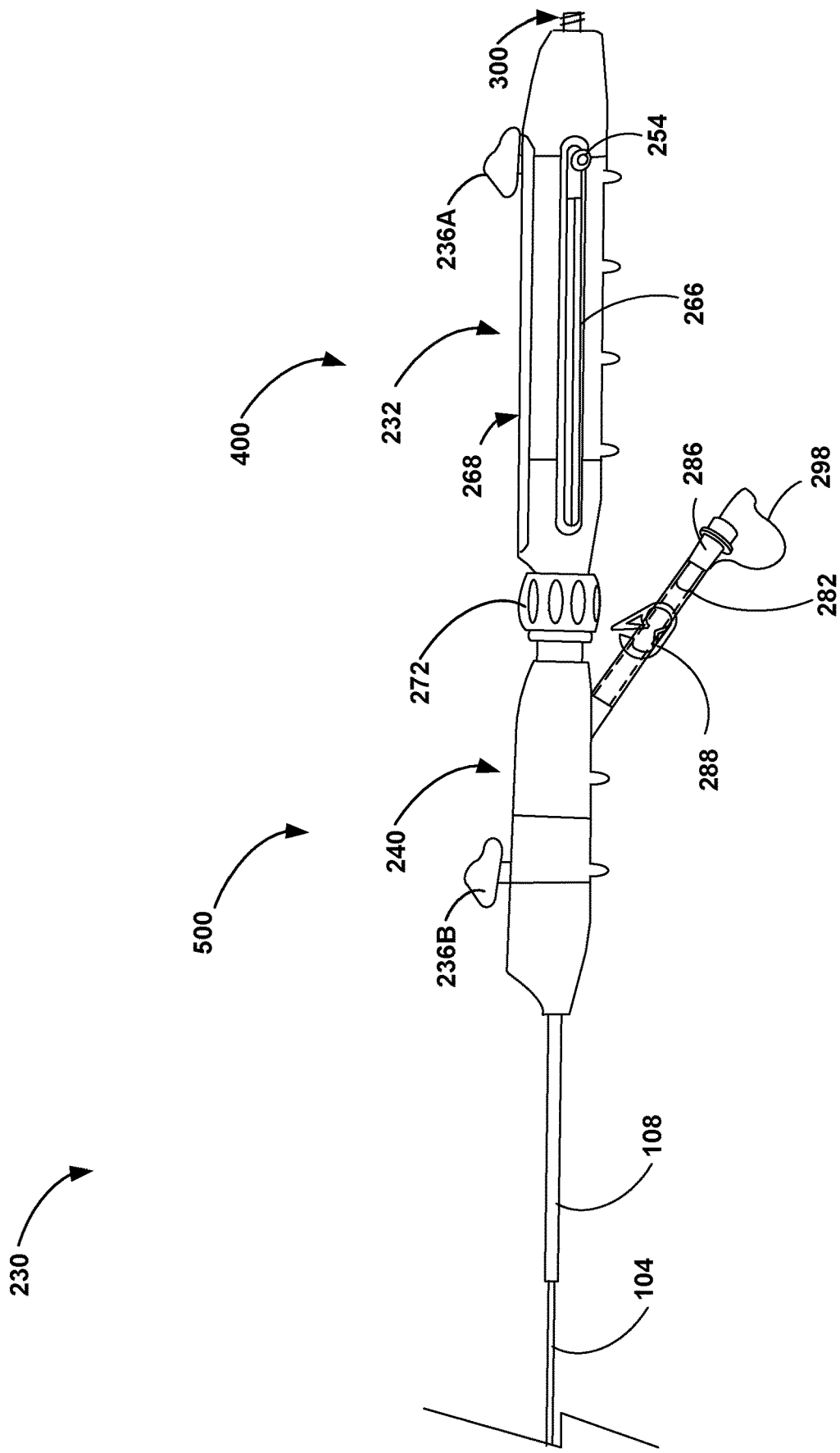
FIG. 23B is a conceptual side view of the catheter assembly of FIG. 23A and illustrates a delivery catheter handle and a retrieval catheter handle connected together.
Figure 24:
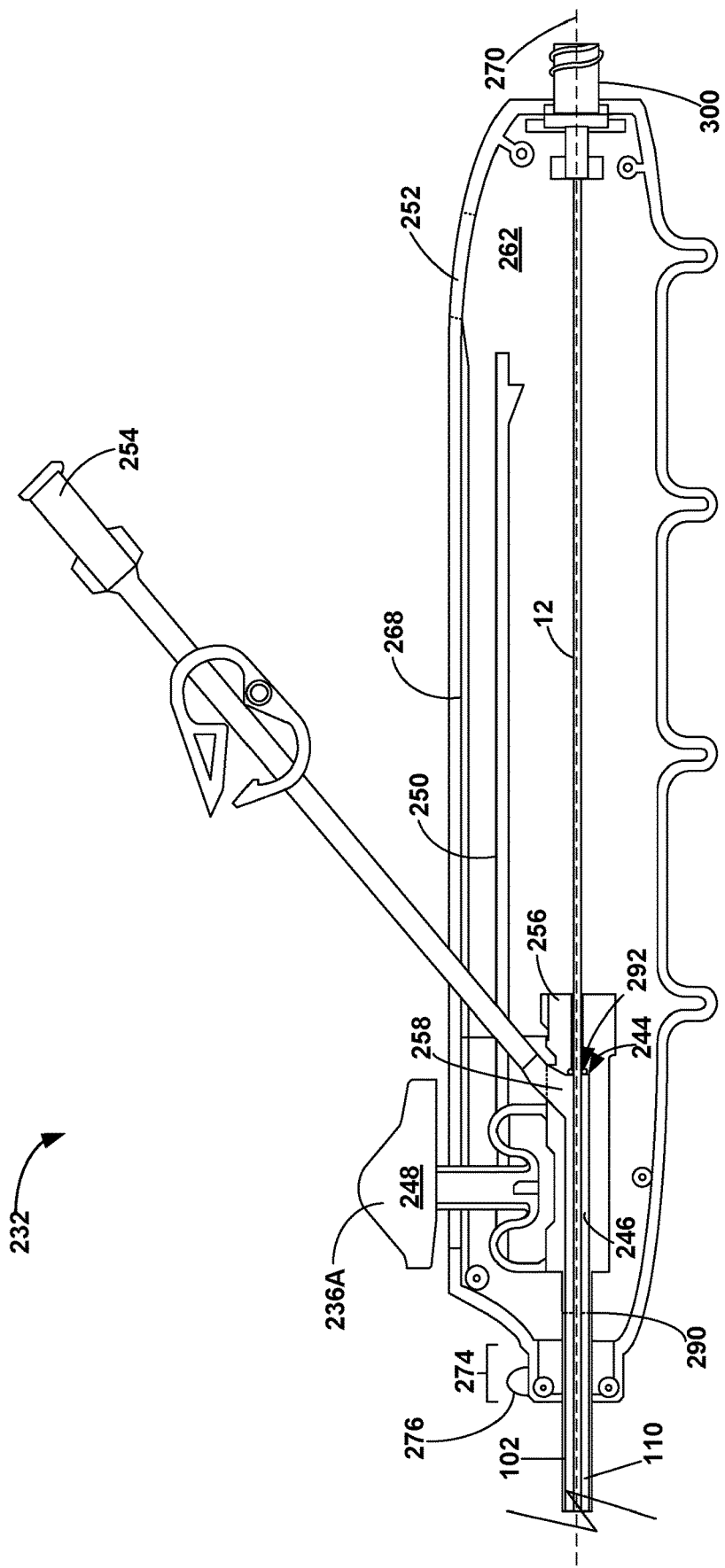
FIG. 24 is a schematic cross-sectional view of a proximal portion of an example of the delivery catheter assembly of the catheter assembly of FIGS. 23A and 23B.
Figure 25:
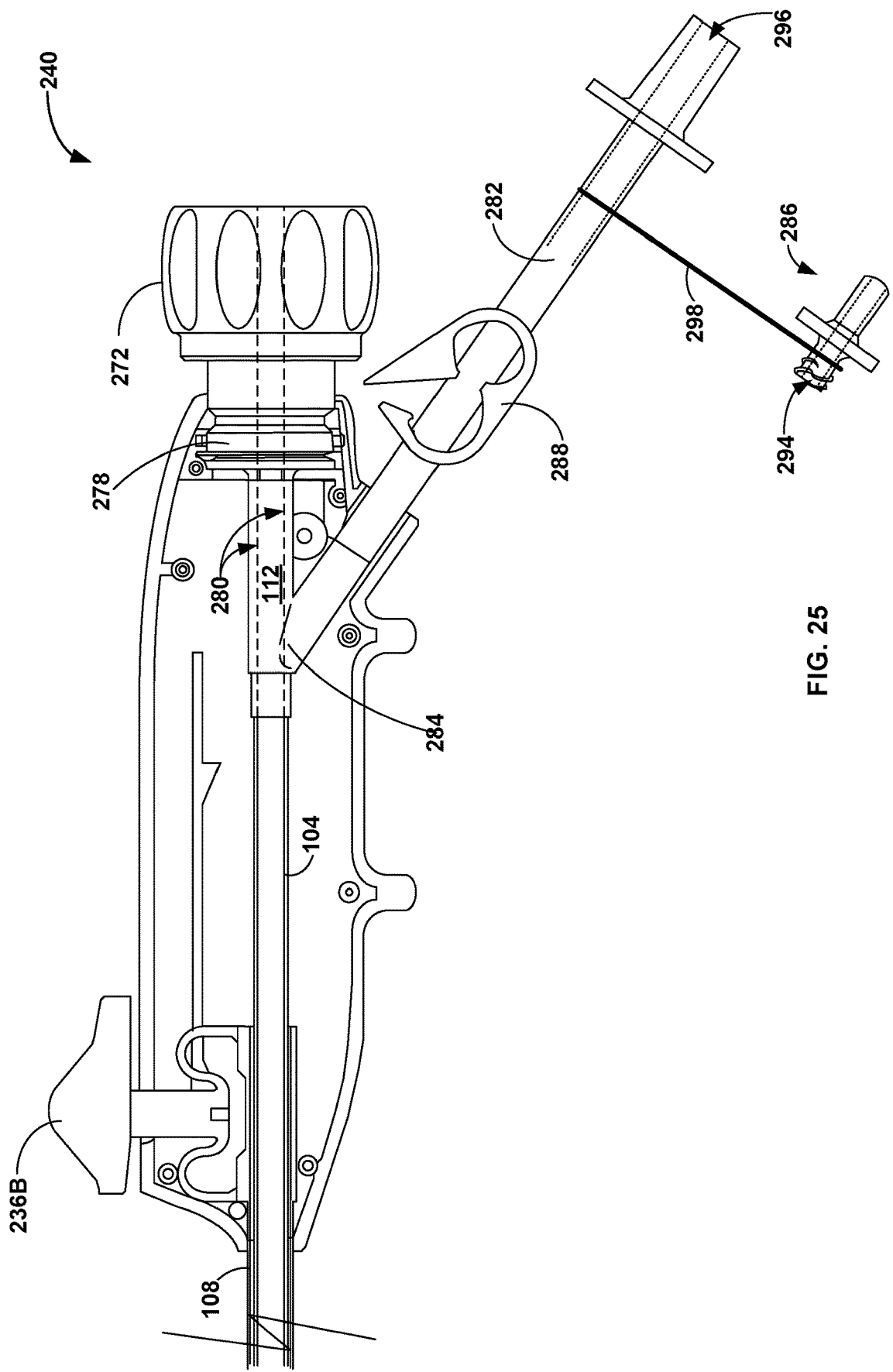
FIG. 25 is a schematic cross-sectional view of a proximal portion of an example of the retrieval catheter assembly of the catheter assembly of FIGS. 23A and 23B.

FIGS. 23A-25 illustrate an example catheter assembly 230 including handles including one or more of the aforementioned features. FIG. 23A is a conceptual side elevation view of the catheter assembly 230, which includes the thrombus removal device 10, a delivery catheter assembly 400, and a retrieval catheter assembly 500. FIG. 23B is a conceptual side view of the catheter assembly of FIG. 23A and illustrates a delivery catheter handle and a retrieval catheter handle connected together. FIG. 24 is a schematic cross-sectional view of an example of a proximal portion of the delivery catheter assembly 400. FIG. 25 is a schematic cross-sectional view of an example of a proximal portion of the retrieval catheter assembly 500. The catheter assembly 230 is an example of the catheter assembly 100 of FIG. 10, except for the differences noted herein. The delivery catheter 102 of the delivery catheter assembly 400 is an example of the delivery catheter 102 of FIGS. 2A and 10, and the retrieval catheter 104 of the retrieval catheter assembly 500 is an example of the retrieval catheter 104 of FIGS. 2A and 10.

The delivery catheter assembly 400 includes a delivery catheter handle 232, and a delivery catheter 102 defining a delivery catheter lumen 110. The delivery catheter lumen 110 is configured to contemporaneously receive the expandable element 14 and part of the elongated support member 12 of the thrombus removal device 10. When the expandable element 14 is positioned within the delivery catheter lumen 110, the walls of the delivery catheter 102 apply a compressive force to the expandable element 14 to hold the expandable element in a relatively low-profile delivery configuration.

The delivery catheter handle 232 includes a delivery catheter actuator 236A configured to control expansion and contraction of the expandable element 14 of the thrombus-removal device 10. For example, the delivery catheter actuator 236A is mechanically coupled to the delivery catheter 102, such that movement of the delivery catheter actuator 236A causes longitudinal movement of the delivery catheter 102 (along a longitudinal axis of the delivery catheter 102). To deploy the expandable element 14 from the delivery catheter 102, a clinician may manipulate the delivery catheter actuator 236A, such as by sliding the delivery catheter actuator 236A within a channel 250 defined by a housing 252 of the delivery catheter handle 232, by rotating a thumbwheel, or the like, in order to proximally withdraw the delivery catheter 102 relative to the expandable element 14, e.g., while holding the expandable element 14 in place or nearly in place via the elongated support member 12 and/or while also pushing the expandable element 14 from the delivery catheter lumen 110 by applying a pushing force to a proximal portion of the elongated support member 12.

As detailed further below, the delivery catheter actuator 236A defines a proximal portion of a fluid pathway extending through at least a portion of the delivery catheter 102.

The retrieval catheter assembly 500 includes a retrieval catheter 104, a retrieval funnel 106 located at a distal portion of the retrieval catheter 104, a retrieval catheter handle 240 located at a proximal portion of retrieval catheter 104, and a cover sheath 108 disposed radially outward of the retrieval catheter 104. The cover sheath 108 is an example of the cover sheath 108 shown in FIG. 10, and is configured to apply a compressive force to the funnel 106 to hold the funnel 106 in a lower profile configuration.

The retrieval catheter handle 240 includes a retrieval catheter actuator 236B configured to control expansion and contraction of the retrieval funnel 106. For example, in some examples, the retrieval catheter actuator 236B is mechanically coupled to the cover sheath 108, such that movement of the retrieval catheter actuator 236B causes movement of the cover sheath 108. To deploy the funnel 106 from the cover sheath 108, a clinician may manipulate the retrieval catheter actuator 236B, such as by sliding the retrieval catheter actuator 236B within a channel defined by a housing of the retrieval catheter handle 240, rotating a thumbwheel, or the like, in order to proximally withdraw the cover sheath 108 relative to the funnel 106, e.g., while holding the funnel 106 in place or nearly in place and/or while also pushing the funnel 106 from the cover sheath 108. Once the cover sheath 108 is proximally withdrawn so that it no longer covers the funnel 106, the funnel 106 may expand radially outward into the funnel shape shown in FIG. 10.

As detailed further below, the retrieval catheter handle 240 is configured to removably couple to the delivery catheter handle 232, which may provide one or more benefits during a thrombus-removal procedure. FIG. 24 illustrates an example of a proximal portion of the delivery catheter assembly 400, which includes the delivery catheter 102 defining the delivery catheter lumen 110, the delivery catheter actuator 236A, and a delivery catheter handle 232 having a delivery catheter handle housing 252. In the example shown in FIG. 24, the delivery catheter actuator 236A includes a slider mechanism (also referred to herein as "delivery catheter slider 236A") configured to slide in a proximal direction (e.g., to the right, from the perspective of FIG. 24) within a slider channel 250 in order to enable expansion of the expandable element 14, and to slide in a distal direction (e.g., to the left, from the perspective of FIG. 24) within the slider channel 250 in order to cause contraction of the expandable element 14. For example, delivery catheter 102 can be directly or indirectly connected to the delivery catheter slider 236A at a junction 290, such that proximal movement of the delivery catheter slider 236A causes proximal movement of the delivery catheter 102, and distal movement of the delivery catheter slider 236A causes distal movement of the expandable element 14.

When the expandable element 14 is positioned within the delivery catheter lumen 110, the walls of the delivery catheter 102 apply a compressive force to the expandable element 14 to hold the expandable element in a relatively low-profile "delivery" configuration. In some such examples, the delivery catheter slider 236A is configured to move proximally within the slider channel 250 in order to proximally retract the delivery catheter 102 from overtop of the expandable element 14, thereby enabling the expandable element 14 to self-expand. Conversely, a user (e.g., a clinician) may actuate the delivery catheter slider 236A in a distal direction within the channel 250 to re-position the delivery catheter 102 overtop of the expandable element 14, thereby compressing the expandable element 14 into a collapsed, compressed, or contracted configuration, as detailed further above.

The delivery catheter slider 236A can have any suitable configuration. In some examples, the delivery catheter slider 236A is a push-activated slider. For example, the delivery catheter slider 236A may be biased upward (e.g., radially outward from the central longitudinal axis 270), such that a user must push downward (e.g., toward the central longitudinal axis 270) to enable the slider to slide proximally and/or distally within the channel 250.

The delivery catheter actuator 236A defines a proximal portion (including a proximal-most end 244) of a fluid pathway 246 that extends through at least a portion of the delivery catheter 102. For example, as shown in FIG. 24, the slider 236A includes a user-input mechanism 248 (e.g., a button) located external to the delivery catheter handle housing 252 of the handle 232; a fluid-infusion port 254 extending outward through the housing 252; and an interior member 256 located within the housing 252. The interior member 256 defines an actuator lumen 258 that is fluidically coupled to the interior lumen of the fluid-infusion port 254, and also fluidically coupled to the delivery catheter lumen 110. Because the delivery catheter 102 is disposed radially outward of the elongated support member 12 (e.g., the elongated support member 12 is located within the delivery catheter lumen 110 and within the handle lumen 262), any fluid traveling through the delivery catheter lumen 110 is restricted to the volume 246 located radially between the exterior surface of the elongated support member 12 and the interior surface of the delivery catheter 102. The actuator lumen 258 of the interior member 256 is fluidically coupled to the delivery catheter lumen 110, and therefore defines a proximal portion of the fluid pathway 246. The fluid pathway 246 therefore includes the actuator lumen 258 of the interior member 256 of the delivery catheter actuator 236A and the delivery catheter lumen 110. In examples in which the elongated support member 12 has been removed from the lumen 110 of the delivery catheter 102, the full volume of the actuator lumen 258 and the delivery catheter lumen 110 define the fluid pathway 246.

The proximal portion of the fluid pathway 246 (or equivalently, the actuator lumen 258) terminates at a proximal end 244 located within the interior member 256 of the delivery catheter actuator 236A. The proximal end 244 provides an opening configured to receive the elongated support member 12, wherein the opening forms a fluid-tight seal around the exterior surface of the elongated support member 12, preventing fluid received via the fluid-infusion port 254 from leaking proximally past the delivery catheter actuator 236A. For example, the interior member 256 of delivery catheter actuator 236A may include an O-ring 292 or other fluid tight seal that prevents fluid from moving proximally, but that still permits longitudinal movement of the delivery catheter 102 overtop of, and relative to, the elongated support member 12.

As discussed above with respect to FIG. 11B, in some examples, a clinician may deliver a therapeutic agent or another fluid through the delivery catheter lumen 110 during a medical procedure. The fluid may be, for example, released through a plurality of openings 264 (FIG. 23A) defined by the delivery catheter 102. In examples in which the delivery catheter actuator 236A defines part of the fluid pathway 246, a clinician may introduce the fluid via the fluid-infusion port 254, where it may enter the fluid pathway 246 and exit outward from the openings 264, e.g., into the vasculature of a patient, to at least partially break down the thrombus material.

An effective length of the fluid pathway 246 may be defined as the length of the portion of the delivery catheter 102 that extends distally outward from the delivery catheter handle 232. Accordingly, the effective length of the fluid pathway 246 changes (e.g., increases or decreases) based on a relative location of the slider 236A within the slider channel 250. While the slider 236A is in a proximal position within the slider channel 250, the effective length of the fluid pathway is shorter than it is while the slider 236A is in a distal position within the slider channel 250. Accordingly, a clinician is able to control an axial or longitudinal location within the patient's vessel at which to release a fluid by manipulating an axial position of the openings 264 via the slider 236A.

In some examples, such as in the example shown in FIG. 23A, the fluid-infusion port 254 may extend outward through a side opening 266 defined by the delivery catheter handle housing 252. In other examples, such as the example shown in FIG. 24, the fluid-infusion port 254 may extend outward through the same opening 268 as the user-input mechanism 248 of the slider 236A, located on a top surface of the delivery catheter handle housing 252. This example configuration, wherein the fluid-infusion port 254 is fluidically coupled to the slider 236A, may provide one or more benefits because the fluid-infusion port 254 does not require a separate opening within the housing 252 of the delivery catheter handle 232. This may simplify manufacture and provide one less point of potential fluid leakage from the delivery catheter handle housing 252.

As shown in FIG. 24, in some such examples, the fluid-infusion port 254 may be oriented at an oblique angle relative to a central longitudinal axis 270 of the delivery catheter 102 (versus a 90 degree angle). This oblique orientation of the fluid-infusion port 254 reduces an overall footprint of the delivery catheter assembly 400 and/or the overall catheter assembly 230 (as compared to examples in which the fluid-infusion port 254 is oriented perpendicularly to the central longitudinal axis 270), which may help reduce costs associated with product packaging, storage, and shipment. Further, this oblique orientation of the fluid-infusion port 254 provides improved port access for the user of the delivery catheter assembly 400, because the fluid-infusion port 254 is aligned with the central longitudinal axis 270, as viewed from the perspective of a user positioned generally proximal to the delivery catheter handle 232.

FIG. 25 illustrates a proximal portion of an example of the retrieval catheter assembly 500 of FIG. 23A, and illustrates the retrieval catheter 104, the cover sheath 108, and the retrieval catheter handle 240, which includes the retrieval catheter actuator 236B configured to control expansion and contraction of the retrieval funnel 106. For example, the retrieval catheter actuator 236B may include a slider mechanism (also referred to herein as the "retrieval catheter slider 236B") configured to slide in a proximal direction (e.g., to the right, from the perspective of FIG. 25) to enable expansion of the retrieval funnel 106, and to slide in a distal direction (e.g., to the left, from the perspective of FIG. 25) to cause contraction of the retrieval funnel 106. For example, the cover sheath 108 can be directly or indirectly connected to the retrieval catheter actuator 236B, such that actuation of the retrieval catheter actuator 236B causes movement of the outer sheath 108. For example, the retrieval catheter slider 236B can be configured to move proximally to proximally retract the cover sheath 108 from overtop of the funnel 106, thereby enabling the funnel 106 to self-expand. Conversely, a user (e.g., a clinician) may move the retrieval catheter slider 236B in a distal direction to cause distal movement of the cover sheath 108 to reposition the cover sheath 108 overtop of the funnel 106, thereby compressing the funnel 106 into a collapsed, compressed, or contracted configuration.

In some examples, the retrieval catheter handle 240 defines an aspiration port 282. The aspiration port 282 is configured to connect to a suction source, such as an aspiration pump, a syringe, or the like, in order to aspirate a thrombus through the retrieval catheter lumen 112. The inner lumen 296 of the aspiration port 282 is fluidically coupled to the retrieval catheter lumen 112 (e.g., the portion of the lumen 112 of the retrieval catheter 104 located within the retrieval catheter handle 240), via a Y-shaped connector 284, as shown in FIG. 25. A larger-bore aspiration lumen 296 may enable more-efficient aspiration of thrombus material. For example, the larger bore aspiration lumen may distribute aspiration forces over a larger surface area. However, the larger-bore aspiration lumen 296 may be incompatible with another device used during the thrombus-removal procedure, such as a syringe used to introduce a liquid contrast agent or a flushing fluid into the retrieval catheter lumen 112 via the aspiration port 282.

In some examples, the aspiration port 282 of the retrieval catheter handle 240 includes a modifiable inner diameter, enabling variable sized devices to fluidically couple to the retrieval catheter lumen 112. For example, the aspiration port 282 of the retrieval catheter handle 240 can be configured to fluidically connect to (and in some examples, secure to, such as by threads) at least two different-sized syringes, such as a larger-bore syringe (e.g., 30 cubic centimeters (cc) to 60 cc) for aspiration, and a smaller-bore syringe (e.g., 1 cc to 20 cc, such as 1 cc, 3 cc, or 10 cc) to enable fluid-injection applications via the aspiration port 282. The larger bore syringe may be, for example, non-standard and may require a more specialized connector than the smaller-bore syringe. Accordingly, retrieval catheter handle 240 is adaptable to multiple different fluidic applications, for example, abrogating the requirement for a specialized (e.g., larger-bore) syringe for lumen flushing and/or contrast-agent delivery.

For example, as shown in FIGS. 23A and 25, in some examples, the retrieval catheter handle 240 includes a removable adaptor 286 configured to be introduced into the aspiration port 282 to convert the aspiration port 282 into a smaller-bore fluid port. The removable adaptor 286 defines an inner lumen 294 that has a smaller inner diameter (e.g., a smaller-bore) than the inner lumen 296 of the aspiration port 282. In some such examples, the lumen 294 of the removable adaptor 286 may be sized (e.g., with respect to its inner diameter) to receive a standard-gauge fluid delivery syringe. For example, while the removable adaptor 286 is installed within the aspiration port 282, a clinician may connect a standard-gauge syringe to the aspiration port 282 to deliver a fluid (e.g., a flushing fluid or a contrast agent) into the retrieval catheter lumen 112. The removable adaptor 286, while installed within the aspiration port 282, is configured to convert the aspiration port 282 into a fluid-infusion port configured to receive fluid via a standard-gauge syringe. While the removable adaptor 286 is not installed within the aspiration port 282, the clinician may use a large-bore syringe, which may be included as a component of the catheter assembly 230 in some examples, to aspirate the thrombus, e.g., by connecting the larger-bore syringe directly to the aspiration port 282.

In some examples, the adaptor 286 is tethered to the aspiration port 282 via a tether 298 to prevent the removable adaptor 286 from being separated from the retrieval catheter handle 240 and lost. In other examples, the adaptor 286 may be separated from the catheter assembly 230, e.g., once disconnected from the aspiration port 282, the adaptor 286 may be discarded, rather than remaining connected via the tether 298.

In some examples, the retrieval catheter handle 240 is configured to removably couple to the delivery catheter handle 232, which may improve one or more aspects of a thrombus-removal procedure. For example, by temporarily rigidly interconnecting the two handles, as illustrated in FIG. 23B, a clinician may be able to perform one or more parts of a thrombus-removal procedure (e.g., navigation of a distal portion of the catheter assembly 230 to a target site within vasculature of a patient) with just a single hand, leaving the clinician's other hand free to perform other tasks. For example, the clinician may use one hand to secure an introducer sheath in place at the opening to the patient's vasculature, and use the other hand to maneuver the catheter assembly 230. With some other catheter assemblies having handles that do not interconnect, the clinician is required to manipulate each handle 232, 240 with a different hand, thereby complicating the procedure. The clinician may subsequently decouple the handles 232, 240 for other parts of the medical procedure, such as to remove the delivery catheter 102 from the retrieval catheter lumen 112.

The interlocking catheter handles 232, 240 enable one-handed manipulation of the catheter assembly 230 without applying excessive stress loads on the center lumens of the catheters 102, 104. For example, interlocking the handles 232, 240 at a junction located between the handles (e.g., distal end of the delivery catheter handle 232 and at a proximal end of the retrieval catheter handle 240), can reduce or even eliminate a risk of the retrieval catheter handle 240 bending relative to the delivery catheter handle 232 at this junction while the delivery catheter 102 is located within the lumen 112 of the retrieval catheter 104. In such examples, the retrieval catheter handle 240 would otherwise be able to apply a bending force to the portion of the delivery catheter 102 and, if present, the portion of the elongated support member 12 located within the retrieval catheter handle 240, thereby potentially kinking, or otherwise adversely impacting the structural integrity of the delivery catheter 102 and/or the elongated support member 12. A rigid connection between the handles 232, 240 effectively eliminates this junction altogether, thereby preventing a potentially excessive stress load from applied to the delivery catheter 102.

The interconnected handles 232, 240 can also provide for a longer, more-rigid body than either of the catheter handles alone, which may increase the ease with which a user may manipulate the connected handles. As another example, while the handles 232, 240 are in an interlocked configuration, the combined handles 232, 240 provide a relatively large, rigid structure for the clinician to easily grasp instead of (e.g., incidentally) grasping exposed portions of the more-vulnerable delivery catheter 102 and/or cover sheath 108 directly.

In the example depicted in FIGS. 23A and 25, a proximal portion (e.g., a proximal-most end) of the retrieval catheter handle 240 includes a connection mechanism 272 configured to receive and retain a distal portion of the delivery catheter handle 232. In other examples, the connection mechanism 272 (also referred to herein as the "connector 272") may be rigidly coupled to the distal portion of the delivery catheter handle 232, and configured to removably receive and retain a proximal portion of the retrieval catheter handle 240. In other examples, both a proximal portion of the retrieval catheter handle 240 and a distal portion of the delivery catheter handle 232 may include respective connection mechanisms that are configured to interconnect with one another.

In some examples in which the connector 272 is configured to receive and retain a distal portion of the delivery catheter handle 232, the distal portion of the delivery catheter handle 232 may include a tapered distal extension 274 (FIG. 24) configured to be received and retained within the connector 272 in order to interlock the delivery catheter handle 232 and the retrieval catheter handle 240. In some examples, the distal extension 274 includes a with a protrusion 276 that mates with a part of the delivery retrieval catheter handle 240. The distal extension 274, defined by the rigid handle housing 252 can further contribute to the rigidity of the connected handles when the distal extension 274 is received and secured within the connector 272 (e.g., in the configuration illustrated in FIG. 23B), thereby further reducing stress loads applied to the catheters 102, 104. As one non-limiting example, this rigidity (e.g., a resistance to the distal extension 274 accidentally falling out of the connector 272 in response to a typical applied force) may be achieved when the distal extension 274 is about 0.5 inches or more (e.g., about 1.25 cm) long, as measured in an axial direction parallel to the central longitudinal axis 270. At longer axial lengths, the distal extension 274 occupies (e.g., reduces) the working length of the catheter assembly, and by extension, the compatibility of the catheter assembly with a given length of guidewire introduced through the catheter assembly.

The taper of the distal extension 274 may enable the handles 232, 240, when connected, to define similar outer perimeters to enable the connected handles 232, 240 to define a relatively smooth transition between the handles 232, 240. For example, the outer cross-sectional shapes and sizes of the handles 232, 250 can be selected such that the connected handles 232, 240 define a relatively continuous outer surface. This can, for example, help improve the user experience by providing a relatively smooth and uniform handle surface for the catheter assembly 230, the handle surface being defined by the connected handles 232, 240.

In some examples, the distal extension 274 of the delivery catheter handle 232 may include one or more protrusions (e.g., knobs or tabs) extending radially outward from the central longitudinal axis 270. For example, the distal extension 274 can include two protrusions 276 180 degrees apart from each other, e.g., at "3 o'clock" and "9 o'clock"

positions. In some such examples, the protrusions 276 may slide into receiving portions (e.g., slots) of the connector 272 of the retrieval catheter handle 240 and lock the two handles 232, 240 together via a 90-degree rotation of the connector 272. In some such examples, the receiving slots of the connector 272 may be inclined or "ramped," such that the rotation of the connector 272 also distally withdraws the delivery catheter handle 232 into the connector 272 to provide an interference fit.

The connector 272 can have any suitable configuration that enables temporary connection of the delivery catheter handle 232 and the retrieval catheter handle 240, e.g., during navigation of the catheter assembly 230 through vasculature of a patient, and then subsequent disconnection of the delivery catheter handle 232 and the retrieval catheter handle 240 to enable removal of the delivery catheter 102 from the patient. For example, as depicted in FIGS. 23A and 25, the connector 272 may include a Tuohy-Borst-type adaptor valve, configured to rotate relative to the rest of the retrieval catheter handle 240 in order to interlock radially inward (e.g., toward the central longitudinal axis 270) onto the delivery catheter 102. In some examples, the Tuohy-Borst-type adaptor may be modified in order to interconnect with the distal end of the delivery catheter handle 232. The Tuohy-Borst-type connection may include a compressible sealing mechanism that can seal over many different sized and/or different-shaped elements, enabling customization over which particular component the connector 272 is directly sealed onto. For example, the compressible sealing mechanism can enable the retrieval catheter handle 240 to form a fluid tight seal around the delivery catheter 102, the delivery catheter handle distal extension 274, a guidewire 15 (FIG. 1), or another component.

In some examples, the connector 272 is threaded such that, when the connector 272 is rotated (e.g., "screwed in"), the connector 272 is configured to compress radially inward on (e.g., fluidically seal) the Tuohy-Borst valve, and by extension, the portion of the delivery catheter handle 232 or other component that is received within the valve. This type of connection may provide a fluid tight seal to enable aspiration of a thrombus from the retrieval catheter lumen 112 via the aspiration port 282, as described above.

Additionally or alternatively, the connector 272 may include a bayonet-type interlocking mechanism, in which the distal portion of the delivery catheter handle 232 is received within the connector 272, and then "locked" into place within the connector 272 via a quarter-turn (or other fraction of a revolution) around the central longitudinal axis 270 (FIG. 24). In some such examples, a user may twist the two handles 232, 240 relative to each other in order to lock them together, and then may rotate the connector 272 (e.g., a Tuohy-Borst valve) in order to provide the fluid-tight seal at the junction between the two handles 232, 240.

In some examples, but not all examples, the connector 272 includes two symmetrical components (e.g., generally semi-cylindrical components) configured to snap together or otherwise mutually interlock in order to form the connector 272. Such examples may help reduce both the number of "unique" components of the catheter assembly 230 and the number of required thermal or adhesive bonds within the catheter assembly 230, thereby reducing the cost of production.

In some examples, the connector 272 includes a sealing member 278. When the delivery catheter 102 is received within the retrieval catheter lumen 112 (e.g., as shown in FIG. 23A), and when the delivery catheter handle 232 is coupled to the retrieval catheter handle 240 via the connector 272, the sealing member 278 is configured to form a fluid-tight seal within a space or volume located radially between an exterior surface of the delivery catheter 102, and radially inward from an interior surface 280 of the of the retrieval catheter 104.

Figure 26:
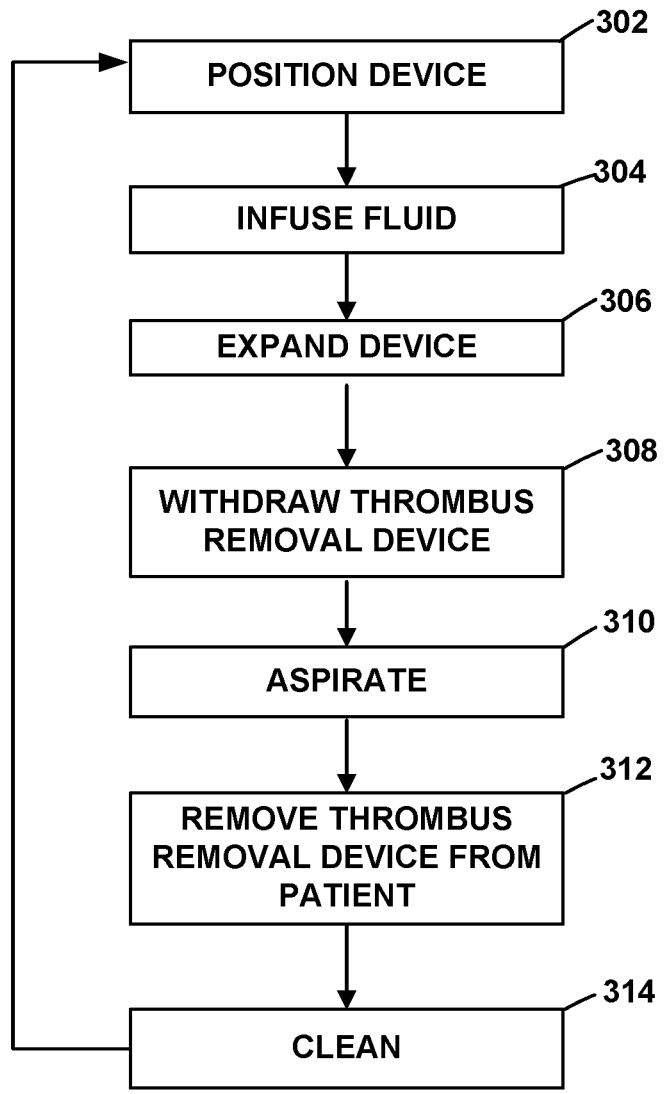
FIG. 26 is a flow diagram of an example method of removing a thrombus from vasculature of a patient using an example catheter assembly described herein.

FIG. 26 is a flow diagram of an example method of removing a thrombus from vasculature of a patient using an example catheter assembly as described herein. The technique of FIG. 26 is described primarily with respect to the catheter assembly 230 of FIGS. 23A-25, however, the techniques may be performed with any suitable thrombus-removal device and catheter assembly.

A clinician may access a blood vessel of a patient, wherein the blood vessel includes a partial or total blockage, such as a thrombus. For example, the clinician may create an incision into the blood vessel and at least partially insert an introducer sheath into the blood vessel to create a pathway for the catheter assembly 230. In some examples, the clinician inject a contrast fluid through the introducer sheath in order to enable visualization of the target vasculature. The clinician may insert a guidewire through the introducer sheath and into the blood vessel to the thrombus.

The clinician may prepare the catheter assembly 230. For example, the clinician may flush all lumens of the catheter assembly 230 with saline or another sanitizing fluid, such as while the delivery catheter handle 232 is locked to the retrieval catheter handle 240 via the connector 272, such that the clinician may use one hand to handle the catheter assembly 230, and the other hand to introduce the saline into the various lumens. For example, the clinician may introduce the saline through the fluid-infusion port 254 on the delivery catheter handle 232, which is fluidically coupled to the delivery catheter lumen 110 via an actuator lumen 258 of the actuator 236A. Additionally or alternatively, the clinician may insert the removable adaptor 286 into the aspiration port 282 of the retrieval catheter handle 240, and introduce the saline through the aspiration port 282 using a syringe. Additionally or alternatively, the clinician may introduce the fluid through the guidewire port 300 at a proximal-most end of the delivery catheter handle 232.

The clinician may interlock a distal portion of the delivery catheter handle 232 to a proximal portion of the retrieval catheter handle 240 via a connection mechanism 272. For example, the clinician may insert the distal portion of the delivery catheter handle 232 into the connector 272 and then rotate the connector 272 to form a fluid-tight seal against an outer surface of the delivery catheter 102. The clinician may also advance the delivery catheter actuator 236A and the retrieval catheter actuator 236B distally forward, thereby causing the delivery catheter 102 to collapse the expandable element 14, and similarly, causing the cover sheath 108 to collapse the retrieval funnel 106 into their respective collapsed configurations. In other examples, the catheter assembly 230 may be preconfigured by the manufacturer or other entity such that the handles 232, 240 are locked together, such that the expandable element 14 is collapsed within the delivery catheter 102, and/or such that the retrieval funnel 106 is covered by the cover sheath 108.

In accordance with the technique shown in FIG. 26, the clinician positions the thrombus-removal device 10 relative to the thrombus within vasculature of a patient (302). For example, the clinician may insert a distal end of the catheter assembly 230 through an introducer sheath and advance the distal end of the catheter assembly 230 through the patient's blood vessel (e.g., a vein) until the expandable element 14 is located on a distal side of the thrombus, and the retrieval funnel 106 is located on a proximal side of the thrombus.

In some examples, but not all examples, the clinician may infuse a therapeutic agent or other fluid into the catheter assembly 230 (304). For example, the clinician may insert the distal tip of a syringe containing a fluid, such as a lytic agent, into a fluid-infusion port 254 of the delivery catheter handle 232. The fluid will travel through the fluid path 246 and outward from the openings 264 defined by the delivery catheter 102.

The clinician may then expand the expandable element 14 and the retrieval funnel 106 of the thrombus-removal device 10 (306). For example, the clinician may depress and proximally move the retrieval catheter actuator 236B in order to withdraw the cover sheath 108 from overtop of the retrieval funnel 106, thereby enabling the funnel 106 to self-expand into an expanded configuration on the proximal side of the thrombus. Similarly, the clinician may depress and proximally move the delivery catheter actuator 236A in order to withdraw the delivery catheter 102 from overtop of the expandable element 14, thereby enabling the expandable element 14 to self-expand into an expanded configuration on the distal side of the thrombus.

The clinician may then proximally withdraw the expandable element 14 through the thrombus (308). For example, the clinician may rotate the connector 272 to uncouple the delivery catheter handle 232 from the retrieval catheter handle 240. While stabilizing the retrieval catheter handle 240 in place, the clinician may proximally withdraw the delivery catheter 102, including the expandable element 14, proximally through the thrombus and into the retrieval funnel 106.

In some examples, but not all examples, the clinician may aspirate the thrombus (310). For example, the clinician may rotate the connector 272 to fluidically seal the connector 272 onto the delivery catheter 102, or in some cases, completely closed on itself, such as when the delivery catheter 102 has been fully removed from the patient's body and from the retrieval catheter 104. The clinician may close a tube clamp 288 (FIG. 25) onto the aspiration port 282 in order to seal the aspiration port 282 fluidically closed (e.g., in examples in which the tube clamp 288 is not already closed). The clinician may either connect an aspiration source (e.g., a syringe or a pump) directly to the aspiration port 282, or, after installing the removable adaptor 286 in other examples. The clinician may then open the tube clamp 288 to create a vacuum within the cover sheath 108.

The clinician may proximally withdraw the thrombus removal device 10 from the patient, e.g., by proximally withdraw the delivery catheter 102 from the patient. In some examples, the clinician cleans (e.g., rinses in saline) the expandable element 14 in order to remove fragments of the thrombus (312) and reintroduces the thrombus removal device 10 into the vasculature via the retrieval catheter 12 to repeat part of the technique shown in FIG. 26. For example, the clinician may inject more contrast fluid through the introducer sheath to observe the remaining amount of thrombus within the blood vessel. If an above-threshold amount of thrombus material remains within the patient's vein, then the clinician may re-load the thrombus-removal device 10 and prepare the catheter assembly 230 for another pass through the thrombus (302).

Various examples have been described. These and other examples are within the scope of the following claims.

What is claimed is:

1. A catheter assembly comprising:
   a delivery catheter;
   an expandable element;
   a delivery catheter handle connected to the delivery catheter;
   a retrieval catheter including a distal portion with a retrieval funnel, the retrieval catheter defining a retrieval catheter lumen configured to receive the delivery catheter; and
   a retrieval catheter handle connected to the retrieval catheter, wherein a proximal end of the retrieval catheter handle is configured to removably couple to a distal end of the delivery catheter handle by at least directly interlocking with the distal end of the delivery catheter handle,
   wherein the retrieval catheter defines a retrieval catheter central longitudinal axis,
   wherein the retrieval funnel includes a proximal funnel portion defining a first taper angle and a distal funnel portion extending from the proximal funnel portion to a distalmost end of the retrieval funnel, the distal funnel portion defining a second taper angle,
   wherein the first taper angle and the second taper angle are relative to the retrieval catheter central longitudinal axis,
   wherein the second taper angle is constant along the distal funnel portion, and
   wherein the second taper angle is greater than the first taper angle such that the proximal funnel portion is configured to apply a greater compressive force to the expandable element than the distal funnel portion when the expandable element is retracted proximally into the retrieval funnel.

2. The catheter assembly of claim 1, wherein the proximal end of the retrieval catheter handle comprises a connector configured to receive the distal end of the delivery catheter handle to removably couple the retrieval catheter handle to the delivery catheter handle.

3. The catheter assembly of claim 2, wherein the distal end of the delivery catheter handle comprises an extension including at least one protrusion configured to be received within the connector.

4. The catheter assembly of claim 3, where the delivery catheter handle defines a central longitudinal axis, and wherein the at least one protrusion extends radially outward from the central longitudinal axis.

5. The catheter assembly of claim 3, wherein the extension of the delivery catheter handle circumferentially surrounds the delivery catheter.

6. The catheter assembly of claim 2, wherein the connector comprises a sealing member configured to form a fluid-tight seal with an exterior surface of the delivery catheter when the delivery catheter is received within the retrieval catheter lumen and when the delivery catheter handle is coupled to the retrieval catheter handle.

7. The catheter assembly of claim 1, wherein the delivery catheter handle comprises an actuator configured to cause movement of the delivery catheter along a longitudinal axis of the delivery catheter, and wherein the actuator defines an actuator lumen that is fluidically coupled to a delivery catheter lumen defined by the delivery catheter.

8. The catheter assembly of claim 7, wherein the expandable element is configured to be received within the delivery catheter lumen defined by the delivery catheter, wherein the actuator comprises a slider configured to slide proximally to enable expansion of the expandable element and to slide distally to cause the contraction of the expandable element.

9. The catheter assembly of claim 1, wherein the retrieval catheter handle defines an aspiration port, and wherein the retrieval catheter handle comprises a removable adaptor configured to convert the aspiration port into a smaller-bore port.

10. The catheter assembly of claim 9, further comprising a tether connecting the removable adaptor to the retrieval catheter handle.

11. The catheter assembly of claim 9, wherein the retrieval catheter handle comprises a Y-connector that fluidically couples the aspiration port to the retrieval catheter lumen.

12. The catheter assembly of claim 1, wherein coupling the proximal end of the retrieval catheter handle to the distal end of the delivery catheter handle reduces bending of the delivery catheter by the retrieval catheter handle.

13. A catheter assembly comprising:
- a delivery catheter defining a delivery catheter lumen;
- an expandable element configured to be received within the delivery catheter lumen,
wherein the expandable element is configured to receive a thrombus;
- a delivery catheter handle connected to the delivery catheter, the delivery catheter handle comprising an actuator configured to cause expansion and contraction of the expandable element, wherein the actuator defines an actuator lumen that is fluidically coupled to the delivery catheter lumen;
- a retrieval catheter including a distal portion with a retrieval funnel, the retrieval catheter defining a retrieval catheter lumen configured to receive the delivery catheter;
- a retrieval catheter handle connected to the retrieval catheter; and
- a cover sheath disposed over the retrieval funnel, wherein the cover sheath is configured to be proximally retracted relative to the retrieval funnel to enable expansion of the retrieval funnel,
wherein the retrieval catheter defines a retrieval catheter central longitudinal axis,
wherein the retrieval funnel includes a proximal funnel portion defining a first taper angle and a distal funnel portion extending from the proximal funnel portion to a distalmost end of the retrieval funnel, the distal funnel portion defining a second taper angle,
wherein the first taper angle and the second taper angle are relative to the retrieval catheter central longitudinal axis,
wherein the second taper angle is constant along the distal funnel portion, and
wherein the second taper angle is greater than the first taper angle such that the proximal funnel portion is configured to apply a greater compressive force to the expandable element than the distal funnel portion when the expandable element is retracted proximally into the retrieval funnel.

14. The catheter assembly of claim 13, wherein the actuator comprises a user-input mechanism and an interior member defining the actuator lumen.

15. The catheter assembly of claim 13, wherein the actuator is configured to retract the delivery catheter from overtop of the expandable element to enable the expansion of the expandable element.

16. The catheter assembly of claim 15, wherein the actuator further comprises a fluid-infusion port fluidically coupled to the delivery catheter lumen, and wherein the delivery catheter defines a plurality of openings configured to release a fluid received through the fluid-infusion port.

17. The catheter assembly of claim 16, wherein the fluid-infusion port is oriented at an oblique angle to a central longitudinal axis of the delivery catheter handle.

18. The catheter assembly of claim 13, wherein the actuator comprises a slider configured to slide proximally to enable expansion of the expandable element and to slide distally to cause contraction of the expandable element.

19. The catheter assembly of claim 13,
wherein the actuator comprises a delivery catheter actuator, and
wherein the retrieval catheter handle comprises a retrieval catheter actuator configured to cause expansion and contraction of the retrieval funnel.

20. The catheter assembly of claim 19, wherein the retrieval catheter actuator is configured to proximally retract the cover sheath relative to the retrieval funnel to enable the expansion of the retrieval funnel.

21. A catheter assembly comprising:
- a delivery catheter defining a delivery catheter lumen extending along a longitudinal axis;
- an expandable element;
- a delivery catheter handle connected to the delivery catheter, wherein the delivery catheter handle comprises an actuator configured to cause movement of the delivery catheter along the longitudinal axis, wherein the actuator defines an actuator lumen that is fluidically coupled to the delivery catheter lumen;
- a retrieval catheter including a distal portion with a retrieval funnel, the retrieval catheter defining a retrieval catheter lumen configured to receive the delivery catheter; and
- a retrieval catheter handle connected to the retrieval catheter, wherein a proximal end of the retrieval catheter handle is configured to removably couple to a distal end of the delivery catheter handle by at least directly interlocking with the distal end of the delivery catheter handle,
wherein the retrieval catheter defines a retrieval catheter central longitudinal axis,
wherein the retrieval funnel includes a proximal funnel portion defining a first taper angle and a distal funnel portion extending from the proximal funnel portion to a distalmost end of the retrieval funnel, the distal funnel portion defining a second taper angle,
wherein the first taper angle and the second taper angle are relative to the retrieval catheter central longitudinal axis,
wherein the second taper angle is constant along the distal funnel portion, and
wherein the second taper angle is greater than the first taper angle such that the proximal funnel portion is configured to apply a greater compressive force to the expandable element than the distal funnel portion when the expandable element is retracted proximally into the retrieval funnel.

22. The catheter assembly of claim 21, wherein the proximal end of the retrieval catheter handle comprises a connector configured to receive the distal end of the delivery catheter handle to removably couple the retrieval catheter handle to the delivery catheter handle.

23. The catheter assembly of claim 22, wherein the connector comprises a sealing member configured to form a fluid-tight seal with an exterior surface of the delivery catheter when the delivery catheter is received within the retrieval catheter lumen and when the delivery catheter handle is coupled to the retrieval catheter handle.

24. The catheter assembly of claim 21, wherein the actuator comprises a user-input mechanism and an interior member defining the actuator lumen that is fluidically coupled to the delivery catheter lumen.

25. The catheter assembly of claim 21, wherein the expandable element is configured to be received within the delivery catheter lumen, wherein the actuator is configured to retract the delivery catheter from overtop of the expandable element to enable expansion of the expandable element.

26. The catheter assembly of claim 21, wherein the actuator further comprises a fluid-infusion port fluidically coupled to the delivery catheter lumen, and wherein the delivery catheter defines a plurality of openings configured to release a fluid received through the fluid-infusion port.

27. The catheter assembly of claim 21:
   wherein the actuator comprises a delivery catheter actuator, and
   wherein the retrieval catheter handle comprises a retrieval catheter actuator configured to cause expansion and contraction of the retrieval funnel.

28. The catheter assembly of claim 21, wherein the retrieval catheter handle defines an aspiration port, and wherein the retrieval catheter handle further comprises a removable adaptor configured to convert the aspiration port to a smaller-bore fluid port.

* * * * *